US012584907B1

(12) United States Patent
Zeng et al.

(10) Patent No.: US 12,584,907 B1
(45) Date of Patent: Mar. 24, 2026

(54) VISCOELASTIC HYDROGEL REGULATION OF ORGANOID PATTERNING AND VASCULARIZATION

(71) Applicant: The Florida State University Research Foundation, Inc., Tallahassee, FL (US)

(72) Inventors: Changchun Zeng, Tallahassee, FL (US); Yan Li, Tallahassee, FL (US); Xingchi Chen, Tallahassee, FL (US)

(73) Assignee: The Florida State University Research Foundation, Inc., Tallahassee, FL (US)

( * ) Notice: Subject to any disclaimer, the term of this patent is extended or adjusted under 35 U.S.C. 154(b) by 0 days.

(21) Appl. No.: 19/175,432

(22) Filed: Apr. 10, 2025

Related U.S. Application Data

(62) Division of application No. 18/952,423, filed on Nov. 19, 2024, now Pat. No. 12,442,815.

(60) Provisional application No. 63/697,111, filed on Sep. 20, 2024.

(51) Int. Cl.
| | |
|---|---|
| *C12N 5/077* | (2010.01) |
| *C12N 5/071* | (2010.01) |
| *C12N 5/079* | (2010.01) |
| *G01N 33/50* | (2006.01) |

(52) U.S. Cl.
CPC ....... *G01N 33/5082* (2013.01); *C12N 5/0618* (2013.01); *C12N 5/0691* (2013.01); *C12N 5/0697* (2013.01); *G01N 33/5023* (2013.01); *C12N 2513/00* (2013.01); *C12N 2533/40* (2013.01); *C12N 2537/10* (2013.01)

(58) Field of Classification Search
CPC .............. G01N 33/5082; C12N 5/0618; C12N 5/0691; C12N 5/0697; C12N 2513/00; C12N 2533/40; C12N 2537/10
See application file for complete search history.

(56) References Cited

U.S. PATENT DOCUMENTS

2013/0288366 A1 * 10/2013 Li .......................... C07K 14/78
435/402

FOREIGN PATENT DOCUMENTS

CN 113425899 A * 9/2021 ......... C08B 37/0072

OTHER PUBLICATIONS

Russ, D.E., Cross, R.B.P., Li, L., Koch, S.C., Matson, K.J.E., Yadav, A., Alkaslasi, M.R., Lee, D.I., Le Pichon, C.E., Menon, V. and Levine, A.J., 2021. A harmonized atlas of mouse spinal cord cell types and their spatial organization. Nat. Commun. 12, 5722 [online] (Year: 2021).*

Ondeck, M.G. and Engler, A.J., 2016. Mechanical characterization of a dynamic and tunable methacrylated hyaluronic acid hydrogel. Journal of biomechanical engineering, 138(2), p. 021003. (Year: 2016).*

Ryu, J., Kim, S., Oh, I., Kato, S., Kosuge, T., Sokolova, A.V., Lee, J., Otsuka, H. and Sohn, D., 2019. Internal structure of hyaluronic acid hydrogels controlled by iron (III) ion-catechol complexation. Macromolecules, 52(17), pp. 6502-6513. (Year: 2019).*

Asadikorayem M., et al., "Zwitterionic Granular Hydrogel for Cartilage Tissue Engineering," Advanced Healthcare Materials, 2024, vol. 13, Article No. 2301831, 14 Pages.

Bejoy J., et al., "Differential Effects of Heparin and Hyaluronic Acid on Neural Patterning of Human Induced Pluripotent Stem Cells," ACS Biomaterials Science & Engineering, Dec. 10, 2018, vol. 4, No. 12, pp. 4354-4366 (27 Pages).

Bejoy J., et al., "Wnt/Yes-Associated Protein Interactions during Neural Tissue Patterning of Human Induced Pluripotent Stem Cells," Tissue Engineering: Part A, 2018, vol. 24, No. 7-8, pp. 546-558.

Bissoli I., et al., "Induced Pluripotent Stem Cell-Based Models: Are We Ready for that Heart in a Dish?," Frontiers in Cell and Developmental Biology, Jan. 19, 2023, vol. 11, Article No. 1129263, 5 Pages.

Cao Y., et al., "Covalently Attached Slippery Surface Coatings to Reduce Protein Adsorptions on Poly (Dimethylsiloxane) Planar Surfaces and 3D Microfluidic Channels," ACS Applied Materials and Interfaces, 2023, vol. 15, pp. 9987-9995.

Chanmee T., et al., "Hyaluronan: A Modulator of the Tumor Microenvironment," Cancer Letters, 2016, vol. 375, No. 1, pp. 20-30.

Chaudhuri O., et al., "Effects of Extracellular Matrix Viscoelasticity on Cellular Behaviour," Nature, Aug. 27, 2020, vol. 584, No. 7822, pp. 535-546.

Chaudhuri O., et al., "Hydrogels with Tunable Stress Relaxation Regulate Stem Cell Fate and Activity," Nature Materials, Mar. 2016, vol. 15, No. 3, pp. 326-334 (11 Pages).

Chaudhuri O., "Viscoelastic Hydrogels for 3D Cell Culture," Biomaterials Science, 2017, vol. 5, No. 8, pp. 1480-1490.

Chen X., et al., "Dynamic 3D On-Chip BBB Model Design, Development, and Applications in Neurological Diseases," Cells, 2021, vol. 10, Article No. 3183, 23 Pages.

Chen X., et al., "Surface Engineering of Auxetic Scaffolds for Neural and Vascular Differentiation from Human Pluripotent Stem Cells," Advanced Healthcare Materials, Jan. 2023, vol. 12, No. 6, Article No. e2202511, 27 Pages.

Cheng B., et al., "Predicting YAP/TAZ Nuclear Translocation in Response to ECM Mechanosensing," Biophysical Journal, Jan. 3, 2023, vol. 122, No. 1, pp. 43-53.

(Continued)

*Primary Examiner* — Jeremy C Flinders
*Assistant Examiner* — Masudur Rahman
(74) *Attorney, Agent, or Firm* — Meunier Carlin & Curfman LLC

(57) ABSTRACT

Disclosed herein are spinal cord models including a cell scaffold including methacrylated hyaluronic acid (HAMA) and dopamine-modified hyaluronic acid (HA-Cat), and a spinal cord spheroid or organoid or a fragment thereof cultured on the cell scaffold. Said spinal cord spheroids or organoids or fragments thereof can be co-cultured with blood vessel spheroid organoids to form blood-spinal cord barrier models. Also disclosed herein are methods of making and using said models.

13 Claims, 15 Drawing Sheets

Specification includes a Sequence Listing.

(56)                    References Cited

OTHER PUBLICATIONS

Dicker K.T., et al., "Hyaluronan: A Simple Polysaccharide with Diverse Biological Functions," Acta biomaterialia, Apr. 2014, vol. 10, No. 4, pp. 1558-1570 (30 Pages).

Dijkgraaf L.C., et al., "Normal Cartilage Structure, Biochemistry, and Metabolism: A Review of the Literature," Journal of Oral and Maxillofacial Surgery, 1995, vol. 53, No. 8, pp. 924-929.

Ding S., et al., "Modulation of Human Mesenchymal and Pluripotent Stem Cell Behavior Using Biophysical and Biochemical Cues: A Review," Biotechnology and Bioengineering, Feb. 2017, vol. 114, No. 2, pp. 260-280.

D'Mello R., et al., "Spinal Cord Mechanisms of Pain," British Journal of Anaesthesia, 2008, vol. 101, No. 1, pp. 8-16.

Du Z-W., et al., "Generation and Expansion of Highly Pure Motor Neuron Progenitors from Human Pluripotent Stem Cells," Nature Communications, 2015, vol. 6, No. 1, Article No. 6626, pp. 1-9.

Elosegui-Artola A., et al., "Matrix Viscoelasticity Controls Spatiotemporal Tissue Organization," Nature Materials, Jan. 2023, vol. 22, No. 1, pp. 117-127 (34 Pages).

Elosegui-Artola A., "The Extracellular Matrix Viscoelasticity as a Regulator of Cell and Tissue Dynamics," Current Opinion in Cell Biology, 2021, vol. 72, pp. 10-18.

Fox A.J.S., et al., "The Basic Science of Articular Cartilage: Structure, Composition, and Function," Sports Health, Nov.-Dec. 2009, vol. 1, No. 6, pp. 461-468.

Fraser J.R.E., et al., "Hyaluronan: Its Nature, Distribution, Functions and Turnover," Journal of Internal Medicine, 1997, vol. 242, No. 1, pp. 27-33.

Gattazzo F., et al., "Extracellular Matrix: A Dynamic Microenvironment for Stem Cell Niche," Biochimica et Biophysica Acta (BBA)—General Subjects, 2014, vol. 1840, No. 8, pp. 2506-2519.

Gokila S., et al., "Development of 3D Scaffolds Using Nanochitosan/Silk-fibroin/Hyaluronic Acid Biomaterials for tissue Engineering Applications," International Journal of Biological Macromolecules, 2018, vol. 120, pp. 876-885.

Gong M., et al., "A Dopamine-Methacrylated Hyaluronic Acid Hydrogel as an Effective Carrier for Stem Cells in Skin Regeneration Therapy," Cell Death and Disease, 2022, vol. 13, Article No. 738, 11 Pages.

Gribaudo S., et al., "Self-organizing Models of Human Trunk Organogenesis Recapitulate Spinal Cord and Spine Co-Morphogenesis," Nature Biotechnology, Aug. 2024, vol. 42, pp. 1243-1253 (35 Pages).

Hauptstein J., et al., "Hyaluronic Acid-Based Bioink Composition Enabling 3D Bioprinting and Improving Quality of Deposited Cartilaginous Extracellular Matrix," Advanced Healthcare Materials, 2020, vol. 9, No. 15, Article No. 2000737, 15 Pages.

Homan K.A., et al., "Flow-enhanced Vascularization and Maturation of Kidney Organoids in Vitro," Nature Methods, Mar. 2019, vol. 16, No. 3, pp. 255-262 (25 Pages).

Hor J.H., et al., "Cell Cycle Inhibitors Protect Motor Neurons in an Organoid Model of Spinal Muscular Atrophy," Cell Death and Disease, 2018, vol. 9, No. 11, pp. 1-12.

Hor J-H., "Generating Ventral Spinal Organoids from Human Induced Pluripotent Stem Cells," Methods in Cell Biology, Elsevier, 2020, vol. 159, pp. 257-277.

Horkay F., et al., "Gel-Like Behavior in Aggrecan Assemblies," The Journal of Chemical Physics, 2008, vol. 128, No. 13, Article No. 135103, pp. 135103-1-135103-7.

Indana D., et al., "Viscoelasticity and Adhesion Signaling in Biomaterials Control Human Pluripotent Stem Cell Morphogenesis in 3D Culture," Advanced Materials, 2021, vol. 33, No. 43, Article No. 2101966, 16 Pages.

Ireland R.G., et al., "Human Pluripotent Stem Cell Mechanobiology: Manipulating the Biophysical Microenvironment for Regenerative Medicine and Tissue Engineering Applications," Stem Cells, 2015, vol. 33, No. 11, pp. 3187-3196 (11 Pages).

Jeske R., et al., "Engineering Human Mesenchymal Bodies in a Novel 3D-Printed Microchannel Bioreactor for Studying Extracellular Vesicle Biogenesis," Bioengineering (Basel), 2022, vol. 9, No. 12, Article No. 795, 14 Pages.

Jeske R., et al., "Upscaling Human Mesenchymal Stem Cell Production in a Novel Vertical Wheel Bioreactor Enhances Extracellular Vesicle Secretion and Cargo Profile," Bioactive Materials, 2023, vol. 25, pp. 732-747.

Jin L-Y., et al., "Blood-Spinal Cord Barrier in Spinal Cord Injury: A Review," Journal of Neurotrauma, May 1, 2021, vol. 38, No. 9, pp. 1203-1224.

Kaitsuka T., et al., "Response of Pluripotent Stem Cells to Environmental Stress and Its Application for Directed Differentiation," Biology, 2021, vol. 10, No. 2, Article No. 84, 16 Pages.

Khaing Z.Z., et al., "Hyaluronic Acid and Neural Stem Cells: Implications for Biomaterial Design," Journal of Materials Chemistry B, 2015, vol. 3, No. 40, pp. 7850-7866.

Khanna A., et al., "Extracellular Matrix-Based Biomaterials for Cardiovascular Tissue Engineering," Journal of Cardiovascular Development and Disease, 2021, vol. 8, No. 11, Article No. 137, 25 Pages.

Kwon M.Y., et al., "Influence of Hyaluronic Acid Modification on CD44 Binding towards the Design of Hydrogel Biomaterials," Biomaterials, Nov. 2019, vol. 222, Article No. 119451, 21 Pages.

Lancaster M.A., et al., "Organogenesis in a Dish: Modeling Development and Disease Using Organoid Technologies," Science, Jul. 18, 2014, vol. 345, No. 6194, Article No. 1247125, p. 283 (10 Pages).

Lee J-H., et al., "Production of Human Spinal-cord Organoids Recapitulating Neural-Tube Morphogenesis," Nature Biomedical Engineering, Apr. 2022, vol. 6, No. 4, pp. 435-448 (24 Pages).

Li Y., et al., "Review of Advances in Electrospinning-based Strategies for Spinal Cord Regeneration," Materials Today Chemistry, 2022, vol. 24, Article No. 100944, 20 Pages.

Lundell A., et al., "Structural Basis for Interactions between Tenascins and Lectican C-Type Lectin Domains: Evidence for a Crosslinking Role for Tenascins," Structure, Aug. 2004, vol. 12, No. 8, pp. 1495-1506.

Lupon E., et al., "Engineering Vascularized Composite Allografts Using Natural Scaffolds: A Systematic Review," Tissue Engineering Part B: Reviews, 2022, vol. 28, No. 3, pp. 677-693.

Lutolf M.P., et al., "Synthetic Biomaterials as Instructive Extracellular Microenvironments for Morphogenesis in Tissue Engineering," Nature Biotechnology, Jan. 2005, vol. 23, No. 1, pp. 47-55.

Mansour A.A., et al., "An In Vivo Model of Functional and Vascularized Human Brain Organoids," Nature Biotechnology, Apr. 16, 2018, vol. 36, No. 5, pp. 432-441 (42 Pages).

Muir V.G., et al., "Sticking Together: Injectable Granular Hydrogels with Increased Functionality via Dynamic Covalent Inter-Particle Crosslinking," Small, Sep. 2022, vol. 18, No. 36 (e2201115), 28 Pages.

Muok L., et al., "Extracellular Vesicle Biogenesis of Three-Dimensional Human Pluripotent Stem Cells in a Novel Vertical-Wheel Bioreactor," Journal of Extracellular Biology, 2024, vol. 3, Article No. e133, 28 Pages.

Murphy W.L., et al., "Materials as Stem Cell Regulators," Nature Materials, Jun. 2014, vol. 13, No. 6, pp. 547-557 (24 Pages).

Ogura T., et al., "Three-dimensional Induction of Dorsal, Intermediate and Ventral Spinal Cord Tissues from Human Pluripotent Stem Cells," Development, 2018, vol. 145, No. 16, 12 Pages.

Pan F., et al., "Topographic Effect on Human Induced Pluripotent Stem Cells Differentiation towards Neuronal Lineage," Biomaterials, 2013, vol. 34, No. 33, pp. 8131-8139.

Pedron S., et al., "Extracellular Hyaluronic Acid Influences the Efficacy of EGFR Tyrosine Kinase Inhibitors in a Biomaterial Model of Glioblastoma," Advanced Healthcare Materials, Nov. 2017, vol. 6, No. 21, Article No. 1700529, 20 Pages.

Perkins K.L., et al., "Brain Extracellular Space, Hyaluronan, and the Prevention of Epileptic Seizures," Reviews in the Neurosciences, Nov. 27, 2017, vol. 28, No. 8, pp. 869-892 (39 Pages).

Pettinato G., et al., "Generation of Fully Functional Hepatocyte-like Organoids from Human Induced Pluripotent Stem Cells Mixed with Endothelial Cells," Scientific Reports, 2019, vol. 9, No. 1, Article No. 8920, 21 Pages.

(56) References Cited

OTHER PUBLICATIONS

Qian T., et al., "Directed Differentiation of Human Pluripotent Stem Cells to Blood-brain Barrier Endothelial Cells," Science Advances, Nov. 8, 2017, vol. 3, No. 11, Article No. e1701679, 12 Pages.

Rauch U., "Brain Matrix: Structure, Turnover and Necessity," Biochemical Society Transactions, 2007, vol. 35 (Pt 4), pp. 656-660.

Revah O., et al., "Maturation and Circuit Integration of Transplanted Human Cortical Organoids," Nature, Oct. 13, 2022, vol. 610, No. 7931, pp. 319-326 (34 Pages).

Roth J.G., et al., "Advancing Models of Neural Development with Biomaterials," Nature Reviews Neuroscience, Oct. 2021, vol. 22, No. 10, pp. 593-615.

Roth J.G., et al., "Tunable Hydrogel Viscoelasticity Modulates Human Neural Maturation," Science Advances, Oct. 20, 2023, vol. 9, No. 42, Article No. eadh8313, 18 Pages.

Simian M., et al., "Organoids: A Historical Perspective of Thinking in Three Dimensions," Journal of Cell Biology, 2017, vol. 216, No. 1, pp. 31-40.

Song L., et al., "Assembly of Human Stem Cell-Derived Cortical Spheroids and Vascular Spheroids to Model 3-D Brain-like Tissues," Scientific Reports, 2019, vol. 9, No. 1, Article No. 5977, 16 Pages.

Song L., et al., "Functionalization of Brain Region-Specific Spheroids with Isogenic Microglia-like Cells," Scientific Reports, 2019, vol. 9, Article No. 11055, 18 Pages.

Song L., et al., "Nanotopography Promoted Neuronal Differentiation of Human Induced Pluripotent Stem Cells," Colloids and Surfaces B: Biointerfaces, 2016, vol. 148, pp. 49-58.

Stern R., et al., "Hyaluronan Fragments: An Information-Rich System," European Journal of Cell Biology, 2006, vol. 85, No. 8, pp. 699-715.

Stern R., "Hyaluronan Catabolism: A New Metabolic Pathway," European Journal of Cell Biology, 2004, vol. 83, No. 7, pp. 317-325.

Sun Y., et al., "Hippo/YAP-Mediated Rigidity-Dependent Motor Neuron Differentiation of Human Pluripotent Stem Cells," Nature Materials, Jun. 2014, vol. 13, No. 6, pp. 599-604 (12 Pages).

Tan H-Y., et al., "Human Mini-Brain Models," Nature Biomedical Engineering, Jan. 2021, vol. 5, No. 1, pp. 11-25.

Tang S., et al., "Dynamic Covalent Hydrogels as Biomaterials to Mimic the Viscoelasticity of Soft Tissues," Progress in Materials Science, 2021, vol. 120, Article No. 100738, 25 Pages.

Wang P-Y., et al., "Modulation of Human Multipotent and Pluripotent Stem Cells Using Surface Nanotopographies and Surface-immobilised Bioactive Signals: A Review," Acta Biomaterialia, 2016, vol. 45, pp. 31-59.

Wimmer R.A., et al., "Human Blood Vessel Organoids as a Model of Diabetic Vasculopathy," Nature, Jan. 24, 2019, vol. 565, pp. 505-510 (34 Pages).

Wu D.T., et al., "Viscoelastic Biomaterials for Tissue Regeneration," Tissue Engineering Part C: Methods, 2022, vol. 28, No. 7, pp. 289-300.

Xu C., et al., "Two-dimensional-Germanium Phosphide-Reinforced Conductive and Biodegradable Hydrogel Scaffolds Enhance Spinal Cord Injury Repair," Advanced Functional Materials, 2021, vol. 31, Article No. 2104440, 14 Pages.

Xue W., et al., "Generation of Dorsoventral Human Spinal Cord Organoids via Functionalizing Composite Scaffold for Drug Testing," iScience, Jan. 20, 2023, vol. 26, No. 1, Article No. 105898, pp. 1-20 (21 Pages).

Yamamoto T., et al., "Improving the Differentiation Potential of Pluripotent Stem Cells by Optimizing Culture Conditions," Scientific Reports, 2022, vol. 12, No. 1, Article No. 14147, 12 Pages.

Yan Y., et al., "3D Bioprinting of Human Neural Tissues with Functional Connectivity," Cell Stem Cell, Feb. 1, 2024, vol. 31, No. 2 (e7), pp. 260-274 (54 Pages).

Yuan X., et al., "Engineering Extracellular Vesicles by Three-Dimensional Dynamic Culture of Human Mesenchymal Stem Cells," Journal of Extracellular Vesicles, 2022, vol. 11, No. 6, Article No. e12235, 23 Pages.

Zhang S., et al., "Vascularized Organoids on a Chip: Strategies for Engineering Organoids with Functional Vasculature," Lab on a Chip, 2021, vol. 21, No. 3, pp. 473-488.

Zhou G., et al., "Progress in the Generation of Spinal Cord Organoids Over the Past Decade and Future Perspectives," Neural Regeneration Research, May 2024, vol. 19, No. 5, pp. 1013-1019.

Zhu W., et al., "Determination of Kinetic Changes of Aggrecan-Hyaluronan Interactions in Solution from Its Rheological Properties," Journal of Biomechanics, 1994, vol. 27, No. 5, pp. 571-579.

Zhu Z., et al., "Hyaluronic Acid: A Versatile Biomaterial in Tissue Engineering," Plastic and Aesthetic Research, Dec. 29, 2017, vol. 4, pp. 219-227.

Zimmermann D.R., et al., "Extracellular Matrix of the Central Nervous System: From Neglect to Challenge," Histochemistry and Cell Biology, 2008, vol. 130, pp. 635-653.

\* cited by examiner 0.25% HAMA                    0.5% HAMA                    1% HAMA

VISCOELASTIC HYDROGEL REGULATION OF ORGANOID PATTERNING AND VASCULARIZATION

CROSS REFERENCE TO RELATED APPLICATIONS

This application is a divisional of U.S. application Ser. No. 18/952,423, filed Nov. 19, 2024, which claims the benefit of priority to U.S. Provisional Application No. 63/697,111, filed Sep. 20, 2024, which is incorporated by reference herein in its entirety.

GOVERNMENT SUPPORT CLAUSE

This invention was made with government support under Grant No. 1917618 awarded by the National Science Foundation. The Government has certain rights in the invention.

REFERENCE TO SEQUENCE LISTING

The sequence listing submitted on Apr. 10, 2025, as an.XML file entitled "10850-118US1_ST26.xml" created on Nov. 14, 2024, and having a file size of 51,882 bytes is hereby incorporated by reference pursuant to 37 C.F.R. § 1.52 (c) (5).

BACKGROUND

The spinal cord is part of the central nervous system and provides a connection between the brain and lower back, which delivers nerve signals from the brain to the body to control locomotion and feeling sensations [1]. Human induced pluripotent stem cells (hiPSCs) can be directly induced into different types of region-specific brain organoids, including spinal cord organoids, for studying neurodevelopment and neurodegeneration [2]. These three-dimensional (3D) organoids are usually generated in suspension. To generate different subtypes of neuronal cells in vitro such as motor neurons, hiPSCs can be induced by small molecules to become functional neural cells with a high conversion rate in a 2D culture [3], and these cells can be assembled into 3D neural structure [4]. Currently, there are still many limitations for developing more complex systems in 3D organoids. For example, the lack of specific mature pattern structure, such as rostro-caudal patterning, decreased disease modeling accuracy and reduced model effectiveness [5]. Furthermore, small molecules may not be sufficient to provide spatial cues for specific cells arranged in 3D structure, which are essential for functional neuronal and synapse maturation. Additionally, environmental stimulations, such as chemical and mechanical cues, could be less effective in 3D organoids compared to in vivo environment due to the missing signaling in vitro, which may lead to the lack of function [6, 7].

Therefore, methods with more in vivo-like microenvironment are needed to pattern hiPSC-derived spinal cord organoids, and to provide new insights into the principles of tissue patterning during spinal neurogenesis [8]. These needs and others are at least partially satisfied by the present disclosure.

SUMMARY

In one aspect, provided is a spinal cord model including: a cell scaffold including methacrylated hyaluronic acid (HAMA) and dopamine-modified hyaluronic acid (HA- Cat); and a spinal cord spheroid or organoid or a fragment thereof cultured on the cell scaffold and expressing one or more ventral markers, dorsal markers, and/or interneuron markers.

In another aspect, provided is a blood-spinal cord barrier model including a spinal cord spheroid or organoid or a fragment thereof derived from any of the disclosed spinal cord models co-cultured with a blood vessel spheroid or organoid or a fragment thereof.

In yet another aspect, provided is a method of modeling a spinal cord, the method including culturing a plurality of induced pluripotent stem cells on a cell scaffold to form a spinal cord spheroid or organoid or a fragment thereof, the cell scaffold including methacrylated hyaluronic acid (HAMA) and dopamine-modified hyaluronic acid (HA-Cat); wherein the method causes the spinal cord spheroid or organoid or a fragment thereof to express one or more ventral markers, dorsal markers, and/or interneuron markers.

In yet still another aspect, provided is a method of modeling a blood-spinal cord barrier, the method including: a) culturing a plurality of induced pluripotent stem cells on a cell scaffold to form a spinal cord spheroid or organoid or a fragment thereof, the cell scaffold including methacrylated hyaluronic acid (HAMA) and dopamine-modified hyaluronic acid (HA-Cat); and b) co-culturing the spinal cord spheroid or organoid or a fragment thereof with a blood vessel spheroid or organoid or a fragment thereof; wherein step a) causes the spinal cord spheroid or organoid or a fragment thereof to express one or more ventral markers, dorsal markers, and/or interneuron markers.

In yet still another aspect, provided is a method of screening a therapeutic agent, the method including: a) culturing a plurality of induced pluripotent stem cells on a cell scaffold to form a spinal cord spheroid or organoid or a fragment thereof, the cell scaffold including methacrylated hyaluronic acid (HAMA) and dopamine-modified hyaluronic acid (HA-Cat); and b) administering the therapeutic agent to the spinal cord spheroid or organoid or fragment thereof.

In yet still another aspect, provided is a method of screening a therapeutic agent, the method including: a) culturing a plurality of induced pluripotent stem cells on a cell scaffold to form a spinal cord spheroid or organoid or a fragment thereof, the cell scaffold including methacrylated hyaluronic acid (HAMA) and dopamine-modified hyaluronic acid (HA-Cat); b) culturing a plurality of induced pluripotent stem cells on the cell scaffold to form a spinal cord spheroid or organoid or a fragment thereof; c) co-culturing the spinal cord spheroid or organoid or a fragment thereof with a blood vessel spheroid or organoid or a fragment thereof; and d) administering the therapeutic agent to the spinal cord spheroid or organoid or fragment thereof and/or the blood vessel spheroid or organoid or a fragment thereof.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF DRAWINGS

FIG. 1A is a schematic illustration of methods of (i) fabrication and synthesis of HAMA, (ii) fabrication and synthesis of HAMA@HA-Cat, (iii) fabrication and synthesis of hydrogels, and (iv) $Fe^{3+}$ curing HA-Cat hydrogels. FIG. 1B shows quantification of the compression modulus, and FIG. 1C shows tanδ of the hydrogels by compression and rheological test. (n>3 measurements per gel).

FIG. 1D shows the stress relaxation test applied to the 4 selected HAMA hydrogels and regression performed by a modified Maxwell model to get stress relaxation time.

FIG. 2A is 1H NMR results which show the success of grafting MA group to HA chains. FIG. 2B shows fabricating the HAMA library with different MW and concentrations. FIGS. 2C-2D show four types of HAMA hydrogels were selected from a series of HAMA hydrogels with different concentrations to make a library for matching sample properties. FIG. 2C shows a plot of viscoelasticity (tand) of all HAMA hydrogels. All tanδ values were obtained under 1 Hz. FIG. 2D shows a plot of compression modulus of all HAMA hydrogels.

FIG. 6A is a schematic illustration of ventral hSCO differentiation protocol. FIGS. 6B-6D show immunostaining and flow cytometry analysis for marker expression of hSCO differentiation. FIG. 6B and FIG. 6D were taken using confocal microscopy. Scale bar=50 µm. FIG. 6E shows quantitative RT-PCR for relative mRNA expression of (i) ventral markers, (ii) interneuron markers and (iii) dorsal markers after biochemical induction (n=3). * indicates $p \leq 0.05$, : $p \leq 0.01$, *: $p \leq 0.001$.

FIG. 7A shows a comparison of the differentiation markers between iPSC aggregates and hSCO spheroids. FIG. 7B shows a ventral hSCO marker expression in the organoids derived from different differentiation methods. * indicates $p \leq 0.05$, : $p \leq 0.01$, *: $p \leq 0.001$.

FIG. 8A shows hSCO at day 40 with static culture. scale bar=200 µm. FIG. 8B shows replated day-44 hSCO with axons extensions. Scale bar=50 µm.

FIG. 10A shows hiPSC culture with HAMA and HAMA/Matrigel mixture for 7 days. Scale bar=50 µm. FIG. 10B shows a DNA assay, and FIG. 10C shows Live/Dead flow cytometry analysis for determining proliferation rate and survival rate of hiPSCs cultured with different HAMA hydrogels, respectively. FIG. 10D shows images of morphology of the organoids with different hydrogels over the time. Scale bar=200 µm. FIG. 10E shows quantification of diameter and circularity of hSCOs cultured in different HAMA hydrogels for morphogenesis. * indicates $p \leq 0.05$, : $p \leq 0.01$, *: $p \leq 0.001$.

FIG. 12A shows flow cytometry analysis of expression of different ventral markers when generating hSCOs in different hydrogels. FIG. 12B shows a summary of 3 runs of flow cytometry analysis for identification ventral hSCO marker expression. FIG. 12C shows RT-PCR analysis of relative mRNA expression for different region-specific patterning markers during generation of hSCOs at day 35 (n=3). * indicates $p \leq 0.05$, : $p \leq 0.01$, *: $p \leq 0.001$. FIG. 12D shows (i) electrophysiology to show sodium and potassium currents for the replated hSCOs at day 40, and (ii) morphology of outgrowth cells of the replated hSCOs for electrophysiology. Scale bar=20 µm.

FIG. 14A shows EC marker expression of hBVOs derived from different seeding densities (10k, 20k, 30k), replating condition (re), and protocols (hBVO vs. vsc protocol).

FIG. 14B shows EC marker expression of hBVOs from the differentiation by adding different growth factors BMP4 and VEGF.

FIG. 15A shows morphology of the merging process of two types of organoids indicated by cell-tracker (red) hBVOs. FIGS. 15B-15C show RT-PCR analysis for relative mRNA expression of ventral spinal cord genes, endothelial cells (EC), and blood-brain barrier (BBB) genes during hBVO and different hSCO coculturing. n=3, ns: p>0.05, * indicates $p \leq 0.05$, : $p \leq 0.01$, *: $p \leq 0.001$.

FIGS. 16A-16E show rheological test and compression test performed to determine mechanical properties for the four hydrogels (Gel 5-8 in sequence). FIG. 16A shows storage modulus, FIG. 16B shows tand, FIG. 16C shows compression modulus, and FIG. 16D shows the viscoelasticity of the hydrogels further determined by stress relaxation test. FIG. 16E shows RT-PCR analysis of relative mRNA expression for different region-specific patterning markers of hSCOs at day 35. n=3, * indicates $p \leq 0.05$.

FIG. 17A shows images of YAP localization. Scale bar: 50 µm. FIG. 17B shows the quantitative measurements of nuclear to cytoplasmic YAP localization for different hydrogel conditions. * indicates $p \leq 0.05$, **: $p \leq 0.01$.

DETAILED DESCRIPTION

Figures 1A, 1B, 1C, 1D:
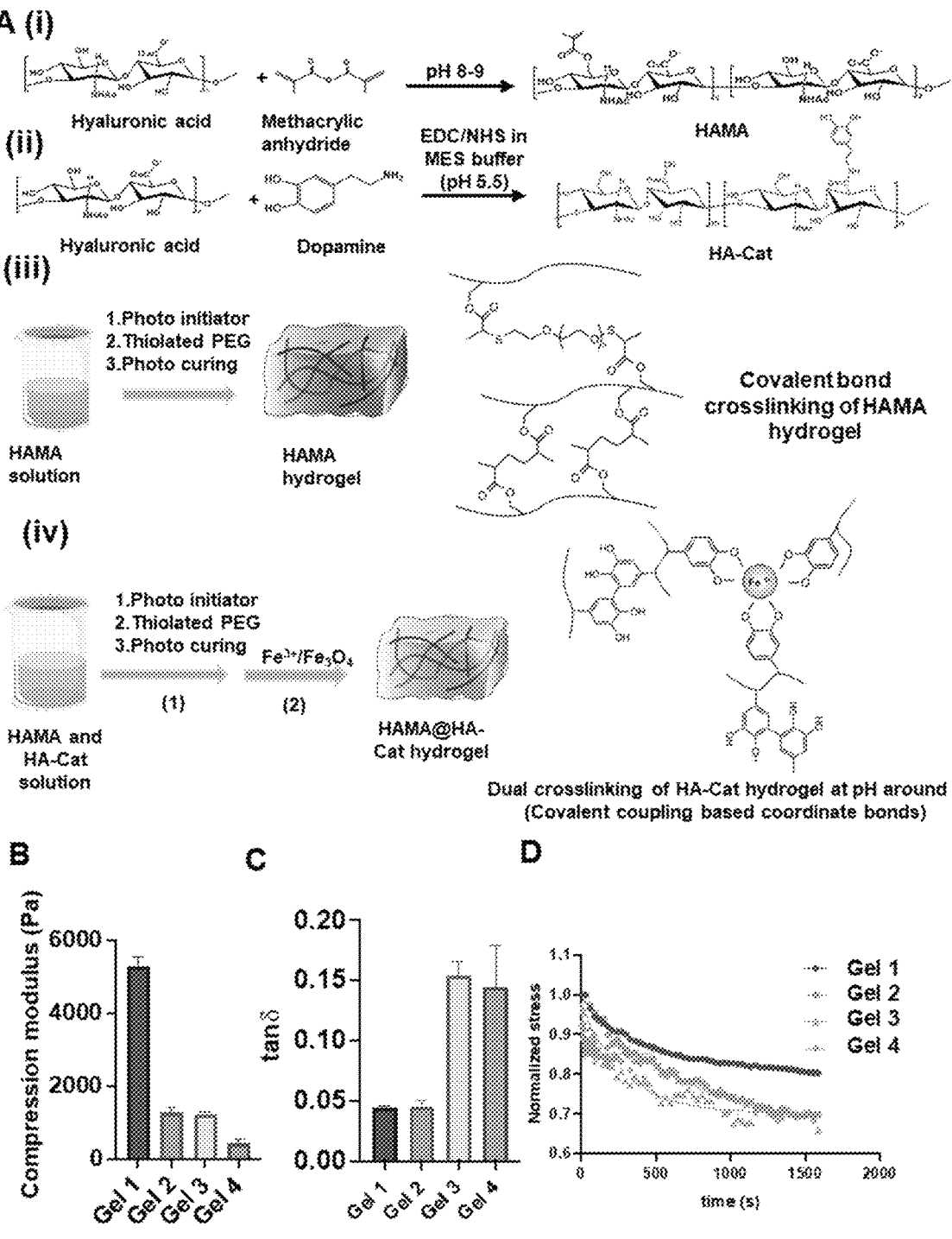
FIGS. 1A-1D depict HAMA synthesis and characterization.

It is appreciated that certain features of the disclosure, which are, for clarity, described in the context of separate aspects, can also be provided in combination with a single aspect. Conversely, various features of the disclosure, which are, for brevity, described in the context of a single aspect, can also be provided separately or in any suitable subcombination. Unless defined otherwise, all technical and scientific terms used herein have the same meaning as commonly understood by one of ordinary skill in the art. Methods and materials similar or equivalent to those described herein can be used in the practice or testing of the present disclosure.

5

Definitions

In this specification and in the claims that follow, reference will be made to a number of terms, which shall be defined to have the following meanings:

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of.

As used in the specification and the appended claims, the singular forms "a," "an" and "the" include plural referents unless the context clearly dictates otherwise. Thus, for example, reference to "a compound", "a composition", or "a cancer", includes, but is not limited to, two or more such compounds, compositions, or cancers, and the like.

It should be noted that ratios, concentrations, amounts, and other numerical data can be expressed herein in a range format. It can be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it can be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the term "effective amount" refers to an amount that is sufficient to achieve the desired modification of a physical property of the composition or material. For example, an "effective amount" of a monomer refers to an amount that is sufficient to achieve the desired improvement in the property modulated by the formulation component, e.g. desired antioxidant release rate or viscoelasticity. The specific level in terms of wt % in a composition required as an effective amount will depend upon a variety of factors including the amount and type of monomer, amount and type of polymer, e.g., acrylamide, amount of antioxidant, and desired release kinetics.

As used herein, the term "therapeutically effective amount" refers to an amount that is sufficient to achieve the desired therapeutic result or to have an effect on undesired symptoms but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors within the knowledge and expertise of the health practitioner and which may be well known in the medical arts. In the case of treating a particular disease or condition, in some instances, the desired response can be inhibiting the progression of the disease or condition. This may involve only slowing the progression of the disease temporarily. However, in other instances, it may be desirable to halt the progression of the disease permanently. This can be monitored by routine diagnostic methods known to one of ordinary skill in the art for any particular disease. The desired response to treatment of the disease or condition also can be delaying the onset or even preventing the onset of the disease or condition.

For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. It is generally preferred that a maximum dose of the pharmacological agents of the invention (alone or in combination with other therapeutic agents) be used, that is, the highest safe dose according to sound medical judgment. It will be understood by those of ordinary skill in the art however, that a patient may insist upon a lower dose or tolerable dose for medical reasons, psychological reasons or for virtually any other reasons.

A response to a therapeutically effective dose of a disclosed drug delivery composition can be measured by determining the physiological effects of the treatment or medication, such as the decrease or lack of disease symptoms following administration of the treatment or pharmacological agent. Other assays will be known to one of ordinary skill in the art and can be employed for measuring the level of the response. The amount of a treatment may be varied for example by increasing or decreasing the amount of a disclosed compound and/or pharmaceutical composition, by changing the disclosed compound and/or pharmaceutical composition administered, by changing the route of administration, by changing the dosage timing and so on. Dosage can vary, and can be administered in one or more dose administrations daily, for one or several days. Guidance can be found in the literature for appropriate dosages for given classes of pharmaceutical products.

As used herein, the term "prophylactically effective amount" refers to an amount effective for preventing onset or initiation of a disease or condition.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the terms "optional" or "optionally" means that the subsequently described event or circumstance can or cannot occur, and that the description includes instances where said event or circumstance occurs and instances where it does not.

As used interchangeably herein, "subject," "individual," or "patient" can refer to a vertebrate organism, such as a mammal (e.g. human). "Subject" can also refer to a cell, a population of cells, a tissue, an organ, or an organism, preferably to human and constituents thereof.

As used herein, the terms "treating" and "treatment" can refer generally to obtaining a desired pharmacological and/or physiological effect. The effect can be, but does not necessarily have to be, prophylactic in terms of preventing or partially preventing a disease, symptom or condition thereof. The effect can be therapeutic in terms of a partial or complete cure of a disease, condition, symptom or adverse effect attributed to the disease, disorder, or condition. The term "treatment" as used herein can include any treatment of a disease disorder in a subject, particularly a human and can include any one or more of the following: (a) preventing the disease from occurring in a subject which may be predisposed to the disease but has not yet been diagnosed as having it; (b) inhibiting the disease, i.e., arresting its development; and (c) relieving the disease, i.e., mitigating or ameliorating the disease and/or its symptoms or conditions. The term "treatment" as used herein can refer to both therapeutic treatment alone, prophylactic treatment alone, or both therapeutic and prophylactic treatment. Those in need of treatment (subjects in need thereof) can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, e.g., such as treating the pain of a subject by administration of an analgesic agent even though such agent does not treat the cause of the pain.

As used herein, "dose," "unit dose," or "dosage" can refer to physically discrete units suitable for use in a subject, each unit containing a predetermined quantity of a disclosed compound and/or a pharmaceutical composition thereof calculated to produce the desired response or responses in association with its administration.

As used herein, "therapeutic" can refer to treating, healing, and/or ameliorating a disease, disorder, condition, or side effect, or to decreasing in the rate of advancement of a disease, disorder, condition, or side effect.

Spinal Cord Model

In one aspect, provided is a spinal cord model including: a cell scaffold including methacrylated hyaluronic acid (HAMA) and dopamine-modified hyaluronic acid (HA-Cat); and a spinal cord spheroid or organoid or a fragment thereof cultured on the cell scaffold and expressing one or more ventral markers, dorsal markers, and/or interneuron markers.

In some aspects, the cell scaffold can include up to about 2 wt % HAMA (e.g., up to about 1.9 wt %, up to about 1.8 wt %, up to about 1.7 wt %, up to about 1.6 wt %, up to about 1.5 wt %, up to about 1.4 wt %, up to about 1.3 wt %, up to about 1.2 wt %, up to about 1.1 wt %, up to about 1 wt %, up to about 0.9 wt %, up to about 0.8 wt %, up to about 0.7 wt %, up to about 0.6 wt %, up to about 0.5 wt %, up to about 0.4 wt %, up to about 0.3 wt %, up to about 0.2 wt %, up to about 0.1 wt %, 0 wt %). In some aspects, the cell scaffold can include greater than 0 wt % HAMA (e.g., greater than about 0.1 wt %, greater than about 0.2 wt %, greater than about 0.3 wt %, greater than about 0.4 wt %, greater than about 0.5 wt %, greater than about 0.6 wt %, greater than about 0.7 wt %, greater than about 0.8 wt %, greater than about 0.9 wt %, greater than about 1 wt %, greater than about 1.1 wt %, greater than about 1.2 wt %, greater than about 1.3 wt %, greater than about 1.4 wt %, greater than about 1.5 wt %, greater than about 1.6 wt %, greater than about 1.7 wt %, greater than about 1.8 wt %, greater than about 1.9 wt %, greater than about 2 wt %).

It is considered that the cell scaffold can include an amount of HAMA ranging from any of the minimum values described above to any of the maximum values described above. For example, in some aspects, the cell scaffold can include from 0 wt % to about 2 wt % HAMA (e.g., from about 0.1 wt % to about 1.9 wt %, from about 0.2 wt % to about 1.8 wt %, from about 0.3 wt % to about 1.7 wt %, from about 0.4 wt % to about 1.6 wt %, from about 0.5 wt % to about 1.5 wt %, from about 0.6 wt % to about 1.4 wt %, from about 0.7 wt % to about 1.3 wt %, from about 0.8 wt % to about 1.2 wt %, from about 0.9 wt % to about 1.1 wt %, from 0 wt % to about 1 wt %, from about 0.1 wt % to about 0.9 wt %, from about 0.2 wt % to about 0.8 wt %, from about 0.3 wt % to about 0.7 wt %, from about 0.4 wt % to about 0.6 wt %, from about 1 wt % to about 2 wt %, from about 1.1 wt % to about 1.9 wt %, from about 1.2 wt % to about 1.8 wt %, from about 1.3 wt % to about 1.7 wt %, from about 1.4 wt % to about 1.6 wt %).

In some aspects, the cell scaffold can include up to about 2 wt % HA-Cat (e.g., up to about 1.9 wt %, up to about 1.8 wt %, up to about 1.7 wt %, up to about 1.6 wt %, up to about 1.5 wt %, up to about 1.4 wt %, up to about 1.3 wt %, up to about 1.2 wt %, up to about 1.1 wt %, up to about 1 wt %, up to about 0.9 wt %, up to about 0.8 wt %, up to about 0.7 wt %, up to about 0.6 wt %, up to about 0.5 wt %, up to about 0.4 wt %, up to about 0.3 wt %, up to about 0.2 wt %, up to about 0.1 wt %, 0 wt %). In some aspects, the cell scaffold can include greater than 0 wt % HA-Cat (e.g., greater than about 0.1 wt %, greater than about 0.2 wt %, greater than about 0.3 wt %, greater than about 0.4 wt %, greater than about 0.5 wt %, greater than about 0.6 wt %, greater than about 0.7 wt %, greater than about 0.8 wt %, greater than about 0.9 wt %, greater than about 1 wt %, greater than about 1.1 wt %, greater than about 1.2 wt %, greater than about 1.3 wt %, greater than about 1.4 wt %, greater than about 1.5 wt %, greater than about 1.6 wt %, greater than about 1.7 wt %, greater than about 1.8 wt %, greater than about 1.9 wt %, greater than about 2 wt %).

It is considered that the cell scaffold can include an amount of HA-Cat ranging from any of the minimum values described above to any of the maximum values described above. For example, in some aspects, the cell scaffold can include from 0 wt % to about 2 wt % HA-Cat (e.g., from about 0.1 wt % to about 1.9 wt %, from about 0.2 wt % to about 1.8 wt %, from about 0.3 wt % to about 1.7 wt %, from about 0.4 wt % to about 1.6 wt %, from about 0.5 wt % to about 1.5 wt %, from about 0.6 wt % to about 1.4 wt %, from about 0.7 wt % to about 1.3 wt %, from about 0.8 wt % to about 1.2 wt %, from about 0.9 wt % to about 1.1 wt %, from 0 wt % to about 1 wt %, from about 0.1 wt % to about 0.9 wt %, from about 0.2 wt % to about 0.8 wt %, from about 0.3 wt % to about 0.7 wt %, from about 0.4 wt % to about 0.6 wt %, from about 1 wt % to about 2 wt %, from about 1.1 wt % to about 1.9 wt %, from about 1.2 wt % to about 1.8 wt %, from about 1.3 wt % to about 1.7 wt %, from about 1.4 wt % to about 1.6 wt %).

In some aspects, the HAMA can have a molecular weight of at least about 50 kDa (e.g., at least about 100 kDa, at least about 150 kDa, at least about 200 kDa, at least about 250 kDa, at least about 300 kDa, at least about 350 kDa, at least about 400 kDa, at least about 450 kDa, at least about 500 kDa, at least about 550 kDa, at least about 600 kDa, at least about 650 kDa, at least about 700 kDa, at least about 750 kDa, at least about 800 kDa, at least about 850 kDa, at least about 900 kDa, at least about 950 kDa, at least about 1000 kDa, at least about 1100 kDa, at least about 1200 kDa, at least about 1300 kDa, at least about 1400 kDa, at least about 1500 kDa, at least about 1600 kDa, at least about 1700 kDa, at least about 1800 kDa, at least about 1900 kDa, at least about 2000 kDa). In some aspects, the HAMA can have a molecular weight of up to about 2000 kDa (e.g., up to about 1900 kDa, up to about 1800 kDa, up to about 1700 kDa, up to about 1600 kDa, up to about 1500 kDa, up to about 1400 kDa, up to about 1300 kDa, up to about 1200 kDa, up to about 1100 kDa, up to about 1000 kDa, up to about 950 kDa, up to about 900 kDa, up to about 850 kDa, up to about 800 kDa, up to about 750 kDa, up to about 700 kDa, up to about 650 kDa, up to about 600 kDa, up to about 550 kDa, up to about 500 kDa, up to about 450 kDa, up to about 400 kDa, up to about 350 kDa, up to about 300 kDa, up to about 250 kDa, up to about 200 kDa, up to about 150 kDa, up to about 100 kDa, up to about 50 kDa).

It is considered that the HAMA can have a molecular weight ranging from any of the minimum values described above to any of the maximum values described above. For example, in some aspects, the HAMA can have a molecular weight of from about 50 kDa to about 2000 kDa (e.g., from about 100 kDa to about 1900 kDa, from about 150 kDa to about 1800 kDa, from about 200 kDa to about 1700 kDa, from about 250 kDa to about 1600 kDa, from about 300 kDa to about 1500 kDa, from about 350 kDa to about 1400 kDa, from about 400 kDa to about 1300 kDa, from about 450 kDa to about 1200 kDa, from about 500 kDa to about 1100 kDa, from about 550 kDa to about 1000 kDa, from about 600 kDa to about 950 kDa, from about 650 kDa to about 900 kDa, from about 700 kDa to about 850 kDa, from about 750 kDa to about 800 kDa, from about 50 kDa to about 800 kDa, from about 100 kDa to about 750 kDa, from about 150 kDa to about 700 kDa, from about 200 kDa to about 650 kDa, from about 250 kDa to about 600 kDa, from about 300 kDa to about 550 kDa, from about 350 kDa to about 500 kDa, from about 400 kDa to about 450 kDa, from about 750 kDa to about 2000 kDa, from about 800 kDa to about 1900 kDa, from about 850 kDa to about 1800 kDa, from about 900 kDa to about 1700 kDa, from about 950 kDa to about 1600 kDa, from about 1000 kDa to about 1500 kDa, from about 1100 kDa to about 1400 kDa, from about 1200 kDa to about 1300 kDa).

In some aspects, the HA-Cat can have a molecular weight of at least about 50 kDa (e.g., at least about 100 kDa, at least about 150 kDa, at least about 200 kDa, at least about 250 kDa, at least about 300 kDa, at least about 350 kDa, at least about 400 kDa, at least about 450 kDa, at least about 500 kDa, at least about 550 kDa, at least about 600 kDa, at least about 650 kDa, at least about 700 kDa, at least about 750 kDa, at least about 800 kDa, at least about 850 kDa, at least about 900 kDa, at least about 950 kDa, at least about 1000 kDa, at least about 1100 kDa, at least about 1200 kDa, at least about 1300 kDa, at least about 1400 kDa, at least about 1500 kDa, at least about 1600 kDa, at least about 1700 kDa, at least about 1800 kDa, at least about 1900 kDa, at least about 2000 kDa). In some aspects, the HA-Cat can have a molecular weight of up to about 2000 kDa (e.g., up to about 1900 kDa, up to about 1800 kDa, up to about 1700 kDa, up to about 1600 kDa, up to about 1500 kDa, up to about 1400 kDa, up to about 1300 kDa, up to about 1200 kDa, up to about 1100 kDa, up to about 1000 kDa, up to about 950 kDa, up to about 900 kDa, up to about 850 kDa, up to about 800 kDa, up to about 750 kDa, up to about 700 kDa, up to about 650 kDa, up to about 600 kDa, up to about 550 kDa, up to about 500 kDa, up to about 450 kDa, up to about 400 kDa, up to about 350 kDa, up to about 300 kDa, up to about 250 kDa, up to about 200 kDa, up to about 150 kDa, up to about 100 kDa, up to about 50 kDa).

It is considered that the HA-Cat can have a molecular weight ranging from any of the minimum values described above to any of the maximum values described above. For example, in some aspects, the HA-Cat can have a molecular weight of from about 50 kDa to about 2000 kDa (e.g., from about 100 kDa to about 1900 kDa, from about 150 kDa to about 1800 kDa, from about 200 kDa to about 1700 kDa, from about 250 kDa to about 1600 kDa, from about 300 kDa to about 1500 kDa, from about 350 kDa to about 1400 kDa, from about 400 kDa to about 1300 kDa, from about 450 kDa to about 1200 kDa, from about 500 kDa to about 1100 kDa, from about 550 kDa to about 1000 kDa, from about 600 kDa to about 950 kDa, from about 650 kDa to about 900 kDa, from about 700 kDa to about 850 kDa, from about 750 kDa to about 800 kDa, from about 50 kDa to about 800 kDa, from about 100 kDa to about 750 kDa, from about 150 kDa to about 700 kDa, from about 200 kDa to about 650 kDa, from about 250 kDa to about 600 kDa, from about 300 kDa to about 550 kDa, from about 350 kDa to about 500 kDa, from about 400 kDa to about 450 kDa, from about 750 kDa to about 2000 kDa, from about 800 kDa to about 1900 kDa, from about 850 kDa to about 1800 kDa, from about 900 kDa to about 1700 kDa, from about 950 kDa to about 1600 kDa, from about 1000 kDa to about 1500 kDa, from about 1100 kDa to about 1400 kDa, from about 1200 kDa to about 1300 kDa).

In some aspects, the cell scaffold can further include a crosslinker including 2-hydroxy-4'-(2-hydroxyethoxy)-2-methylpropiophenone (NHS) and/or thiolated polyethylene glycol (PEG).

In some aspects, the crosslinker can include up to about 1 wt % 2 NHS (e.g., up to about 0.95 wt %, up to about 0.9 wt %, up to about 0.85 wt %, up to about 0.8 wt %, up to about 0.75 wt %, up to about 0.7 wt %, up to about 0.65 wt %, up to about 0.6 wt %, up to about 0.55 wt %, up to about 0.5 wt %, up to about 0.45 wt %, up to about 0.4 wt %, up to about 0.35 wt %, up to about 0.3 wt %, up to about 0.25 wt %, up to about 0.2 wt %, up to about 0.15 wt %, up to about 0.1 wt %, up to about 0.05 wt %, about 0 wt %). In some aspects, the crosslinker can include greater than 0 wt % NHS (e.g., greater than about 0.05 wt %, greater than about 0.1 wt %, greater than about 0.15 wt %, greater than about 0.2 wt %, greater than about 0.25 wt %, greater than about 0.3 wt %, greater than about 0.35 wt %, greater than about 0.4 wt %, greater than about 0.45 wt %, greater than about 0.5 wt %, greater than about 0.55 wt %, greater than about 0.6 wt %, greater than about 0.65 wt %, greater than about 0.7 wt %, greater than about 0.75 wt %, greater than about 0.8 wt %, greater than about 0.85 wt %, greater than about 0.9 wt %, greater than about 0.95 wt %, greater than about 1 wt %).

It is considered that the crosslinker can include an amount of NHS ranging from any of the minimum values described above to any of the maximum values described above. For example, in some aspects, the crosslinker can include from 0 wt % to about 1 wt % NHS (e.g., from about 0.05 wt % to about 0.95 wt %, from about 0.1 wt % to about 0.9 wt %, from about 0.15 wt % to about 0.85 wt %, from about 0.2 wt % to about 0.8 wt %, from about 0.25 wt % to about 0.75 wt %, from about 0.3 wt % to about 0.7 wt %, from about 0.35 wt % to about 0.65 wt %, from about 0.4 wt % to about 0.6 wt %, from about 0.45 wt % to about 0.55 wt %, from 0 wt % to about 0.5 wt %, from about 0.05 wt % to about 0.45 wt %, from about 0.1 wt % to about 0.4 wt %, from about 0.15 wt % to about 0.35 wt %, from about 0.2 wt % to about 0.3 wt %, from about 0.5 wt % to about 1 wt %, from about 0.55 wt % to about 0.95 wt %, from about 0.6 wt % to about 0.9 wt %, from about 0.65 wt % to about 0.85 wt %, from about 0.7 wt % to about 0.8 wt %).

In some aspects, the crosslinker can include up to about 2 wt % thiolated PEG (e.g., up to about 1.9 wt %, up to about 1.8 wt %, up to about 1.7 wt %, up to about 1.6 wt %, up to about 1.5 wt %, up to about 1.4 wt %, up to about 1.3 wt %, up to about 1.2 wt %, up to about 1.1 wt %, up to about 1 wt %, up to about 0.9 wt %, up to about 0.8 wt %, up to about 0.7 wt %, up to about 0.6 wt %, up to about 0.5 wt %, up to about 0.4 wt %, up to about 0.3 wt %, up to about 0.2 wt %, up to about 0.1 wt %, 0 wt %). In some aspects, the crosslinker can include greater than 0 wt % thiolated PEG (e.g., greater than about 0.1 wt %, greater than about 0.2 wt %, greater than about 0.3 wt %, greater than about 0.4 wt %, greater than about 0.5 wt %, greater than about 0.6 wt %, greater than about 0.7 wt %, greater than about 0.8 wt %, greater than about 0.9 wt %, greater than about 1 wt %, greater than about 1.1 wt %, greater than about 1.2 wt %, greater than about 1.3 wt %, greater than about 1.4 wt %, greater than about 1.5 wt %, greater than about 1.6 wt %, greater than about 1.7 wt %, greater than about 1.8 wt %, greater than about 1.9 wt %, greater than about 2 wt %).

It is considered that the crosslinker can include an amount of thiolated PEG ranging from any of the minimum values described above to any of the maximum values described above. For example, in some aspects, the crosslinker can include from 0 wt % to about 2 wt % thiolated PEG (e.g., from about 0.1 wt % to about 1.9 wt %, from about 0.2 wt % to about 1.8 wt %, from about 0.3 wt % to about 1.7 wt %, from about 0.4 wt % to about 1.6 wt %, from about 0.5 wt % to about 1.5 wt %, from about 0.6 wt % to about 1.4 wt %, from about 0.7 wt % to about 1.3 wt %, from about 0.8 wt % to about 1.2 wt %, from about 0.9 wt % to about 1.1 wt %, from 0 wt % to about 1 wt %, from about 0.1 wt % to about 0.9 wt %, from about 0.2 wt % to about 0.8 wt %, from about 0.3 wt % to about 0.7 wt %, from about 0.4 wt % to about 0.6 wt %, from about 1 wt % to about 2 wt %, from about 1.1 wt % to about 1.9 wt %, from about 1.2 wt % to about 1.8 wt %, from about 1.3 wt % to about 1.7 wt %, from about 1.4 wt % to about 1.6 wt %).

In some aspects, the cell scaffold can include at least about 5 mM $Fe^{3+}$ (e.g., at least about 5.5 mM, at least about 6 mM, at least about 6.5 mM, at least about 7 mM, at least about 7.5 mM, at least about 8 mM, at least about 8.5 mM, at least about 9 mM, at least about 9.5 mM, at least about 10 mM, at least about 10.5 mM, at least about 11 mM, at least about 11.5 mM, at least about 12 mM, at least about 12.5 mM, at least about 13 mM, at least about 13.5 mM, at least about 14 mM, at least about 14.5 mM, at least about 15 mM). In some aspects, the cell scaffold can include up to about 15 mM $Fe^{3+}$ (e.g., up to about 14.5 mM, up to about 14 mM, up to about 13.5 mM, up to about 13 mM, up to about 12.5 mM, up to about 12 mM, up to about 11.5 mM, up to about 11 mM, up to about 10.5 mM, up to about 10 mM, up to about 9.5 mM, up to about 9 mM, up to about 8.5 mM, up to about 8 mM, up to about 7.5 mM, up to about 7 mM, up to about 6.5 mM, up to about 6 mM, up to about 5.5 mM, up to about 5 mM).

It is considered that the cell scaffold can include an amount of $Fe^{3+}$ ranging from any of the minimum values described above to any of the maximum values described above. For example, in some aspects, the cell scaffold can include from about 5 mM to about 15 mM $Fe^{3+}$ (e.g., from about 5.5 mM to about 14.5 mM, from about 6 mM to about 14 mM, from about 6.5 mM to about 13.5 mM, from about 7 mM to about 13 mM, from about 7.5 mM to about 12.5 mM, from about 8 mM to about 12 mM, from about 8.5 mM to about 11.5 mM, from about 9 mM to about 11 mM, from about 9.5 mM to about 10.5 mM, from about 5 mM to about 10 mM, from about 5.5 mM to about 9.5 mM, from about 6 mM to about 9 mM, from about 6.5 mM to about 8.5 mM, from about 7 mM to about 8 mM).

In some aspects, the cell scaffold can have a damping factor (tan δ) of at least about 0.03 (e.g., at least about 0.04, at least about 0.05, at least about 0.06, at least about 0.07, at least about 0.08, at least about 0.09, at least about 0.1, at least about 0.11, at least about 0.12, at least about 0.13, at least about 0.14, at least about 0.15, at least about 0.16, at least about 0.17, at least about 0.18, at least about 0.19, at least about 0.2, at least about 0.21, at least about 0.22, at least about 0.23, at least about 0.24, at least about 0.25, at least about 0.26, at least about 0.27, at least about 0.28, at least about 0.29, at least about 0.3). In some aspects, the cell scaffold can have a damping factor (tan 8) of up to about 0.3 (e.g., up to about 0.29, up to about 0.28, up to about 0.27, up to about 0.26, up to about 0.25, up to about 0.24, up to about 0.23, up to about 0.22, up to about 0.21, up to about 0.2, up to about 0.19, up to about 0.18, up to about 0.17, up to about 0.16, up to about 0.15, up to about 0.14, up to about 0.13, up to about 0.12, up to about 0.11, up to about 0.1, up to about 0.09, up to about 0.08, up to about 0.07, up to about 0.06, up to about 0.05, up to about 0.04, up to about 0.03).

It is considered that the cell scaffold can have a damping factor (tan 8) ranging from any of the minimum values described above to any of the maximum values described above. For example, in some aspects, the cell scaffold can have a damping factor (tan 8) of from about 0.03 to about 0.3 (e.g., from about 0.04 to about 0.29, from about 0.05 to about 0.28, from about 0.06 to about 0.27, from about 0.07 to about 0.26, from about 0.08 to about 0.25, from about 0.09 to about 0.24, from about 0.1 to about 0.23, from about 0.11 to about 0.22, from about 0.12 to about 0.21, from about 0.13 to about 0.2, from about 0.14 to about 0.19, from about 0.15 to about 0.18, from about 0.16 to about 0.17, from about 0.03 to about 0.17, from about 0.04 to about 0.16, from about 0.05 to about 0.15, from about 0.06 to about 0.14, from about 0.07 to about 0.13, from about 0.08 to about 0.12, from about 0.09 to about 0.11, from about 0.16 to about 0.3, from about 0.17 to about 0.29, from about 0.18 to about 0.28, from about 0.19 to about 0.27, from about 0.2 to about 0.26, from about 0.21 to about 0.25, from about 0.22 to about 0.24).

In some aspects, the cell scaffold can have a compression modulus (E) of at least about 250 Pa (e.g., up to about 300 Pa, up to about 350 Pa, up to about 400 Pa, up to about 450 Pa, up to about 500 Pa, up to about 600 Pa, up to about 700 Pa, up to about 800 Pa, up to about 900 Pa, up to about 1000 Pa, up to about 1200 Pa, up to about 1400 Pa, up to about 1600 Pa, up to about 1800 Pa, up to about 2000 Pa, up to about 2200 Pa, up to about 2400 Pa, up to about 2600 Pa, up to about 2800 Pa, up to about 3000 Pa, up to about 3500 Pa, up to about 4000 Pa, up to about 4500 Pa, up to about 5000 Pa, up to about 5500 Pa, up to about 6000 Pa, up to about 6500 Pa, up to about 7000 Pa, up to about 7500 Pa, up to about 8000 Pa, up to about 8500 Pa, up to about 9000 Pa, up to about 9500 Pa, up to about 10,000 Pa). In some aspects, the cell scaffold can have a compression modulus (E) of up to about 10,000 Pa (e.g., up to about 9500 Pa, up to about 9000 Pa, up to about 8500 Pa, up to about 8000 Pa, up to about 7500 Pa, up to about 7000 Pa, up to about 6500 Pa, up to about 6000 Pa, up to about 5500 Pa, up to about 5000 Pa, up to about 4500 Pa, up to about 4000 Pa, up to about 3500 Pa, up to about 3000 Pa, up to about 2800 Pa, up to about 2600 Pa, up to about 2400 Pa, up to about 2200 Pa, up to about 2000 Pa, up to about 1800 Pa, up to about 1600 Pa, up to about 1400 Pa, up to about 1200 Pa, up to about 1000 Pa, up to about 900 Pa, up to about 800 Pa, up to about 700 Pa, up to about 600 Pa, up to about 500 Pa, up to about 450 Pa, up to about 400 Pa, up to about 350 Pa, up to about 300 Pa, up to about 250 Pa).

It is considered that the cell scaffold can have a compression modulus (E) ranging from any of the minimum values described above to any of the maximum values described above. For example, in some aspects, the cell scaffold can have a compression modulus (E) of from about 250 Pa to about 10,000 Pa (e.g., from about 300 Pa to about 9500 Pa, from about 350 Pa to about 9000 Pa, from about 400 Pa to about 8500 Pa, from about 450 Pa to about 8000 Pa, from about 500 Pa to about 7500 Pa, from about 600 Pa to about 7000 Pa, from about 700 Pa to about 6500 Pa, from about 800 Pa to about 6000 Pa, from about 900 Pa to about 5500 Pa, from about 1000 Pa to about 5000 Pa, from about 1200 Pa to about 4500 Pa, from about 1400 Pa to about 4000 Pa, from about 1600 Pa to about 3500 Pa, from about 1800 Pa to about 3000 Pa, from about 2000 Pa to about 2800 Pa, from about 2200 Pa to about 2600 Pa, from about 250 Pa to about 2400 Pa, from about 300 Pa to about 2200 Pa, from about 350 Pa to about 2000 Pa, from about 400 Pa to about 1800 Pa, from about 450 Pa to about 1600 Pa, from about 500 Pa to about 1400 Pa, from about 600 Pa to about 1200 Pa, from about 700 Pa to about 1000 Pa, from about 800 Pa to about 900 Pa, from about 2200 Pa to about 10,000 Pa, from about 2400 Pa to about 9500 Pa, from about 2600 Pa to about 9000 Pa, from about 2800 Pa to about 8500 Pa, from about 3000 Pa to about 8000 Pa, from about 3500 Pa to about 7500 Pa, from about 4000 Pa to about 7000 Pa, from about 4500 Pa to about 6500 Pa, from about 5000 Pa to about 6000 Pa).

In some aspects, the cell scaffold can have a stress relaxation time of at least about 10 seconds (e.g., at least about 20 seconds, at least about 30 seconds, at least about 60 seconds, at least about 90 seconds, at least about 120 seconds, at least about 150 seconds, at least about 180 seconds, at least about 210 seconds, at least about 240 seconds, at least about 270 seconds, at least about 300 seconds, at least at least about 350 seconds, at least about 400 seconds, at least about 450 seconds, at least about 500 seconds, at least about 550 seconds, at least about 600 seconds, at least about 650 seconds, at least about 700 seconds, at least about 750 seconds, at least about 800 seconds, at least about 850 seconds, at least about 900 seconds, at least about 950 seconds, at least about 1000 seconds). In some aspects, the cell scaffold can have a stress relaxation time of up to about 1000 seconds (e.g., up to about 950 seconds, up to about 900 seconds, up to about 850 seconds, up to about 800 seconds, up to about 750 seconds, up to about 700 seconds, up to about 650 seconds, up to about 600 seconds, up to about 550 seconds, up to about 500 seconds, up to about 450 seconds, up to about 400 seconds, up to about 350 seconds, up to about 300 seconds, up to about 270 seconds, up to about 240 seconds, up to about 210 seconds, up to about 180 seconds, up to about 150 seconds, up to about 120 seconds, up to about 90 seconds, up to about 60 seconds, up to about 30 seconds, up to about 20 seconds, up to about 10 seconds).

It is considered that the cell scaffold can have a stress relaxation time ranging from any of the minimum values described above to any of the maximum values described above. For example, in some aspects, the cell scaffold can have a stress relaxation time of from about 10 seconds to about 1000 seconds (e.g., from about 20 seconds to about 950 seconds, from about 30 seconds to about 900 seconds, from about 60 seconds to about 850 seconds, from about 90 seconds to about 800 seconds, from about 120 seconds to about 750 seconds, from about 150 seconds to about 700 seconds, from about 180 seconds to about 650 seconds, from about 210 seconds to about 600 seconds, from about 240 seconds to about 550 seconds, from about 270 seconds to about 500 seconds, from about 300 seconds to about 450 seconds, from about 350 seconds to about 400 seconds, from about 10 seconds to about 400 seconds, from about 20 seconds to about 350 seconds, from about 30 seconds to about 300 seconds, from about 60 seconds to about 270 seconds, from about 90 seconds to about 240 seconds, from about 120 seconds to about 210 seconds, from about 150 seconds to about 180 seconds, from about 350 seconds to about 1000 seconds, from about 400 seconds to about 950 seconds, from about 450 seconds to about 900 seconds, from about 500 seconds to about 850 seconds, from about 550 seconds to about 800 seconds, from about 600 seconds to about 750 seconds, from about 650 seconds to about 700 seconds).

In some aspects, the spinal cord spheroid or organoid or a fragment thereof may be human. In some aspects, the spinal cord spheroid or organoid or a fragment thereof can be formed by culturing induced pluripotent stem cells (iP-SCs) on the cell scaffold.

In some aspects, the one or more ventral markers can include SOX2, FOXA2, LHX3, NKX2.2, and/or OLIG2; the one or more dorsal markers can include PAX7, LHX3, LMX1, LHX9, and/or BRN3; and the one or more interneuron markers can include DBX1, DBX2, and or PAX6.

In some aspects, compared to a reference spinal cord spheroid or organoid or fragment thereof not cultured on the cell scaffold, the spinal cord spheroid or organoid or fragment thereof can include at least about 1.5-fold greater expression of the one or more ventral markers (e.g., at least about 1.6-fold greater, at least about 1.7-fold greater, at least about 1.8-fold greater, at least about 1.9-fold greater, at least about 2-fold greater, at least about 2.1-fold greater, at least about 2.2-fold greater, at least about 2.3-fold greater, at least about 2.4-fold greater, at least about 2.5-fold greater).

In some aspects, compared to a reference spinal cord spheroid or organoid or fragment thereof not cultured on the cell scaffold, the spinal cord spheroid or organoid or fragment thereof can include at least about 2-fold greater expression of the one or more dorsal markers (e.g., at least about 2.1-fold greater, at least about 2.2-fold greater, at least about 2.3-fold greater, at least about 2.4-fold greater, at least about 2.5-fold greater, at least about 2.6-fold greater, at least about 2.7-fold greater, at least about 2.8-fold greater, at least about 2.9-fold greater, at least about 3-fold greater, at least about 3.1-fold greater, at least about 3.2-fold greater, at least about 3.3-fold greater, at least about 3.4-fold greater, at least about 3.5-fold greater, at least about 3.6-fold greater, at least about 3.7-fold greater, at least about 3.8-fold greater, at least about 3.9-fold greater, at least about 4-fold greater).

In some aspects, compared to a reference spinal cord spheroid or organoid or fragment thereof not cultured on the cell scaffold, the spinal cord spheroid or organoid or fragment thereof can include at least about 2-fold greater expression of the one or more interneuron markers (e.g., at least about 2.1-fold greater, at least about 2.2-fold greater, at least about 2.3-fold greater, at least about 2.4-fold greater, at least about 2.5-fold greater, at least about 2.6-fold greater, at least about 2.7-fold greater, at least about 2.8-fold greater, at least about 2.9-fold greater, at least about 3-fold greater).

In another aspect, provided is a blood-spinal cord barrier model including a spinal cord spheroid or organoid or a fragment thereof derived from any of the disclosed spinal cord models co-cultured with a blood vessel spheroid or organoid or a fragment thereof.

Methods

In one aspect, provided is a method of modeling a spinal cord, the method including culturing a plurality of induced pluripotent stem cells on a cell scaffold to form a spinal cord spheroid or organoid or a fragment thereof, the cell scaffold including methacrylated hyaluronic acid (HAMA) and dopamine-modified hyaluronic acid (HA-Cat); wherein the method causes the spinal cord spheroid or organoid or a fragment thereof to express one or more ventral markers, dorsal markers, and/or interneuron markers.

In another aspect, provided is a method of modeling a blood-spinal cord barrier, the method including: a) culturing a plurality of induced pluripotent stem cells on a cell scaffold to form a spinal cord spheroid or organoid or a fragment thereof, the cell scaffold including methacrylated hyaluronic acid (HAMA) and dopamine-modified hyaluronic acid (HA-Cat); and b) co-culturing the spinal cord spheroid or organoid or a fragment thereof with a blood vessel spheroid or organoid or a fragment thereof; wherein step a) causes the spinal cord spheroid or organoid or a fragment thereof to express one or more ventral markers, dorsal markers, and/or interneuron markers.

Two example protocols for culturing the induced pluripotent stem cells to form the spinal cord spheroid or organoid or fragment thereof are described below. In one example, at day 0, the single induced pluripotent stem cells (i.e., iPSCs or hiPSCS) are seeded in 100 μL of DMEM/F12 plus N2B27 medium with 10 μM Y-27632 in each well of a U-bottom low attachment 96-well plate at a density of 15,000 cells/well for hiPSC self-aggregation. At day 1, the cells are fed with N2B27 medium containing 10 μM Y-27632, 4 μM CHIR 99021, and 0.5 μM LDN193189. For ventral spinal cord organoid differentiation, RA activators (retinoic acid) and SHH activators (purmorphamine) are added to the culture media at various stages for promoting ventral spinal cord patterning. At day 3, the self-assembled spheroids are transferred into hydrogels, which are layered on top and beneath the spheroids, and the neural induction medium containing 1 μM RA is added for generating ventral patterning. At day 10, the N2B27 medium is changed to 1uM retinoic acid and 1 μM Purmorphamine. The medium is changed every other day. On day 18 and onwards, the medium is changed to N2B27 media supplemented with 10 ng/ml BDNF.

In another example, dissociated small clumps of induced pluripotent stem cells are seeded into the U-bottom low attachment 96-well plates at density of 15,000 cells/well for hiPSC self-aggregation with 100 μL neural induction medium with 10 μM Y-27632. After two days culture, the medium is changed to N2B27 medium with 10 μM SB431542 and 2 μM CHIR99021 for 3 days with daily medium change. At day 3, the self-assembled spheroids are transferred into hydrogels. At day 5, the medium is changed to N2B27 with 20 ng/mL bFGF. The spheroids are fed daily for four days and begin forming a neuroepithelial (NE) structure at the peripheral surface of the organoid. On day 9, the spheroids are cultured in NIM containing 0.1 μM RA without bFGF for 8 days, inducing neural plate morphogenesis in NEs to form the neural tube. The medium is changed every other day. For organoid maturation, the spheroids are grown in a 1:1 mixture of DMEM/F-12 and neurobasal medium (Life Technologies, 21103-049; the medium contained 0.5% N2, 2% B27, 0.5% NEAA, 1% P/S, 0.1% β-mercaptoethanol, 1% GlutaMAX, and 0.1 μM RA. The medium is changed every 3-5 days.

In some aspects, the induced pluripotent stem cells can include healthy cells. In other aspects, the induced pluripotent stem cells can include diseased or abnormal cells. For example, in some such aspects, the induced pluripotent stem cells can be derived from a subject having a neurodevelopmental disorder, a neurodegenerative disease or disorder, a neurological disease or disorder, or a cancer (e.g., a brain cancer or spinal cancer).

In some aspects, the blood vessel spheroid or organoid or a fragment thereof can include healthy cells. In other aspects, the blood vessel spheroid or organoid or fragment thereof can include diseased or abnormal cells. For example, in some such aspects, the blood vessel spheroid or organoid or fragment thereof can be derived from a subject having an aneurysm or a vascular cancer (e.g., angiosarcoma).

In some aspects, the method can produce any of the disclosed spinal cord models or blood-spinal cord barrier models described above.

In yet another aspect, provided is a method of screening a therapeutic agent, the method including: a) culturing a plurality of induced pluripotent stem cells on a cell scaffold to form a spinal cord spheroid or organoid or a fragment thereof, the cell scaffold including methacrylated hyaluronic acid (HAMA) and dopamine-modified hyaluronic acid (HA-Cat); and b) administering the therapeutic agent to the spinal cord spheroid or organoid or fragment thereof.

In yet still another aspect, provided is a method of screening a therapeutic agent, the method including: a) culturing a plurality of induced pluripotent stem cells on a cell scaffold to form a spinal cord spheroid or organoid or a fragment thereof, the cell scaffold including methacrylated hyaluronic acid (HAMA) and dopamine-modified hyaluronic acid (HA-Cat); b) culturing a plurality of induced pluripotent stem cells on the cell scaffold to form a spinal cord spheroid or organoid or a fragment thereof; c) co-culturing the spinal cord spheroid or organoid or a fragment thereof with a blood vessel spheroid or organoid or a fragment thereof; and d) administering the therapeutic agent to the spinal cord spheroid or organoid or fragment thereof and/or the blood vessel spheroid or organoid or a fragment thereof.

In some aspects, the induced pluripotent stem cells can include healthy cells. In other aspects, the induced pluripotent stem cells can include diseased or abnormal cells. For example, in some such aspects, the induced pluripotent stem cells can be derived from a subject having a neurodevelopmental disorder, a neurodegenerative disease or disorder, a neurological disease or disorder, or a cancer (e.g., a brain cancer or spinal cancer).

In some aspects, the blood vessel spheroid or organoid or a fragment thereof can include healthy cells. In other aspects, the blood vessel spheroid or organoid or fragment thereof can include diseased or abnormal cells. For example, in some such aspects, the blood vessel spheroid or organoid or fragment thereof can be derived from a subject having an aneurysm or a vascular cancer (e.g., angiosarcoma).

In some aspects, the method can use any of the spinal cord models or blood-spinal cord barrier models described above.

In some aspects, the therapeutic agent can be targeted to treat and/or prevent a neurodevelopmental disorder, a neurodegenerative disease or disorder, a neurological disease or disorder, brain cancer, or spinal cancer.

EXAMPLES

Example 1: Viscoelasticity of Hyaluronic Acid Hydrogels Regulates Human Pluripotent Stem Cell-derived Spinal Cord Organoid Patterning and Vascularization The 3D ventral spinal cord organoids have been generated using cell cycle inhibitor and recapitulated spinal neurogenesis as well as rostro-caudal patterns for modeling motor neuron disease [9]. To promote spinal cord patterning, using extracellular matrix (ECM) or scaffolds may provide a 3D signaling network to better pattern spinal cord organoids [10]. Additionally, inclusion of vital structure such as blood spinal cord barrier (BSCB) in the organoid is important for studying the dysfunction of spinal cord [11]. The BSCB serves as an interface responsible for facilitating the transport of nutrients between the bloodstream and the spinal cord [12]. Due to the analogous structure to the blood brain barrier, the endothelial cells are the most important components for spinal cord vascularization. Additionally, isogenic human blood vessel organoids (hBVOs) possess the capability to generate vascular structures and can be used to co-culture with human spinal cord organoids (hSCOs) to include BSCB structure in the organoids, through spheroid fusion and assembly as shown in previous studies [13, 14].

3D ECMs have a variety of effects on cellular process due to different characteristics. Elasticity or stiffness, nanotopography, and chemical functionalities of ECMs all have an influence on cell spreading, proliferation, migration, differentiation, and organoid formation [15-17]. Well-engineered ECMs can provide a proper microenvironment to regulate cellular behaviors including tissue regeneration due to specific biochemical and biophysical cues [18, 19]. In particular, the patterning of tissues or organoids can be tailored by 3D ECMs. 3D scaffold biomaterials especially hydrogels can be fabricated to mimic static mechanical properties of biological tissues and ECMs in the human body [20, 21]. Besides spatial mechanical properties, the viscoelasticity, or temporal (time-dependent) properties of hydrogels provides in-time cues for tissues/organoids to sense [22, 23] and dynamic stimulation to respond. The viscoelasticity of ECMs is a temporal parameter of the materials which can apply dynamic stimulation to the cells surrounded by ECMs. By regulating viscoelasticity in addition to mechanical properties such as the Young's modulus, ECMs provide both spatial and temporal factors for neural tissue morphogenesis [24]. Recently, the viscoelasticity of biomaterials (e.g., alginate) has been assessed to regulate cell proliferation, migration, and spreading [25, 26]. In addition, the effects of ECM viscoelasticity on the generation of embryoid body-like structure from hiPSCs were revealed [22]. Using alginate hydrogels with arginine-glycine-aspartate (RGD) ligands, the hiPSC morphogenesis in 3D culture showed that RGD density and stress relaxation time influenced cell viability, proliferation, apicobasal polarization, and lumen formation [22]. Nevertheless, the influence of hydrogel viscoelasticity on the cell behaviors is at the nascent stage, and the effect on the spinal cord organoid patterning has not yet been investigated.

In the human body, the major components of ECMs in the central nervous system are hyaluronans [27, 28]. Hyaluronic acid (HA) in the tissue fluid helps the tissue resist osmotic compression and absorb compressive force [29, 30]. Additionally, the network of HA is assembled by the existence of proteoglycans. The brain and spinal cord ECMs lack the fibrous components, such as collagens [31, 32]. In the brain, the entanglement of HA network is stabilized by specific connection between tenascins and proteoglycans [33]. Furthermore, HA can be used for wound healing, tissue maintenance, and inflammation [34-36]. The specific molecular weight of HA in different body parts could promote tissue remodeling and homeostasis [37, 38]. For example, HA has a remarkable hydration capacity, and lack of HA causes reduced extracellular space volume in the brain [39]. In the brain, the entangled network of HA needs to be stabilized through linkage with proteins and chondroitin sulfate proteoglycans [33, 40]. Therefore, HA-based ECMs can be designed with various modifications and compositions to provide specific biochemical and biomechanical properties [41-44].

Hence, this study fabricated different HA-based hydrogels for the generation and recapitulation of the patterning of spinal cord organoids. The static properties such as the stiffness of the hydrogels are important for regulating the behaviors of hiPSCs. However, dynamic properties, or time-dependent feature of the polymer also have important effects on the morphogenesis and lineage-specific differentiation of hiPSCs. Therefore, HA hydrogels with different stiffness and viscoelasticity were fabricated and characterized, based on covalent bond crosslinked methacrylated HA (HAMA). Then, hiPSCs were seeded into different hydrogels and induced for hSCO differentiation and patterning. hBVOs and hSCOs from different hydrogels were cocultured and characterized for vascularization of the organoids, which may lead to the generation of blood spinal cord barrier. Furthermore, dopamine modified HA (HA-Cat) with $Fc^{3+}$ coordinated crosslinked hydrogels were mixed with HAMA hydrogels to make dual network penetration (i.e., HAMA@HA-Cat) hydrogels. The dual network penetrated hydrogels also regulated hSCO patterning. Together, this study has significant implications on the role of viscoelastic properties of hydrogels in establishing human organoid model systems for disease modeling and drug screening.

Materials and Methods

Materials and reagents: The vendors and catalog numbers of key materials and reagents are provided: Sodium hyaluronate (HA-100k, HA-200k, HA-1M, Lifecore Biomedical, Inc), Dopamine hydrochloride (Sigma, H8502), methacrylic anhydride (Sigma, 276685), sodium hydroxide (Sigma, 221465), 1-ethyl-3-(-3-dimethylaminopropyl) carbodiimide hydrochloride (EDC, D1601), N-hydroxysuccinimide (Thermo Scientific Chemicals, 157270250), poly ethylene glycol (PEG)-dithiol (Creative PEGWorks, PLS-612), 2-Hydroxy-4'-(2-hydroxyethoxy)-2-methylpropiophenone (NHS) (Sigma, 410896), Rho-associated protein kinase (ROCK) inhibitor Y27632 (Sigma, Y0503), mTcSR Plus (STEMCELL Technologies Inc., 100-0276), LDN193189 hydrochloride (Sigma, SML0559), DMEM/F-12 (Gibco™, 12400024), B-27™ Supplement (50×) (Gibco™, 17504044), CHIR99021 (a Wnt signaling activator, Sigma, SML1046), retinoic acid (RA, Sigma), purmorphamine (a sonic hedgehog signaling activator, Sigma, SML0868), Recombinant human fibroblast growth factor (FGF)-basic (bFGF, Peprotech, 100-18C), N-2 Supplement (100×) (Gibco™, 17502048), Neurobasal™ Medium (Gibco™, 21103049), Human Endothelial Serum-free Medium (hESFM) (Gibco™, 11111044), β-mercaptoethanol (Gibco™, 21985023), MEM Non-Essential Amino Acids (NEAA) Solution (100×) (Gibco™, 11140050), Gluta-MAX™ Supplement (Gibco™, 35050061), Proteinase K (Research Products International Corp, P502200.1), LIVE/DEAD™ Viability/Cytotoxicity Kit for mammalian cells (Invitrogen™, L3224), N2B27 media: 50% of DMEM/F12 mix with 50% Neurobasal Medium supplemented with 0.5% N2, 2% B27, 0.5% NEAA, 1% Penicillin/Streptomycin (P/S), 0.1% β-mercaptocthanol, and 1% GlutaMAX, Brain-derived neurotrophic factor (BDNF, Peprotech, 450-02), and Growth factor-reduced Matrigel (Corning, 354230).

Synthesis and characterization of HAMA and HA-Cat: For HAMA synthesis, methacrylation of HA was performed by adding dropwise 1.1 mL of MA at 1% (v/v) to 100 mL of 1% (w/v) HA solution in phosphate buffered saline (PBS), pH 7.4, at 4° C., under magnetic stirring for 24 h. The pH of the solution was kept between 8 and 10 with the addition of 5 N NaOH, until no further pH changes were detected, which indicated that the reaction was complete. The solution was dialyzed for 4 days with a 12-14 kDa membrane in deionized water at 4° C. Then, HAMA was frozen and lyophilized. The obtained powder material was stored at -20° C. until further usc.

For catechol functionalization of HAMA, i.e., HA-Cat synthesis, HAMA was dissolved in 2-(N-Morpholino) cthanesulfonic acid (MES) buffer (pH=4.5). Next, 0.03 mol/L NHS, 0.03 mol/L EDC and 0.05 mg/mL dopamine were added to a bottle and stirred overnight to fully react. After synthesis, the derivatives of HA underwent dialysis in de-ionized water for three days to purify. Then the solutions were frozen and lyophilized. After synthesis, H1-NMR (Bruker spectrometers B600, FSU-NMR Facility) was performed to characterize modification after synthesis.

HAMA and HAMA@HA-Cat hydrogel fabrication and characterization:

Hydrogel fabrication: To obtain the covalently cross-linked HAMA gels, the HAMAs were photo-crosslinked with dithiol-PEG. A total of nine gels were synthesized. HAMA (three groups with molecular weight at 100k, 200k, and 1,000k) was dissolved at 1%, 0.5%, and 0.25% (w/w) in PBS, respectively. The mixed polymer precursor in PBS was incubated at 37° C. with 0.1% (w/v) of NHS and 0.5% thiolated PEG and then cured with Dymax light shields model 5000 EC flood (intensity: 225 mW/cm2) for 30 seconds.

For fabrication of the HAMA@HA-Cat hydrogels (@ means that the hydrogel is a dual penetration network), 1% wt HAMA (three groups: 100k, 200k, and 1,000k of molecular weight) and 1% wt HA-Cat (1,000k) were mixed at a ratio of 1:1. Then, the mixed polymer precursor in PBS was incubated at 37° C. with 0.1% (w/v) of NHS and 0.5% thiolated PEG and then cured with Dymax light shields model 5000 EC flood (intensity: 225 mW/cm2) for 30 seconds. After the crosslinking, 200 μL of 40 mM FeCl3 aqueous solution was added to the hydrogels. The bulk hydrogels were cut into granular hydrogels for better reaction with FeCl3 solution during HA-Cat crosslinking.

Characterization of hydrogels: The static elastic properties of the hydrogels were measured via compression tests performed on an ARES-G2 Rheometer using a parallel plate geometry (d=25 mm) (TA Instruments, New Castle, DE, USA) and strain rate of 0.0000667 s-1. Each gel composition was characterized with three specimens for at least three independent measurements.

Rheological characterization was also performed with an ARES-G2 Rheometer using the parallel plate geometry (d=25 mm, gap 0.5 mm). Oscillatory rheometry was conducted to measure the clastic and viscous modulus of the hydrogels. At first, parallel discs of 25 mm in diameter were placed on the rheometer and a 25 mm flat plate geometry was used to measure the samples across a strain sweep to find linear viscoelastic region (LVR) of the HAMA hydrogels with the parameter at 6.28 rad/s, 37° C. and within the range of strain at 0.1-100%. Then, the 0.5% strain was chosen for the frequency sweep to get the rheological properties of HAMA hydrogels. At least 3 samples (0.5 mm thick) for each gel composition were characterized.

The stress relaxation test was then performed in hydrogels. All samples were put between parallel discs of 25 mm in diameter and a gap of 1 mm. Next, the stress-relaxation behavior was quantified at 10% strain, with all tests lasting from 500 s to 3000 s for the samples to reach the plateau for the hydrogels. Then, the relaxation time data were regressed by Maxwell model to get the relaxation time (t).

The morphology of the hydrogels was examined using scanning electron microscopy (SEM). The HAMA hydrogels were freeze-dried in a lyophilizer (Labconco Corporation, Kansas City, MO, USA) for 2 days. Then, the samples were taken out carefully, fixed onto a SEM stage with carbon tape, and coated with a 10 nm gold layer to better reveal the hydrogel morphology. Observations were made using a FEI Helios G4 UC multi-technique dual beam (electron and Ga ion) Field Emission Scanning Electron Microscope (FE-SEM) (Thermo Fisher Scientific, Pittsburgh, PA) under low-vacuum conditions.

hiPSC 2D and 3D cultures for biocompatibility evaluation: Undifferentiated human iPSK3 cells (human foreskin fibroblasts reprogrammed with plasmid DNA encoding reprogramming factors OCT4, NANOG, SOX2, and LIN28) were maintained on Growth Factor-reduced Matrigel-coated surface in mTeSR serum-free medium as described in previous publications [13, 14]. Prior to hiPSC seeding, the sterile HAMA precursor solutions were added into the wells of tissue culture plates and then the solutions were cured under UV for 30s to form HAMA hydrogels. For 2D culture, the hiPSC suspension (~1×10$^5$ cells) was added at 100 µL into the wells of 96-well tissue culture plates coated with Matrigel (to ensure undifferentiated hiPSC attachment), on top of which was layered with different types of hydrogels. The cells were allowed to settle down into the hydrogels for 15 min. Then additional 100 µL of media were added to each well of a 96-well plate. For 3D culture, the hydrogels were fabricated in the wells of ultralow attachment (ULA) 96-well plates (to prevent cells from attaching to the surface of the culture plates). The dissociated hiPSCs were seeded into the hydrogels by placing two concentrated droplets (50 µL each) of cells into the hydrogels, for a final density of 1×10$^5$ cells per gel. After 5 min, additional 100 µL media were added to each well. The cultures were maintained for 7 days and the cells were characterized by DNA assay for proliferation and Live/Dead assay for viability [45, 46].

Human spinal cord organoid differentiation in hydrogels: Two hSCO differentiation protocols were evaluated before the experiments using hydrogels [47, 48]. After comparison, the ventral hSCO differentiation protocol was chosen for this study. Briefly, undifferentiated hiPSCs were dissociated by Accutase for 5-7 min. At day 0, the single cells were seeded in 100 µL of DMEM/F12 plus N2B27 medium with 10 µM Y-27632 in each well of a U-bottom low attachment 96-well plate at a density of 15,000 cells/well for hiPSC self-aggregation. At day 1, the cells were fed with N2B27 medium containing 10 µM Y-27632, 4 µM CHIR 99021, and 0.5 µM LDN193189. At day 3, the neural induction medium containing 1 µM RA was added for generating ventral patterning. The medium was changed every other day. At day 10, the spheroids were embedded into 15 µL concentrated Matrigel (1:3 dilution with neural induction medium) and incubated for one hour. Then, N2B27 media supplemented with 1 µM RA and 1 µM Purmorphamine were added to each well for neural patterning without disturbing Matrigel droplets. At day 14, the Matrigel-embedded organoids were transferred to the rocker [49, 50] or PBS Vertical Wheel bioreactor (PBS Biotech Inc., CA, USA) [51, 52] for further expansion and maturation. On day 18 and onwards, the medium was changed to N2B27 media supplemented with 10 ng/mL BDNF. To evaluate the influence of different types of hydrogels, single hiPSCs were seeded at a density at 15,000 cell/well into ULA 96-well plate. At day 3, the self-assembled spheroids were transferred into hydrogels, which were layered on top and beneath the spheroids, for further hSCO differentiation or co-culture with hBVOs.

The protocol for differentiating caudal hSCO: For the other hSCO differentiation protocol (i.e., hSCOB), dissociated small clumps of hiPSCs were seeding into the U-bottom low attachment 96-well plates at density of 15,000 cells/well for hiPSC self-aggregation with 100 µL neural induction medium with 10 µM Y-27632. After two days culture, the medium was changed to N2B27 medium with 10 µM SB431542 and 2 µM CHIR99021 for 3 days with daily medium change. At day 5, the medium was changed to N2B27 with 20 ng/mL bFGF. The spheroids were fed daily for four days and began forming a neuroepithelial (NE) structure at the peripheral surface of the organoid. On day 9, hSCOs were cultured in NIM containing 0.1 µM RA without bFGF for 8 days, inducing neural plate morphogenesis in NEs to form the neural tube. The medium was changed every other day. For organoid maturation, hSCOs were grown in a 1:1 mixture of DMEM/F-12 and neurobasal medium (Life Technologies, 21103-049; the medium contained 0.5% N2, 2% B27, 0.5% NEAA, 1% P/S, 0.1% β-mercaptoethanol, 1% GlutaMAX, and 0.1 µM RA. The medium was changed every 3-5 days.

Human blood vessel organoid differentiation: The hBVO generation was modified from previous publications [53, 54]. hiPSCs were seeded in the wells of ULA 96 well plate at a density at 10,000 cells/well in mTeSR plus supplemented with 10 M ROCK inhibitor Y-27632. To initiate differentiation at day 0, cells were treated with 6 µM CHIR99021 (Selleckchem) in BVO1 medium: DMEM/F12 supplemented with 2% B27, 0.5% NEAA, 1% P/S, 0.1% β-mercaptoethanol, and 1% GlutaMAX. The medium was changed every other day until day 6. At day 6, the medium was switched to BVO2 medium: hESFM supplemented with 20 ng/ml bFGF, 10 UM RA, and 2% B27. At day 9, the organoids were replated to tissue culture plates or continued to grow in hESFM with 2% B27 for long-term culture.

The vascular differentiation (vsc) protocol: For vascular differentiation of hiPSCs, Y27632 was added to the medium with cell density at 0.5×10$^6$ per well at day 0. Then, the Wnt activator CHIR99021 (12 µM, STEMCELL Technologies Inc.) was added to the culture medium at day 3. At day 5, 7, and 9, the media (DMEM/F12 with 2% B27) were changed to treat the cell aggregates with bone morphogenetic protein (BMP) 4 (Peprotech) (20 ng/ml), vascular endothelial growth factor (VEGF)-A (Peprotech) (20 ng/mL), and bFGF (20 ng/ml). At day 11, cells were switched to the medium containing VEGF-A (20 ng/ml), and bFGF (20 ng/ml), SB431542 (10 µM) to promote endothelial cell (EC) differentiation and suppress pericyte differentiation. At day 13, the cell aggregates were embedded in Matrigel and overlaid with differentiation medium containing 15% fetal bovine serum (FBS), 20 ng/mL VEGF-A, and 20 ng/ml FGF-2. Medium was changed every two or three days. At day 18, vascular networks were observed and analyzed. The derived cells were referred as iECs.

hSCO co-culture with hBVOs: Spheroid or organoid fusion methods were evaluated for hSCO vascularization by co-culturing with hBVOs. One 9-day hBVO and one 25-day hSCO were added to the same well of ULA 96-well plate and the organoid fusion occurred spontaneously. After a two-day fusion, the assembled organoid was embedded into Matrigel. Then the organoids were transferred to a low attachment 6-well plate on the rocker. For cell tracker labeling, culture media were removed, and CellTracker™ Red (1:1000 dilution, ThermoFisher Scientific, Waltham, MA, USA) solution was added. hBVOs were incubated with CellTracker™ Red solution at 37° C. for one hour. Then the staining solution was removed followed with washing. One CellTracker™ Red labeled hBVO and one hSCO were put next to each other in the same well of 96-well plate for 2 days. Finally, the assembly of the two organoids were imaged. All hSCOs from different HAMA hydrogels were extracted from hydrogels using blunt pipette tips, then they were co-cultured and assembled with hBVOs. The assembloids were characterized for the marker expression of both hSCOs and hBVOs.

Characterization of cell proliferation and biocompatibility in hydrogels: Cell proliferation was determined by DNA quantitation using Picogreen. The cells were harvested and lyscd with 0.1 mg/mL proteinase K (Fisher Scientific, Pittsburgh, PA) at 50° C. overnight. The lysates (100 µL) were mixed with 100 µL of 0.5% Picogreen (Molecular Probes, Eugene, OR) in a 96-well plate. The plate was incubated for 5 min in the dark and then read on a fluorescent plate reader with 485cx/528 cm (BioRad Laboratories, Hercules, CA). The biocompatibility of the hiPSCs in different hydrogels were evaluated using LIVE/DEAD™ Viability/Cytotoxicity Kit (Invitrogen™, Waltham, MA). The organoids were harvested and then dissociated to single cells by Accutase for 20-40 min. Then, a cell suspension at $1 \times 10^6$ cells/mL was prepared. Next, 6 µL of 50 µM Calcein AM and 2 µL of 2 mM ethidium homodimer-1 (EthD-1) were added to each mL of cell suspension. The mixture of dye and cells was incubated at room temperature (RT) for 15 min. The stained cells were acquired with BD FACSCanto™ II flow cytometer (Becton Dickinson) and analyzed by FlowJo software. The cell only, live only, dead only, and live and dead samples were prepared for two-color flow cytometry compensation.

Histology sectioning and immunohistochemistry: The hSCOs were harvested and placed into 1.5 mL centrifuge tubes and fixed with 10% neutral buffered formalin for 24 hours. Then, the samples were dehydrated by series of ethanol solutions. Briefly, hSCOs were sequentially transferred to 70%, 75%, 80%, and 90% ethanol for 15 min each.

Next, the samples were put into 95% ethanol for 60 min twice. Lastly, samples were submerged in 100% ethanol for 60 min twice. After dehydration, hSCOs were transferred into xylene for two 30-60 min intervals. Samples were incubated with 60° C. paraffin for 60 min twice and embedded with paraffin at ideal position during overnight cooling. After embedding in paraffin, the samples were sectioned by microtome at 6 µm for each slice. The slice was transferred to warm water and then dried on glass slides. Then, the sections were deparaffinized by immersing in Xylene for 3 min twice. Next, the slides were immersed into 100% ethanol for 3 min twice, 95% ethanol for 3 min, 70% ethanol for 3 min and then put under running cold tap water to rinse. The wet sections were transferred into 95° C. Sodium Citrate Buffer (10 mM Sodium Citrate, 0.05% Tween 20, pH 6.0) for 30 min and then washed under running cold tap water for 10 min. Immunocytochemistry analysis of hSCO markers were performed on the sections. Yes-associated protein (YAP) staining was also performed on the sections using a similar procedure to immunocytochemistry.

Immunocytochemistry of organoids: The hSCOs were directly replated to Matrigel (1:50) coated tissue culture plate. hBVOs were first dissociated by Accutase for 40 min, and then replated to Matrigel (1:50) coated tissue culture plate. Then, after a 3-day growth, both samples were fixed with 4% paraformaldehyde and permeabilized with cold methanol for staining intracellular markers. The samples were then blocked with 5% fetal bovine serum (FBS) and incubated with various mouse or rabbit primary antibodies (TABLE 1). Next, secondary antibodies were added in staining buffer (2% FBS in PBS). The cells were washed three times each for 5 min. The samples were then stained using Hoechst 33342 (ThermoFisher, 1:2,000) to label cell nuclei and afterwards washed with PBS overnight. Images of stained organoids were captured using a fluorescent microscope (Zeiss Axio Observer) or a Zeiss LSM 880 confocal microscope.

TABLE 1

| A list of antibodies for target markers. | | | | |
| --- | --- | --- | --- | --- |
| Cells | Primary Antibody | Origin/Isotype | Supplier/Cat# | Dilution |
| Neural cells | CHX10 | Mouse monoclonal IgG2a | Santa Cruz, sc-365519 | 1:100 |
| | LHX3 | Mouse monoclonal IgG2a | Santa Cruz, sc-293411 | 1:100 |
| | SOX2 | Mouse monoclonal IgG1 | Santa Cruz, sc-365823 | 1:100 |
| | NKX6.1 | Mouse monoclonal IgG2a | Santa Cruz, sc-130385 | 1:100 |
| | NKX2.2 | Mouse monoclonal IgG2b | Santa Cruz, sc-398951 | 1:100 |
| | HNF3β | Mouse monoclonal IgG2a | Santa Cruz, sc-101060 | 1:100 |
| | OLIG2 | Mouse monoclonal IgG1 | Santa Cruz, sc-515947 | 1:100 |
| | HB9 | Goat polyclonal IgG | Santa Cruz, sc-22542 | 1:100 |
| | PAX7 | Mouse monoclonal IgG1 | Santa Cruz, sc-81648 | 1:100 |
| | Nestin | Mouse $IgG_1$ | Sigma, N5413 | 1:100 |
| | β-Tubulin III | Mouse monoclonal $IgG_1$ | Millipore, MAB1637 | 1:100 |
| Blood vessel cells | CD31 | Goat polyclonal IgG | Santa Cruz, sc-1506 | 1:200 |
| | VE-cadherin | Goat polyclonal IgG | Santa Cruz, sc-6458 | 1:200 |
| | ZO-1 | Mouse $IgG_1$ | Life Technologies, 33-9100 | 1:100 |

TABLE 1-continued

| | A list of antibodies for target markers. | | | |
|---|---|---|---|---|
| Cells | Primary Antibody | Origin/Isotype | Supplier/Cat# | Dilution |
| General | YAP | Rabbit IgG | Santa Cruz, sc-15407 | 1:100 |
| Secondary | Alexa 488, goat anti-mouse IgG$_1$ | — | Life Technologies, A-21121 | 1:200 |
| | Alexa 594, goat anti-mouse IgG | | Life Technologies, A-11058 | 1:200 |
| | Alexa 488, goat anti-mouse IgG$_{2a}$ | | Life Technologies, A-21131 | 1:200 |
| | Alexa 488, goat anti-mouse IgG$_{2b}$ | | Life Technologies, A-21141 | 1:200 |
| | Alexa 488, goat anti-rabbit IgG | | Life Technologies, A-11034 | 1:200 |

Image analysis of organoid morphology and YAP localization: To measure spheroid or organoid circularity and area during the experiments, phase-contrast images of hSCOs were taken with a microscope using a 4×and 10× objective every day up to day 18. These images were quantified with Image J software from National Institutes of Health (NIH). Briefly, the perimeter of each individual spheroid/organoid was drawn manually, and the enclosed area and circularity was measured. For YAP localization, the sections of stained organoids were imaged using a Zeiss LSM 880 confocal microscopy. YAP localization (nuclear or cytoplasmic) was analyzed using a quantification method through ImageJ as reported in a previous study [46].

Flow cytometry analysis for phenotypic marker expression: Briefly, the hSCOs and hBVOs were dissociated into single cells using Accutase and pipetting for 40 min. Then, 1×10$^6$ cells per sample were fixed with 4% paraformaldehyde and washed with staining buffer (2% FBS in PBS). The dissociated cells were permeabilized with 100% cold methanol for intracellular markers, blocked, and then incubated with primary antibodies against Chx10, LHX3, SOX2, NKX6.1, Nkx2.2, HNF3B, OLIG2, HB9, PAX7 followed by the corresponding secondary antibody (TABLE 1). The cells were acquired with BD FACSCanto™ II flow cytometer (Becton Dickinson) and analyzed against isotype controls using FlowJo software.

Reverse transcription-polymerase chain reaction (RT-PCR): Total RNA was isolated from different cell samples using the RNeasy Mini Kit (Qiagen, Valencia, CA) according to the manufacturer's protocol. The isolated RNA samples were further treated with DNA-Free RNA Kit (Zymo, Irvine, CA, USA) to remove genomic DNA contamination [55]. Reverse transcription was carried out according to the manufacturer's instructions using 2 ng of total mRNA, anchored oligo-dT primers (Operon, Huntsville, AL), and Superscript III (Invitrogen, Carlsbad, CA, USA). The software Oligo Explorer 1.2Primers (Genelink, Hawthorne, NY, USA) was used to design the real-time PCR primers specific for target genes (TABLE 2). For normalization of expression levels, β-actin was used as an endogenous control. Using SYBR1 Green PCR Master Mix (Applied Biosystems, Foster City, CA, USA), real-time PCR reactions were performed on an ABI7500 instrument (Applied Biosystems). The amplification reactions were performed as follows: 2 min at 50° C., 10 min at 95° C., and 40 cycles of 95° C. for 15 sec and 55° C. for 30 sec, and 68° C. for 30 sec following with a melt curve analysis. The Ct values of the target genes were first normalized to the Ct values of the endogenous control β-actin. The corrected Ct values were then compared to the experimental control. Fold changes in gene expression were calculated using the comparative Ct method: $2^{-(\Delta Cttreatment-\Delta Ctcontrol)}$ to obtain the relative expression levels.

TABLE 2

| Primer sequence for target genes. | | |
|---|---|---|
| Gene | Forward primer 5' to 3' | Reverse primer 5' to 3' |
| GLUT-1 | AGCAACTGTGTGGTCCCTACG (SEQ ID NO: 1) | AAGGTCCGGCCTTTAGTCTCA (SEQ ID NO: 21) |
| BCRP | CAGGTGTGCGTCAGAATCATC (SEQ ID NO: 2) | TCCAGGAGTGGTCAGATTCCTT (SEQ ID NO: 22) |
| PGP | ACCACTCTCCCACCTCCCTTA (SEQ ID NO: 3) | TTTAGCTGGGCTGCGTTTACA (SEQ ID NO: 23) |
| Dbx1 | AGCGAGACGACGTTTCTGAAG (SEQ ID NO: 4) | TAGGGAAAGGCGAAGGTCTTG (SEQ ID NO: 24) |
| Dbx2 | GGTATGGCCCACCCAGAGATA (SEQ ID NO: 5) | CTGTGACACCACGGCTTTCTT (SEQ ID NO: 25) |
| FOXA2 | CGGATCGAGGACAAGTGAGAG (SEQ ID NO: 6) | GGTGGGGGTGTTATGGATTTC (SEQ ID NO: 26) |
| Lmx1a | GGGAACCCAGAATGAGTTGGT (SEQ ID NO: 7) | CCAATGATGTCCCCAGAAATG (SEQ ID NO: 27) |

TABLE 2-continued

Primer sequence for target genes.

| Gene | Forward primer 5' to 3' | Reverse primer 5' to 3' |
|---|---|---|
| NKX2.2 | GCCTCTCCTTCTGAACCTTGG (SEQ ID NO: 8) | ACATTAACGCTGGGACGGTTT (SEQ ID NO: 28) |
| BRN3 | CGGTAGGACTTGGCTGTGAGA (SEQ ID NO: 9) | TGTTCTGTTTTCGCCCAACAT (SEQ ID NO: 29) |
| LHX9 | AGCCCTGCTTCTAGCCAATGT GCTCCGGACCATGAAATCCTA (SEQ ID NO: 10) | TGTTGTGAGGGCAGAGCACTA CAAGATTTGTTCTCCCTGCAAA (SEQ ID NO: 30) |
| OLIG2 | AAACTCCTCCACGTGCTTCCT (SEQ ID NO: 11) | TGTTACACGGCAGACGCTACA (SEQ ID NO: 31) |
| VWF | CCTCAACTGCCACCAATGACT (SEQ ID NO: 12) | GAACTGGCCCACAGGGTAGAT (SEQ ID NO: 32) |
| ZO1 | CGGGACTGTTGGTATTGGCTA (SEQ ID NO: 13) | CCCCCATTTACTGGCTGGTAT (SEQ ID NO: 33) |
| ISL1 | GCCAGTCCAGAGAGACACGAC (SEQ ID NO: 14) | GTCACTCTGCAAGGCGAAGTC (SEQ ID NO: 34) |
| OCLN | CCAATTGCTGCCACAAGAACT (SEQ ID NO: 15) | ATTTCTCCAAGGTCCCACAGC (SEQ ID NO: 35) |
| CD31 | AGTGTGACAAGCGTCATGGTG (SEQ ID NO: 16) | AGGCTTTGGTGAGACCCACTT (SEQ ID NO: 36) |
| CDH5 | TCGCTGTTGTCACATCTCAGG (SEQ ID NO: 17) | AGTGGAAGATGCATGGGTGAC (SEQ ID NO: 37) |
| CLDN1 | TGGGTTTCTTGCCTTAACCAG (SEQ ID NO: 18) | AGAAAGCATCGGGCCATACTC (SEQ ID NO: 38) |
| GFAP | GATCTCTGCCTCAGTGCTCCA (SEQ ID NO: 19) | GATATGCAGGAGGGTGGGTTT (SEQ ID NO: 39) |
| SELP | TAGCGATGAACTGCTCCAACC (SEQ ID NO: 20) | CCATTCTCTTGGCATGCTGTT (SEQ ID NO: 40) |

Whole-patch clamping for electrophysiology: Whole-cell patch clamp was used to record mature spinal cord spheroids cultured on small petri dish. The vessels were washed three times with extracellular recording solution containing 136 mM NaCl, 4 mM KCl, 2 mM MgCl, 10 mM HEPES, and 1 mM EGTA (312 mOsm, pH 7.39) and then were incubated in this solution at RT during recording. Glass electrodes (resistance 1-5 M (2) were filled with intracellular solution containing 130 mM KCl, 10 mM HEPES, and 5 mM EGTA (292 mOsm, pH 7.20). Cells were visualized under phase contrast with a Nikon Eclipse Ti-U inverted microscope with an attached DS-Qil monochrome digital camera. Recordings were made with an Axopatch 200B amplifier (Molecular Devices) and digitized with a Digidata 1440A system (Molecular Devices). Ionic currents were recorded under a voltage clamp protocol (−60 mV to 135 mV in 15 mV steps, 250 ms in duration).

Statistical Analysis: The differences were analyzed by independent t-test or one-way ANOVA followed by Tukey's multiple comparisons post hoc tests. The difference was considered statistically significant at p≤0.05 and all quantitative data are presented as mean±standard deviation.

Results

Figures 2A, 2B, 2C, 2D:
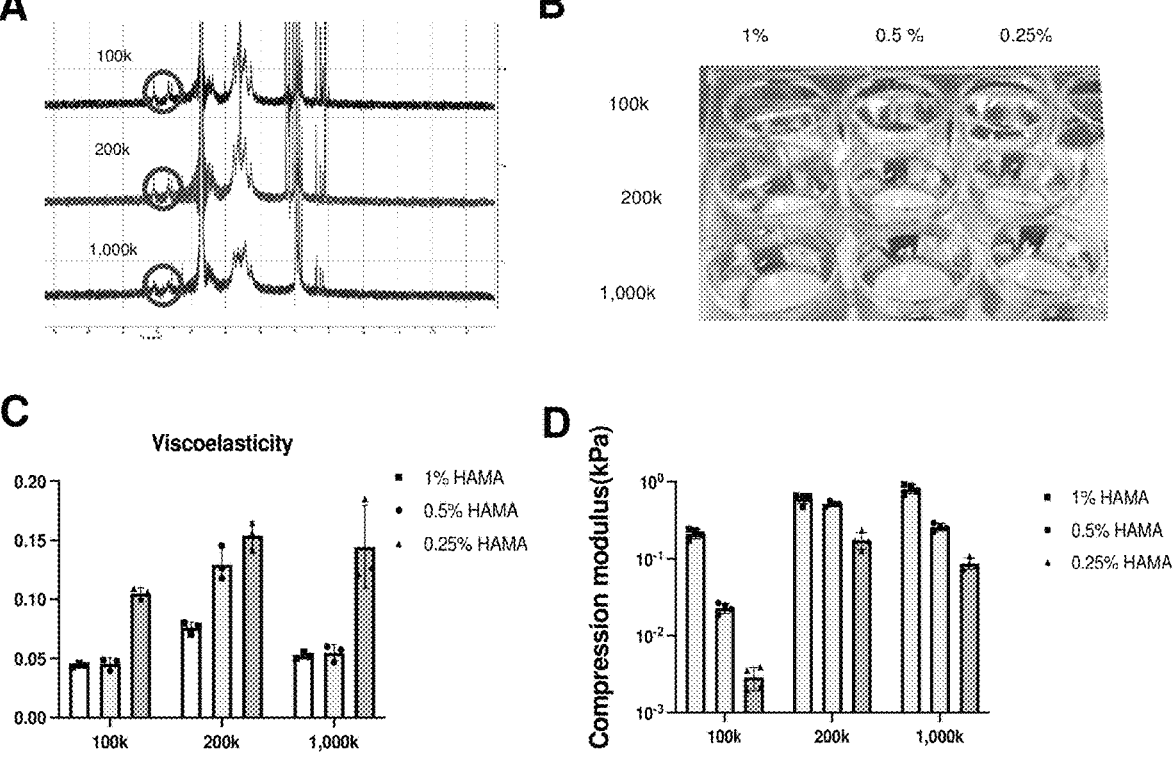
FIGS. 2A-2D depict characterizations of HAMA hydrogels.
Figure 3:
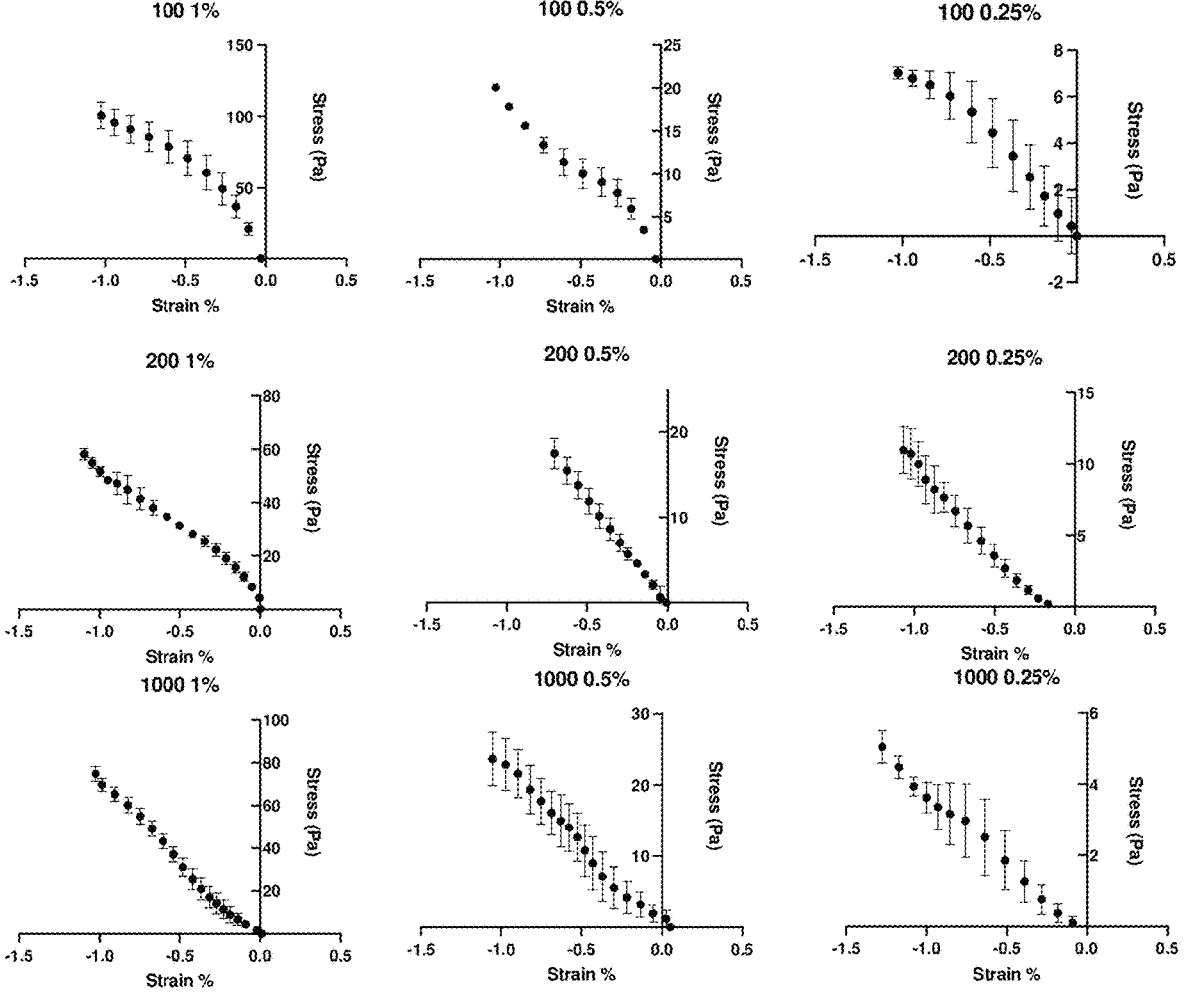
FIG. 3 depicts quantification of the compression modulus for HAMA hydrogels versus strain. N=4 independent gels for each composition.
Figures 4A, 4B, 4C:
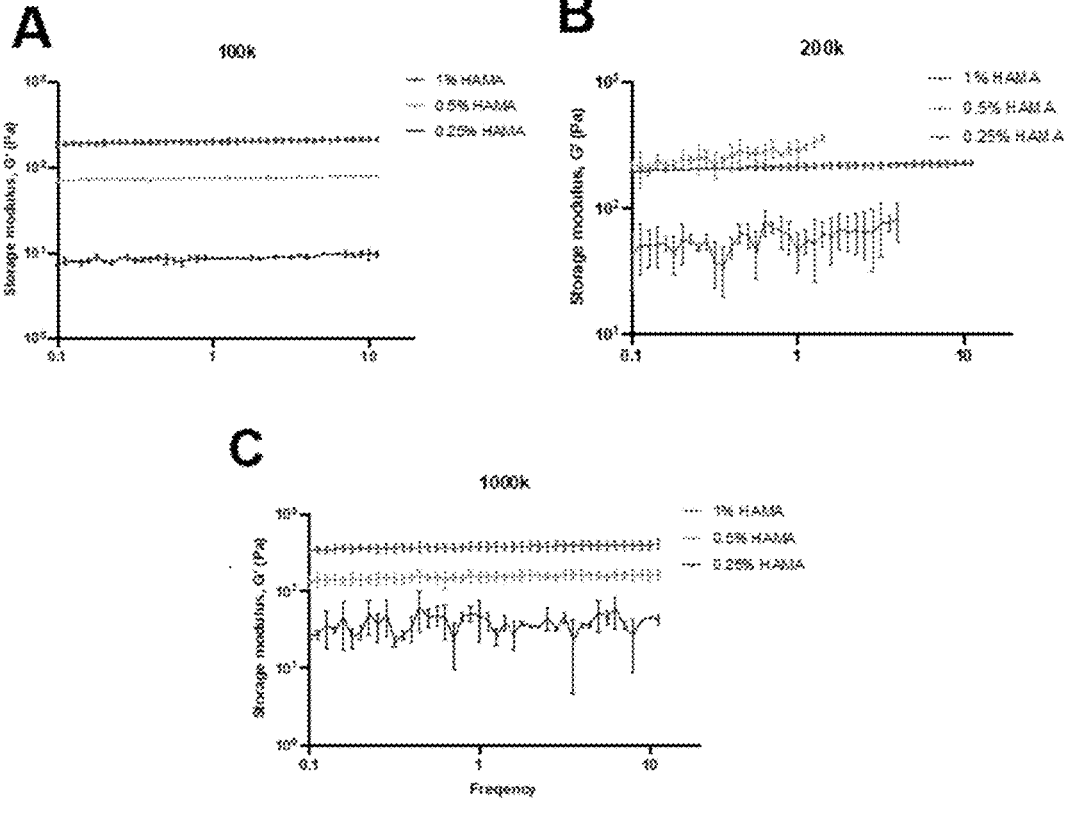
FIGS. 4A-4C depict frequency sweep of different HAMA hydrogels: 100k (FIG. 4A), 200k (FIG. 4B), and 1000k (FIG. 4C).

HA Hydrogel fabrication and characterizations: In FIG. 1A, the schematic illustrations demonstrate the fabrication process of HAMA and HAMA@HA-Cat hydrogels. The modification of HA with methylate group, catechol groups, and both groups were verified from the HINMR results (FIG. 2A). The double bond peaks introduced by the modification of MA appeared at 5.60 ppm and 6.04 ppm and the benzene ring peak introduced by the modification of dopamine appeared at 6.72 ppm, 7.10 ppm, and 7.13 ppm. Then the degrees of modification of 100k, 200k and 1,000k HAMA are 50.4%, 50.0%, 45.4%, respectively.

Figure 5:
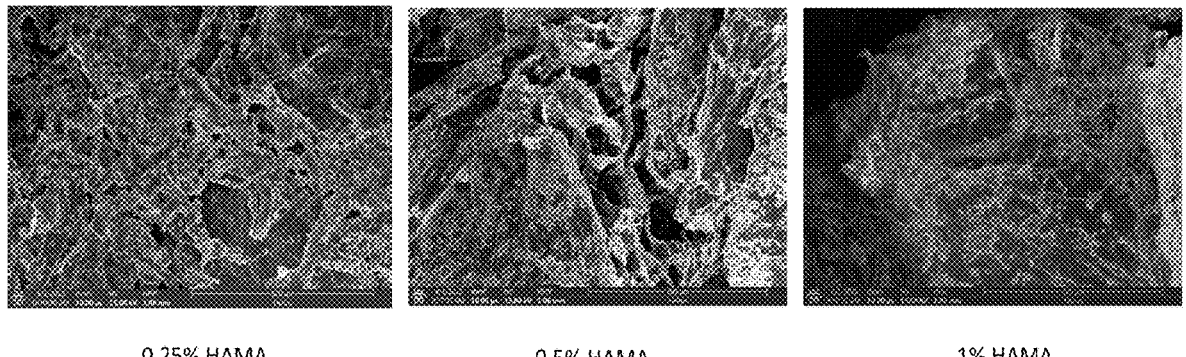
FIG. 5 depicts scanning electron microcopy (SEM) images for freeze-dried HAMA hydrogels with different concentrations.

HAMA hydrogels were fabricated with 3 different molecular weights and each sample was dissolved in PBS at 1%, 0.5%, and 0.25% (w/w) concentration (FIG. 2B). Different concentrations of HAMA could change the degree of crosslinking during gelation which leads to different mechanical properties [23]. Then, the mechanical and rheological properties were tested using a TA Ares-G2 (FIGS. 1B-1C, FIGS. 2C-2D, FIG. 3, FIGS. 4A-4C). The storage modulus of the hydrogels decreased, and viscoelasticity increased with decrease in the mass fraction. The tanδ of the gels was between 0.044 and 0.154 for the selected groups (Gel 1-4). Then a group of compression modulus (E) was derived from compression test and was found to be in the range of 400 and 7,000 Pa. In TABLE 3, four types of hydrogels were selected from the 9 synthesized hydrogels, which can provide stiff-elastic (Gel 1), soft-clastic (Gel 2), stiff-viscoelastic (Gel 3), and soft-viscoelastic (Gel 4) hydrogel conditions. Usually, stress relaxation is used to evaluate the viscoelasticity of the polymer materials. Therefore, the stress relaxation test was also performed for the four HAMA hydrogels and the data were regressed with updated maxwell model (FIG. 1D) [56]:

$$\sigma(t) = (\sigma_0 - C)e^{\frac{-t}{\tau}} + C(\text{plateau})$$

where σ stands for stress (Pa), $\sigma_0$ stands for initial stress (Pa), t stands for time(s), τ stands for relaxation time(s) and C is a constant relating to the crosslink of the polymer. The four stress relaxation times are 420 s, 660 s, 266 s, and 19 s, respectively. All relaxation times (t) of the four samples are relatively short but significantly different. The degree of crosslinking of the hydrogels may be high with less fluid or dynamic part. The morphology of HAMA hydrogels is shown in SEM images, with visible porous structure (FIG. 5). These results indicate that the hydrogels with different viscoelastic properties, i.e., stiff-elastic (Gel 1), soft-elastic (Gel 2), stiff-viscoelastic (Gel 3), and soft-viscoelastic (Gel 4), can be fabricated.

Figures 7A, 7B:
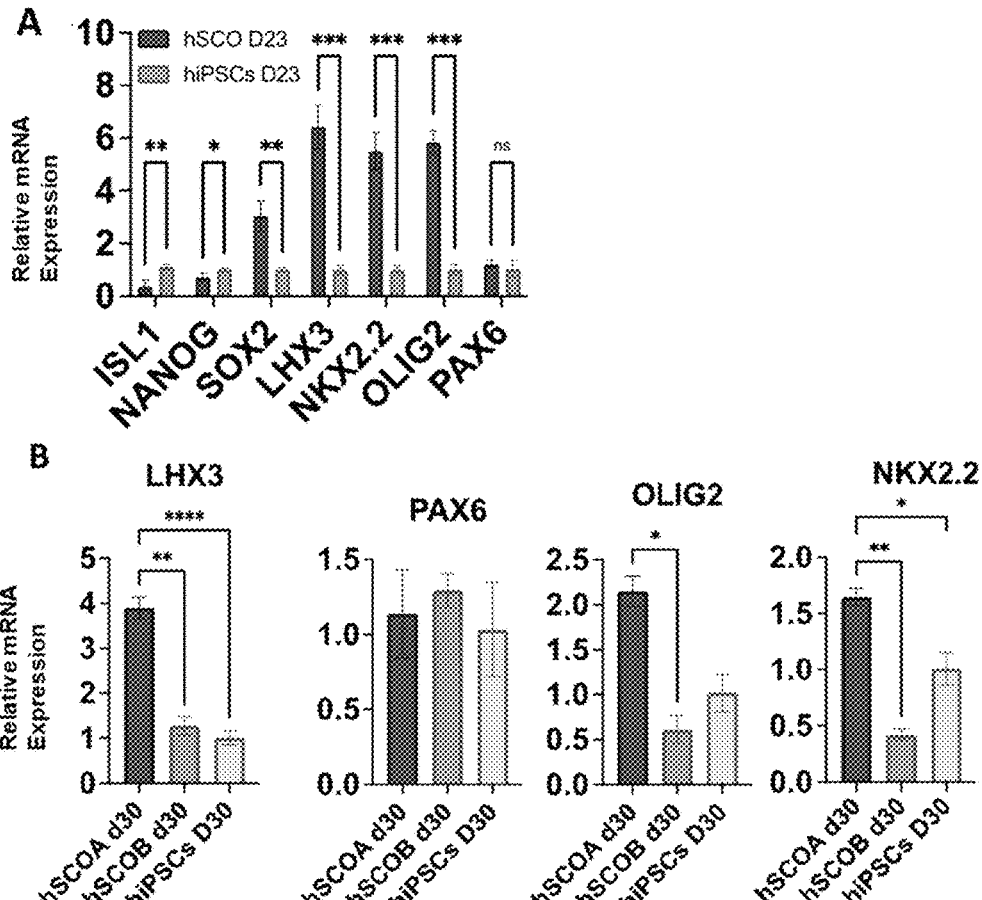
FIGS. 7A-7B depict RT-PCR analysis for hSCO differentiation.

LHX3, NKX2.2, OLIG2) for the hSCO group was much higher than the hiPSC group, indicating the effective induction of hSCO lineage. PAX6 (a progenitor marker) had no difference between the hSCOs and the hiPSCs while ISLI (a progenitor marker) and Nanog (a pluripotent gene) were higher for the hiPSC group. The current differentiation protocol (referred to as hSCOA) was furthered compared with a caudal hSCO differentiation protocol (referred to as hSCOB), which used SB431542 (inhibition of transforming growth factor signaling), CHIR, RA, and bFGF (FIG. 7B).

TABLE 3

Properties of HAMA hydrogels with different molecular weights and concentrations.

| Parameters | 100k 1% | 100k 0.5% | 100k 0.25% | 200k 1% | 200k 0.5% | 200k 0.25% | 1,000k 1% | 1,000k 0.5% | 1,000k 0.25% |
|---|---|---|---|---|---|---|---|---|---|
| Tan δ | 0.037 | 0.038 | 0.079 | 0.066 | 0.113 | 0.149 | 0.041 | 0.048 | 0.158 |
| E(Pa) | 5283 ± 265 | 1265 ± 143 | 605 ± 97 | 5050 ± 348 | 2624 ± 112 | 1208 ± 90 | 7456 ± 539 | 2213 ± 384 | 419 ± 127 |
| Stress relaxation time(s) | 420.1 | 666.7 | n/a | n/a | n/a | 283.4 | n/a | n/a | 19.7 |
| Category | stiff-elastic | soft-elastic | n/a | n/a | n/a | stiff-visco-elastic | n/a | n/a | soft-visco-elastic |
| ID | Gel 1 | Gel 2 | n/a | n/a | n/a | Gel 3 | n/a | n/a | Gel 4 |

Figures 8A, 8B:
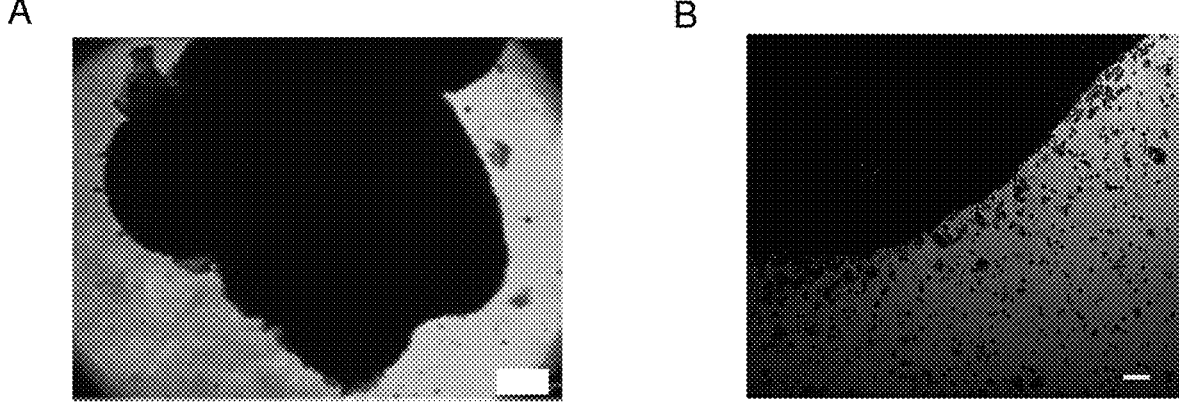
FIGS. 8A-8B depict images of hSCOs after 40 days culture.

Evaluation of hSCO derivation from hiPSCs: The schematic illustration of hSCO differentiation from hiPSCs reveals that differentiation was induced using LDN193189 (inhibition of bone morphogenetic protein signaling), CHIR (Wnt activation), RA (retinoid activation), and Purmorphamine (Sonic Hedgehog signaling activation) (FIG. 6A) [47]. The ventral spinal cord organoids were generated and characterized for spinal cord markers of different regions, including dorsal, interneuron, and ventral markers (TABLE 4). The marker expression was compared with undifferentiated hiPSC aggregates (FIG. 7A). After 23 days of differentiation, the gene expression of ventral markers (SOX2, hSCOA conditions showed higher LHX3, NKX2.2, OLIG2 expression, while PAX6 was comparable among the three groups. Based on these results, the hSCOA protocol was selected for the subsequent experiments. The hSCOs can be replated onto Matrigel-coated surface. Extended axons from the replated organoids were observed and the edges remained intact until day 44 (FIGS. 8A-8B). The hSCOs were maintained in the Vertical-wheel bioreactor for long-term culture until day 80, which showed larger organoids (~2 mm) with the defined organoid edges.

TABLE 4

Summary of markers for hSCO patterning.

| | | |
|---|---|---|
| Early progenitor markers | SOX2 | SOX2 is a neuroepithelial marker |
| | ISL1 | A hindbrain progenitor marker |
| | NKX6.1 | NKX 6.1 works in conjunction with other transcription factors to pattern the neural tube and regulate the differentiation of neuronal subtypes |
| Dorsal markers | LMX1a | it is involved in the development of the roof plate of the neural tube, which is important for the patterning of the dorsal spinal cord. |
| | LHX9 | LHX9 is expressed in the dorsal spinal cord and is involved in the development of specific interneuron populations. |
| | BRN3 | It is involved in the development of the nervous system, particularly in the differentiation of sensory neurons. |
| | LHX3 | LHX3 is essential for the differentiation of specific classes of motor neurons, particularly those in the medial motor column, which innervate axial muscles |
| | PAX7 | PAX 7 expressed in dorsal neural progenitors and plays a role in the development of dorsal spinal cord interneurons. |
| Interneuron markers | DBX1/DBX2 | DBX1 is crucial for the specification of V0 and V1 interneurons in the spinal cord, which are important for coordinating motor circuits. DBX2 is involved in the development of V2 interneurons in the spinal cord, which contribute to motor control and sensory processing. |
| | PAX6 | It plays a role in the specification of dorsal spinal cord neurons, including certain sensory interneurons. |

TABLE 4-continued

| | | Summary of markers for hSCO patterning. |
|---|---|---|
| | CHX10 | CHX 10 expressed in certain populations of neurons in the spinal cord, particularly in the V2a interneurons. |
| Ventral markers | NKX2.2 | NKX2.2 is crucial for the development of ventral spinal cord neurons |
| | OLIG2 | OLIG2 is critical for the development of motor neurons and oligodendrocyte progenitors in the ventral spinal cord |
| | FOXA2 | It plays a crucial role in the development and differentiation of motor neurons in the ventral spinal cord. |
| | HNF3β | It is critical for the development of floor plate in the neural tube and for ventral patterning |
| Motor neurons | HB9 | Mature motor neuronal marker |

Figures 6A, 6B, 6C, 6D, 6E:
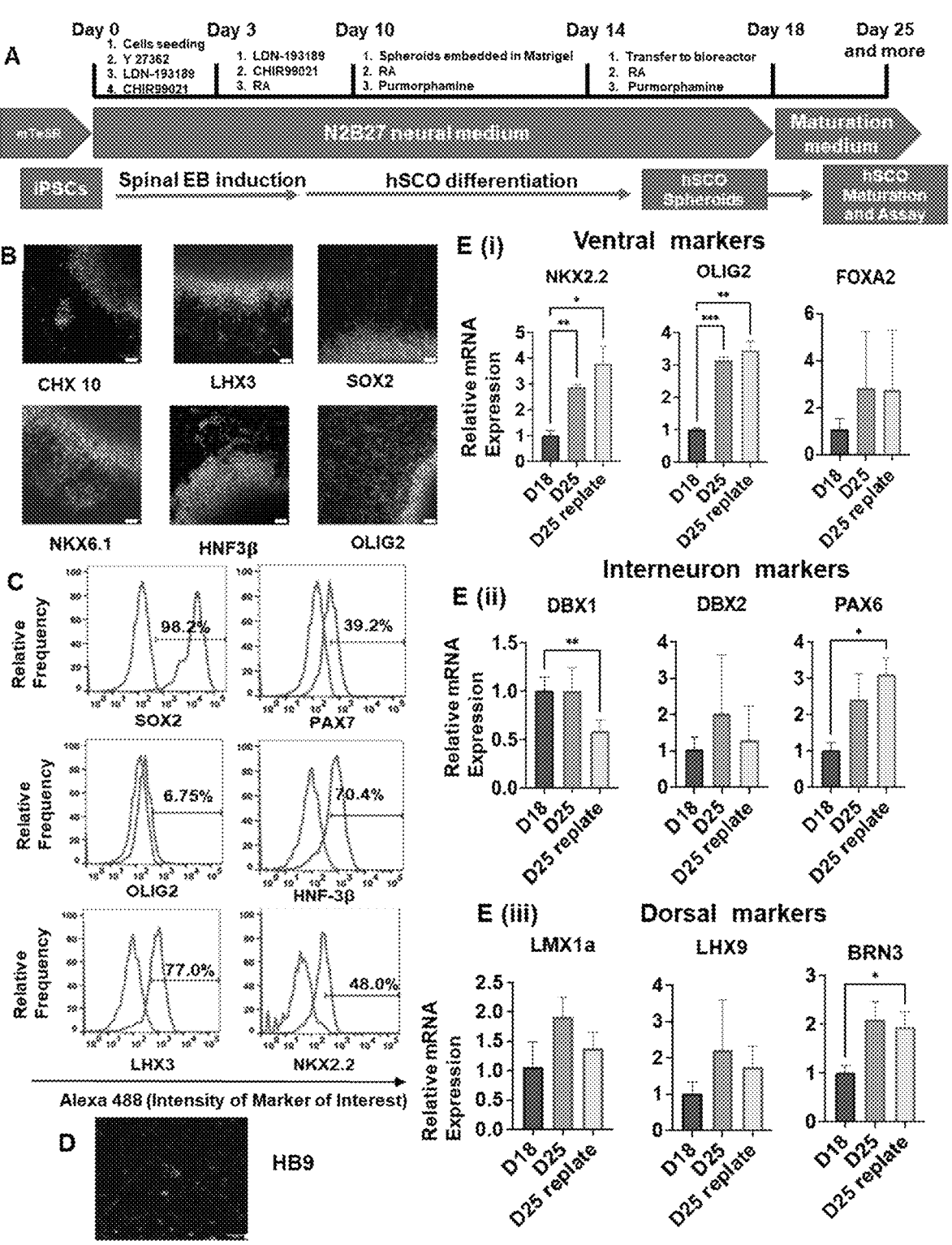
FIGS. 6A-6E depict ventral hSCO differentiation and characterization.
Figure 9:
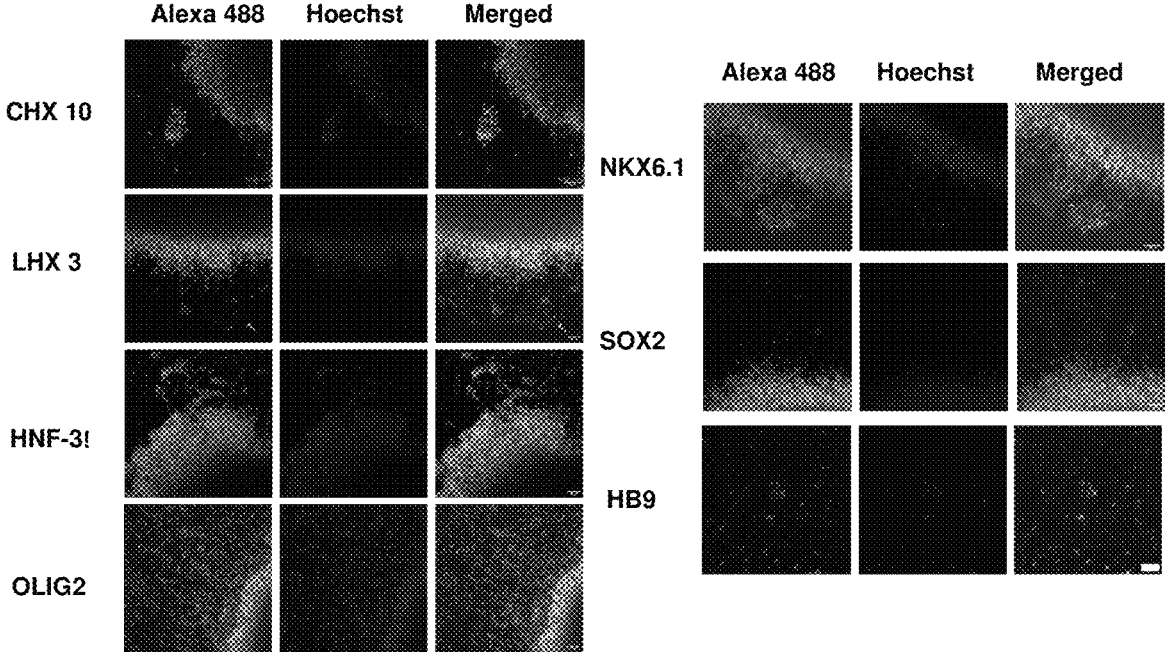
FIG. 9 depicts immunostaining images of ventral hSCO markers. Scale bar: 50 µm.
Figures 10A, 10B, 10C, 10D, 10E:
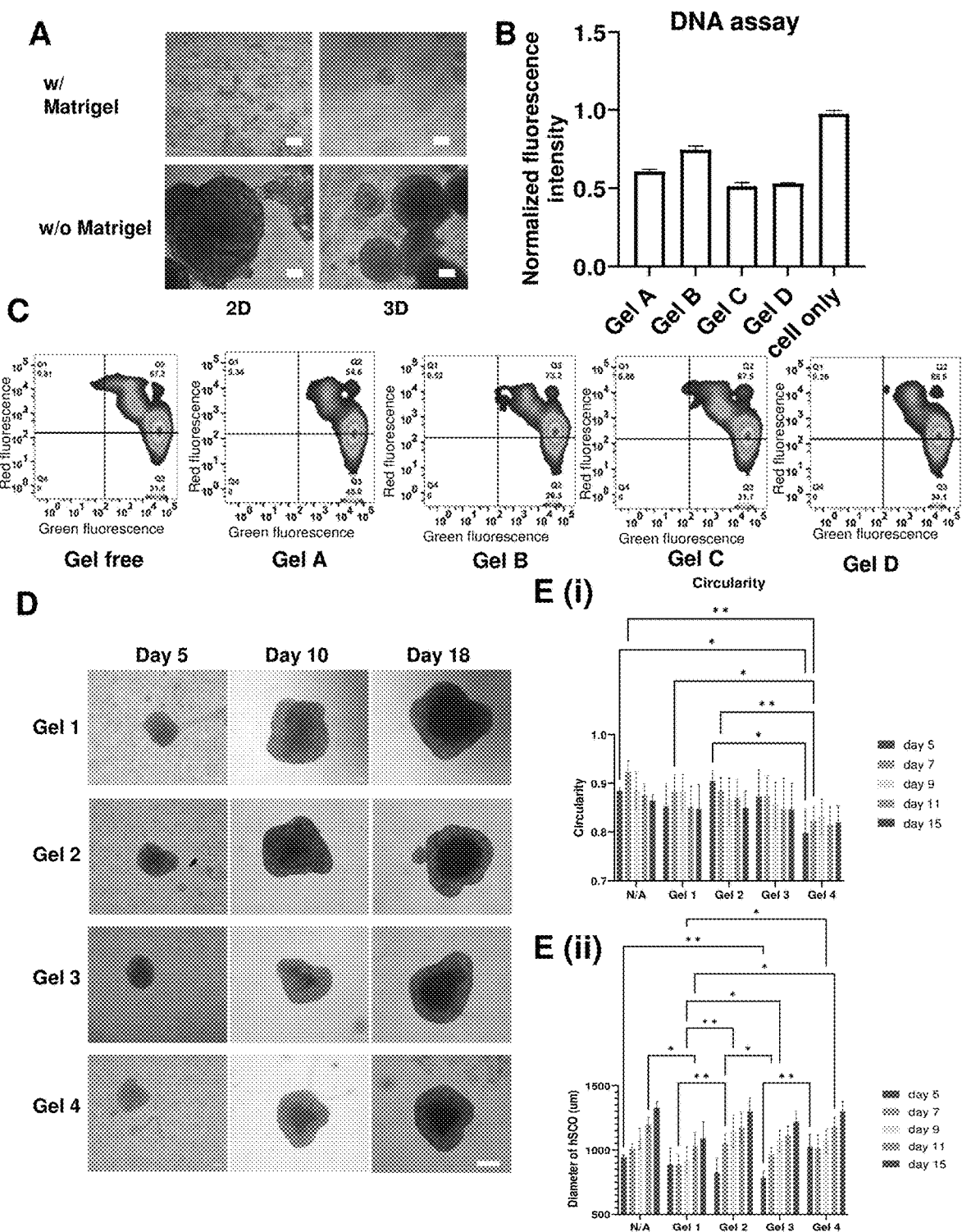
FIGS. 10A-10E depict biocompatibility of the HAMA hydrogels and morphogenesis of the organoids.

To verify the hSCO marker expression at the protein level, the day 18 organoids were replated for immunostaining (FIG. 6B and FIG. 9). Seven hSCO patterning markers were evaluated, and the expression of CHX10, LHX3, NKX6.1, HNF3B, and OLIG2 was observed. In addition, neuroepithelial marker SOX2 had a high expression, indicating hSCO induction. Flow cytometry analysis was performed on day 25 samples to quantify the marker expression. Most ventral markers (except OLIG2) showed high expression (98.2% SOX2, 70.4% HNF3B, and 48.0% NKX2.2). Dorsal markers PAX7 (39.2%) and LHX3 (77.0%) were also expressed (FIG. 6C). Of note, HB9, one of the motor neuron markers, was detected (FIG. 6D). To evaluate hSCO patterning, RT-PCR was performed to characterize gene expression of different functional regions of the spinal cord (FIG. 6E). For the ventral markers, NKX2.2 and OLIG2 had increased expression (3-4 fold) after one week of culture (day 25 vs. day 18, replated or not), when growth factors were withdrawn for maturation. FOXA2 showed no statistical difference. For interneuron markers, the expression of PAX6 was increased (~3-fold), but not DBX1 and DBX2. The increased PAX6 expression may be due to the maturation of specific neural cells. For dorsal markers, BRN3 was expressed more (~2-fold) after one week maturation, while the increase was not statistically significant for LMX1α and LHX9. These results indicate the effective hSCO derivation from hiPSCs for the investigation of hSCO patterning in the hydrogels and the extended differentiation time promotes hSCO maturation.

hSCO patterning in hydrogels with different stiffness and viscoelasticity: Next, for further hSCO differentiation within the hydrogels, the biocompatibility of the HAMA hydrogels was firstly investigated in 2D undifferentiated hiPSC culture and 3D undifferentiated hiPSC spheroids. The hiPSCs grew well when culturing with HAMA hydrogels during the 7-day period (FIG. 10A). By adding Matrigel, the adhesion of hiPSCs on 2D surface was improved. For 3D culture, the morphology (e.g., size) of hiPSC spheroids was similar with or without the addition of Matrigel. Then, hiPSCs were cultured in four different gels with a cell-only control. DNA assay was performed to evaluate cell growth and Live/Dead assay was performed to measure cell viability. The normalized DNA concentration shows that the proliferation of hiPSCs cultured with different HAMA hydrogels was comparable (FIG. 10B). The proliferation rates were lower than the cell-only condition, possibly because some of the hiPSCs were embedded into gels and did not proliferate much. For the Live/Dead assay, the five groups showed similar results with about 90% of live cells (FIG. 10C), which indicates that all the hydrogels have good biocompatibility for hiPSCs.

Figure 11:
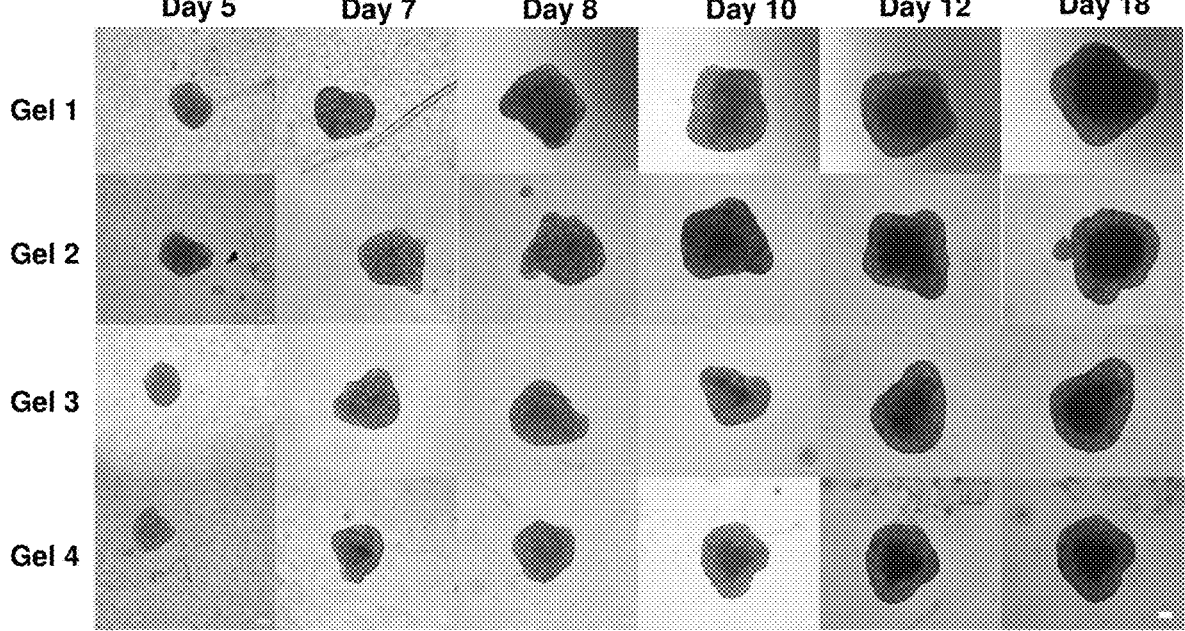
FIG. 11 depicts hSCO morphogenesis during the induction period in different hydrogels. Scale bar: 200 µm.

After the biocompatibility test, the spinal cord organoids (hSCOs) derived from hiPSCs were patterned in different HAMA hydrogels. Images of the formed spheroids in the four different hydrogels were taken over 18 days of differentiation (FIG. 10D and FIG. 11). The size of the spheroids increased significantly from day 5 (about 500-800 μm) to day 18 (about 1.5-1.8 mm). Image analysis was performed based on spheroid morphology to reveal if different HAMA hydrogels affect the spheroid size and shape. The quantitative summary of the diameter and circularity is shown in FIG. 10E. The diameters of all spheroids were similar (~1.4 mm) for different hydrogel groups at day 15, however, they were different on the days prior to day 15, showing different growth kinetics of the spheroids. For example, the Gel 3 group started with the smaller spheroids but the spheroid size quickly increased to a size similar to the other groups. In addition, all spheroids in the HAMA hydrogels can freely grow without constriction from the hydrogels during the culture, which contributes to the size increase during the differentiation. The circularities of the spheroids all decreased over the course of differentiation (the closer to 1 the more circular). Only the spheroids in Gel 4 were less circular than the other conditions in the initial few days. These results indicate that the four types of HAMA hydrogels all support hSCO patterning.

Figures 12A, 12B, 12C, 12D:
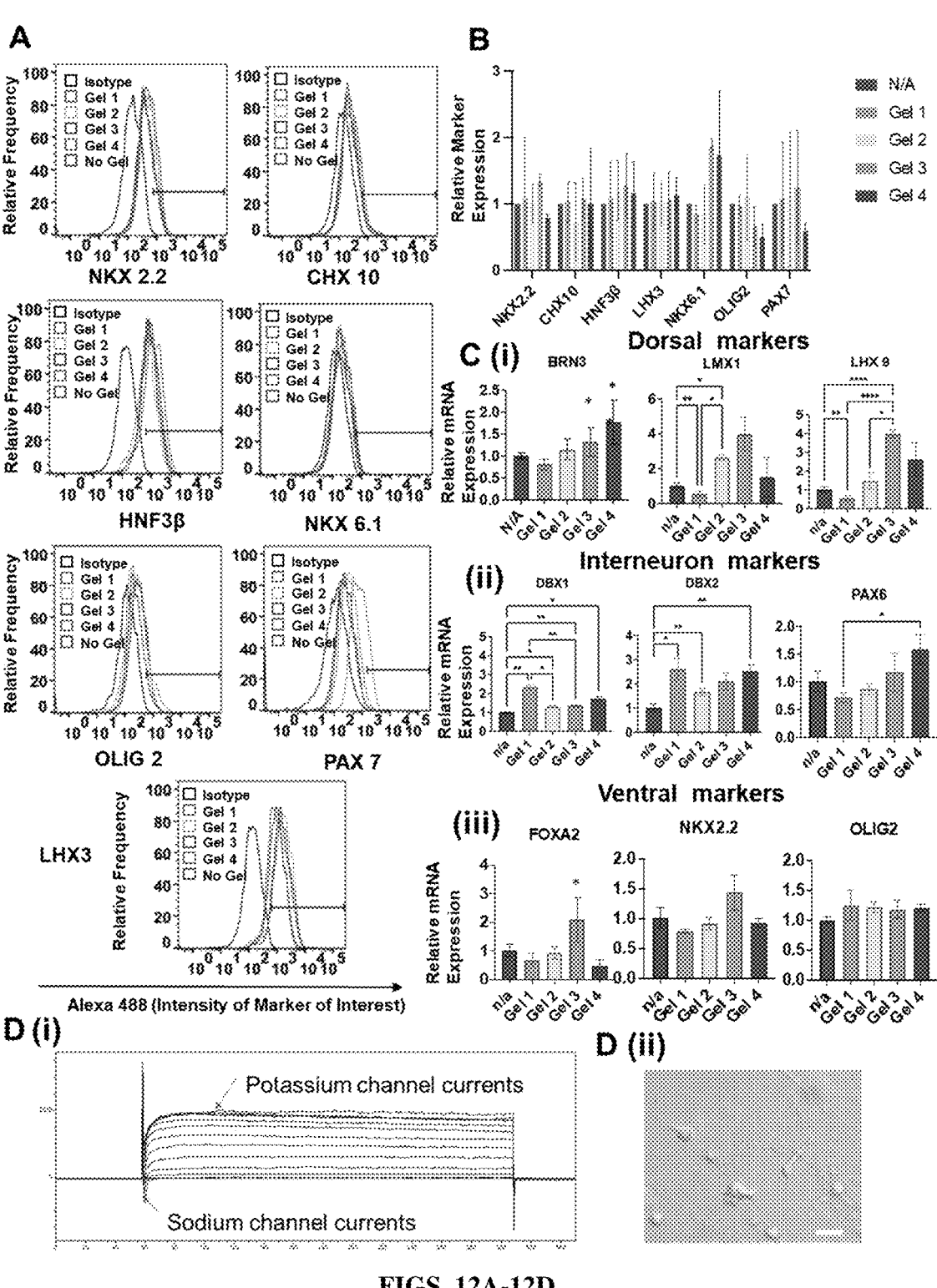
FIGS. 12A-12D depict characterization for differentiation of hSCOs in different HAMA hydrogels.
Figure 13:
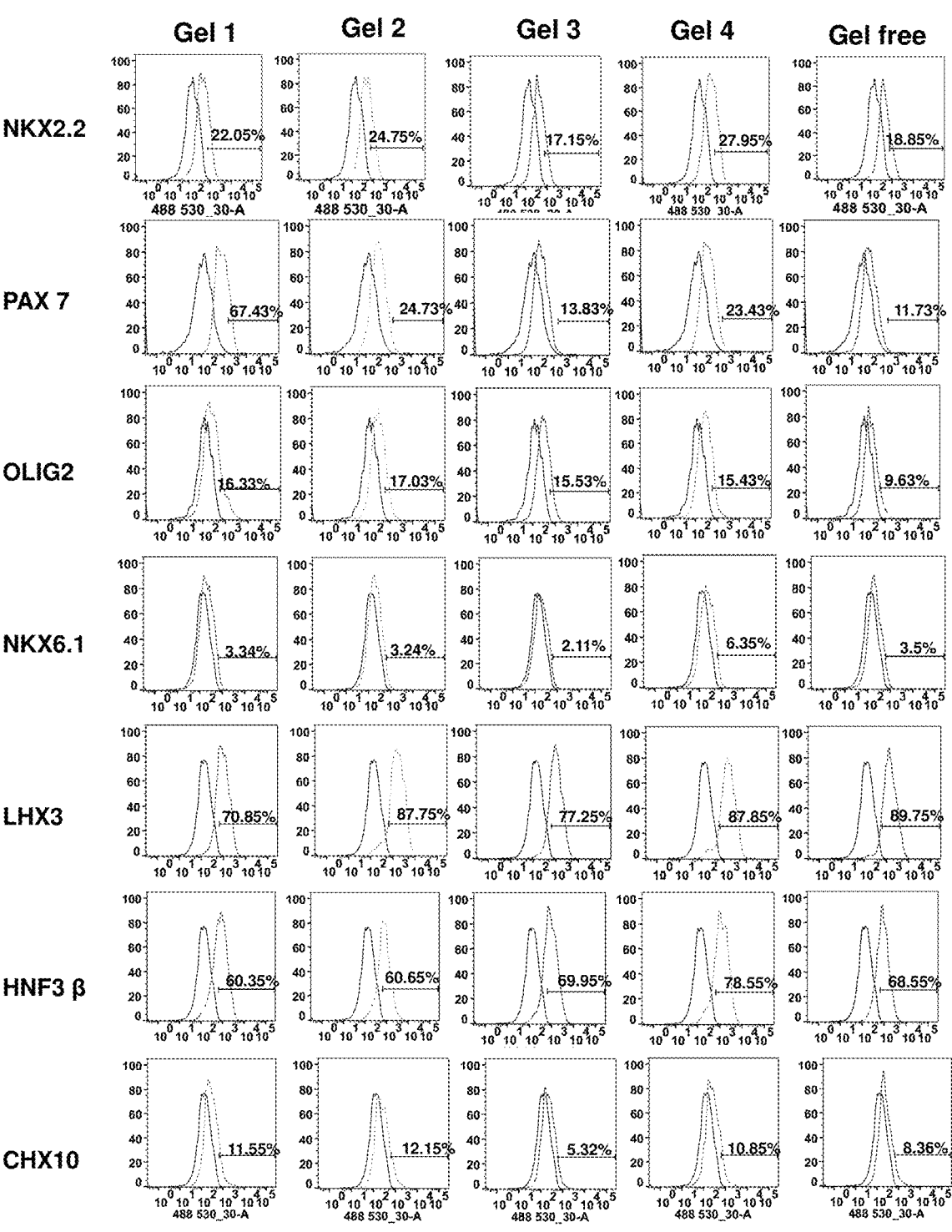
FIG. 13 depicts flow cytometry analysis of different markers for hSCO formed in different hydrogels. For each histogram, X-axis: Alex 488 intensity of marker of interest; Y-axis: relative frequency.

After day 25, flow cytometry was performed to quantify hSCO marker expression at the protein level among different culture conditions (FIGS. 12A-12D and FIG. 13). The ventral markers of hSCOs were evaluated, and similar expression levels among different hydrogel groups were observed. The LHX3 (70-90%) and HNF3B (60-80%) had high expression while Nkx2.2 was expressed at 17-28%, OLIG2 was 10-16%, and CHX10 was 8-12%. Nkx6.1 expression was low around 2-7%. PAX7 showed large variations of 12-67%. The data from three different runs were normalized to the cell-only group and then combined together to make comparisons (FIGS. 12A-12B and FIG. 11). There were large variations among three different runs and no statistical difference was observed, which may be attributed to organoid-to-organoid variations [57].

Furthermore, RT-PCR was performed to evaluate patterning markers at the molecular level (FIG. 12C). For dorsal markers, Gel 1 reduced the expression of LMX1 and LHX9 while the highest expression was observed for the Gel 3 group. BRN3 expression was higher for the Gel 3 and Gel 4 groups in comparison to the Gel 1 group. For the interneuron marker expression, the presence of the hydrogels increased the expression of interneuron markers DBX1 and DBX2. Comparing with other gels, Gel 1 promoted higher expression of DBX1. PAX6 expression was higher for the Gel 3 and Gel 4 group in comparison to the Gel 1 group. For the ventral marker expression, Gel 3 promoted higher expression of FOXA2 and NKX2.2 in comparison to other conditions. There was no statistical difference among different conditions for OLIG2. Taken together, Gel 3 (stiff-viscoelastic) promoted dorsal and ventral marker expression and Gel 1 (stiff-clastic) promoted interneuron marker expression during hSCO patterning. These results indicate that the stiffer hydrogels are preferred for hSCO differentiation and the viscoelastic hydrogels promote regional hSCO patterning compared to the clastic hydrogels.

Electrophysiology was performed to show the functional properties of hSCOs (FIG. 12D). The electrophysiological properties of the outgrowth cells of the derived organoids were examined via patch clamping. The replated organoids displayed fast inward currents and long-lasting outward currents during voltage-clamp recording, suggesting the presence of functional voltage-gated $Na^+$ and $K^+$ channels, respectively.

Figures 14A, 14B:
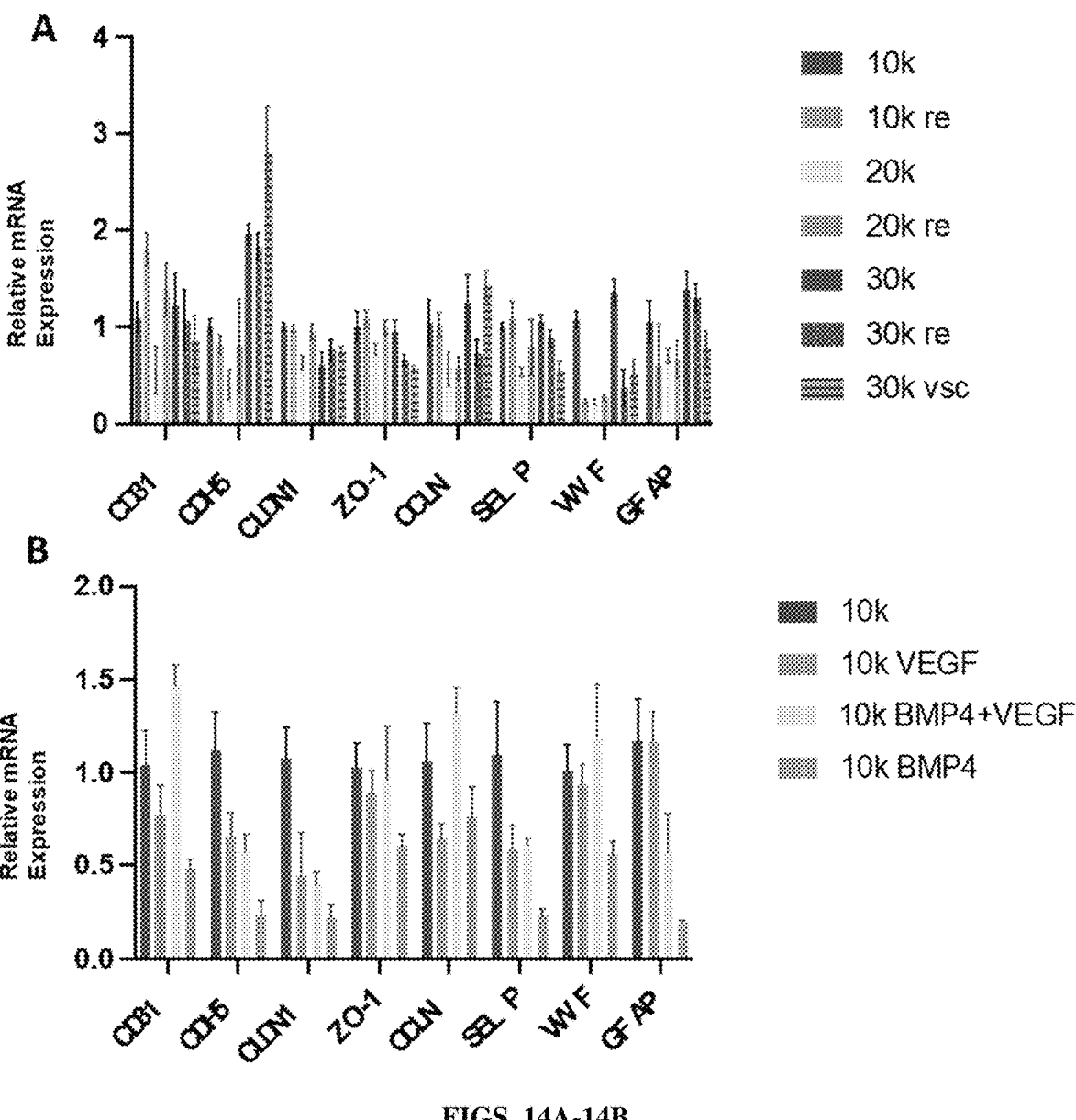
FIGS. 14A-14B depict endothelial markers expression by different culture condition for hBVOs.

Coculture of hSCOs from different hydrogels with hBVOs: The protocol of hBVO differentiation from hiPSCs was firstly evaluated for the marker expression of the endothelial cells (CD31, VWF) and tight junction (CDH5, CLDNI, ZO-1, OCLN, SELP, and GFAP) of the BSCB at different seeding densities (10,000, 20,000, and 30,000 cells/well in ULA 96-well plate) and replating (re) conditions (FIG. 14A). The vascular differentiation (vsc) from hiPSCs was also compared [46]. Only CDH5 showed different expression levels among different conditions. The 30k, 30k re, and 30k vsc showed higher CDH5 expression than other densities. For the rest of the markers, the 10k conditions had higher expression in general. In addition, the replated organoids did not show higher marker expression in comparison to organoids in suspension. Based on these RT-PCR results, the suspension culture and the seeding density of 10k cells/well were selected for the generation of hBVOs. Then, the BMP4 and VEGF alone or in combination were tested as additional growth factors for hBVO generation (FIG. 14B). BMP4 significantly decreased the expression of tight junction and BSCB markers. Adding VEGF (with or without BMP4) did not significantly increase the marker expression in general. Therefore, the hBVO differentiation protocol without additional BMP4 and VEGF was used for subsequent experiments.

Figures 15A, 15B, 15C:
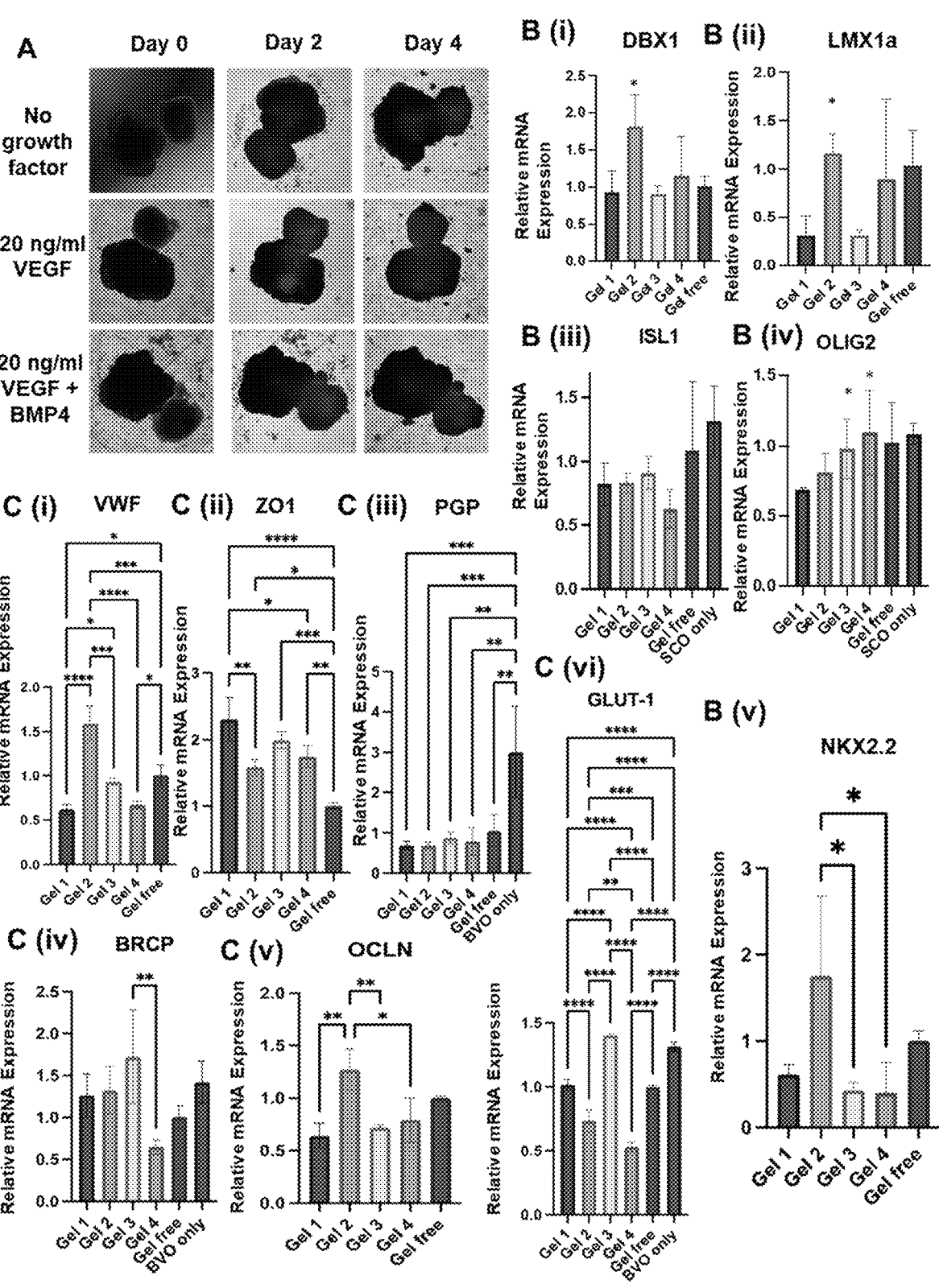
FIGS. 15A-15C depict hSCO and hBVO coculturing for Blood-Spinal Cord Barrier (BSCB) generation.

Afterwards, the assembly of hBVOs and hSCOs in the presence of HAMA hydrogels was performed (FIG. 15A). The hBVOs were labeled with CellTracker™ Red and transferred to a well containing one hSCO. The fusion of the hBVO with the hSCO was indicated by the red color inside the hSCO. With VEGF, the fusion rate was much faster than the other two conditions of no growth factor or with BMP4. After coculture for 3 weeks, the merged organoids (i.e., hSCO-hBVO) from five different conditions (i.e., Gel 1-4 and Gel-free) were harvested for RT-PCR analysis for the expression of spinal cord markers (FIG. 15B) or BSCB markers (FIG. 15C) [12]. For the spinal cord markers, DBX1 and LMX1α were higher for the Gel 2 group than the Gel 1 and Gel 3 groups, but comparable to the Gel 4 group. ISLI had no difference among different hydrogel groups. The expression of OLIG2 of hSCOs derived from the Gel 4 group was higher than the Gel 1 group. NKX2.2 expression was the highest for the Gel 2 condition compared to the other groups. Taken together, the presence of hBVOs altered the influence of different hydrogels on spinal cord organoid patterning. Gel 2 (soft-clastic) promoted dorsal and interneuron markers as well as NKX2.2, while Gel 3 and 4 (viscoclastic) promoted ventral marker OLIG2 expression.

These results indicate that the effects of viscoelastic properties of the hydrogels become more dominant than the stiffness effects.

For the BSCB markers in the fused hSCO-hBVO, the Gel 2 condition had the highest VWF (i) and OCLN (v) expression in comparison to the other groups (FIG. 15C). These markers are important for identifying the tight junction during coculture [58]. The tight junction protein ZO-1 (ii) was expressed higher in Gel 1 and Gel 3 groups when compared to the other conditions. The expression of glucose transporter 1 (GLUT-1) and efflux transporters, BCRP and PGP, was also determined. For PGP (iii), all the hSCO-hBVO conditions showed lower expression than the hBVO only group, due to the presence of hSCO cells. BRCP (iv) expression was comparable for all the conditions except for the Gel 4 group, which had lower expression. For GLUT-1 (vi), the Gel 3 group had the highest expression while Gel 4 had the lowest expression. Taken together, the BSCB markers were differentially affected by the viscoelastic properties of the HAMA hydrogels. Gel 2 (soft-elastic) promotes the tight junction and Gel 3 (stiff-viscoclastic) promotes the expression of glucose and efflux transporters.

HAMA-Cat ($Fe^{3+}$) dynamic hydrogels for continuous hydrogel improvement: In addition to single covalent hydrogels that were investigated so far, the viscoelastic dual hydrogels with dynamic crosslinking bonds may also affect hSCO patterning. HAMA was crosslinked with covalent bonds and the entanglement of the chains provides the dynamic part that contributes to the viscoclastic behaviors of the hydrogels. In addition to modifying the covalent cross-linked HAMA hydrogels with dynamic crosslinked properties, dopamine, which has a catechol group, was grafted on the HA to synthesize HA-Cat (FIGS. 16A-16E). The catechol group can react with ferric ions ($Fc^{3+}$) with coordination. The HAMA and HA-Cat polymers were mixed with the same concentration as the four HAMA hydrogels (100 k, 1%, 100 k 0.5%, 200 k 0.25%, 1000 k 0.25%), and the HAMA@HA-Cat hydrogels were fabricated which are referred as Gel 5, Gel 6, Gel 7, and Gel 8, respectively.

Figures 16A, 16B, 16C, 16D, 16E:
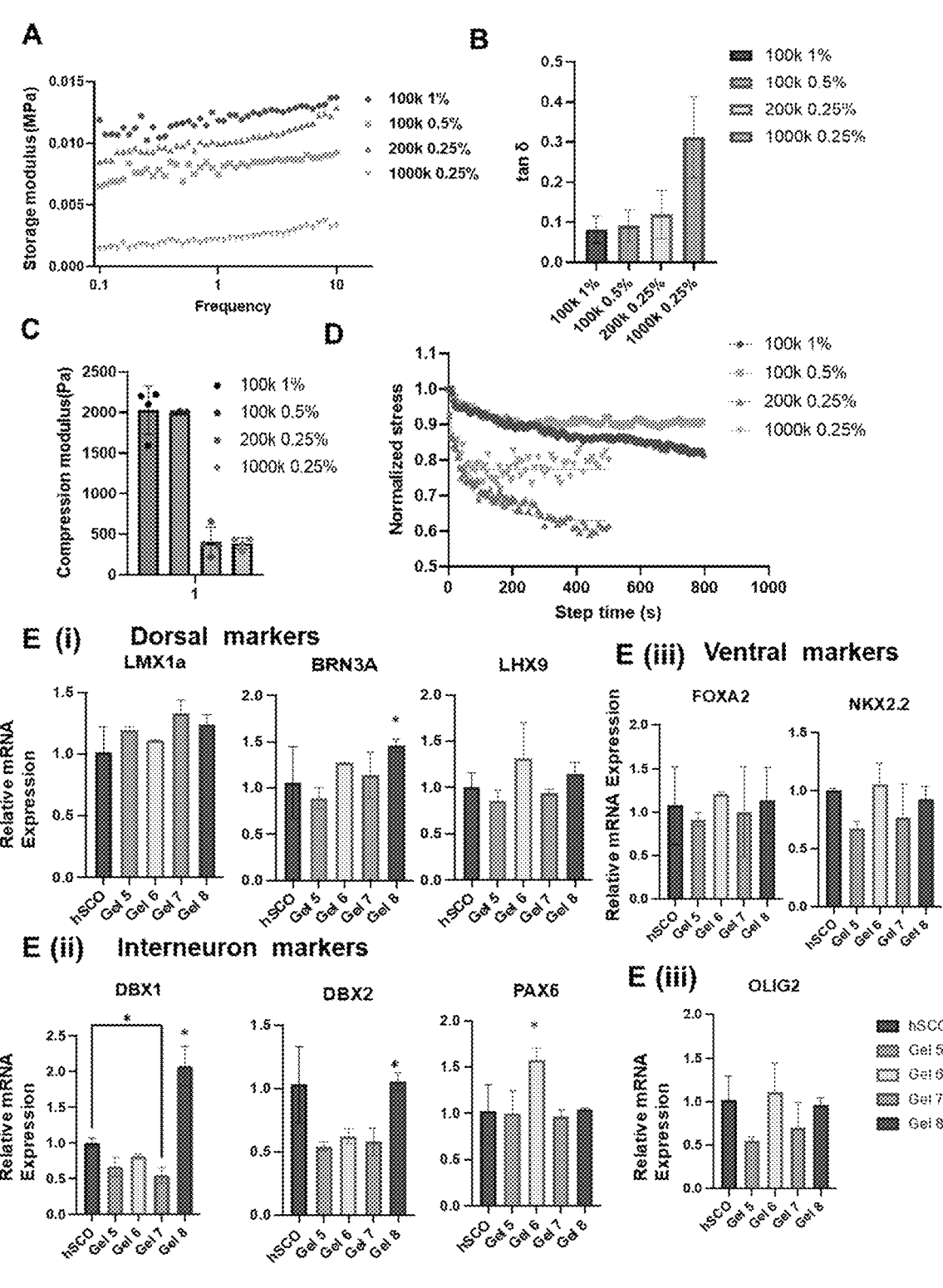
FIGS. 16A-16E depict fabrication and characterization of HAMA@HA-Cat hydrogels. The dynamic hydrogels were fabricated to enhance the hydrogel properties and potential ability to regulate hSCO derivation.

The mechanical properties of the four HAMA@HA-Cat hydrogels (Gel 5-8) were characterized. Using rheological tests, the shear modulus (FIG. 16A) and tanδ (FIG. 16B) of the four gels were measured. The modulus of Gel 8 was much lower than the other three groups and it had the highest tanδ of 0.3 in this study. Meanwhile, the compression modulus was determined, where Gel 5 and Gel 6 had similar compression moduli of ~2,000 Pa and Gel 7 and Gel 8 had similar compression moduli of ~400 Pa (FIG. 16C). Furthermore, the stress relaxation of the four hydrogels was evaluated, and the Maxwell model's regression was used to get the stress relaxation times of 373.0 s, 67.5 s, 94.6 s, and 19.4 s, respectively (FIG. 16D), all of which are less than those of the HAMA hydrogels. The hSCO patterning in the four HAMA@HA-Cat hydrogels was investigated (FIG. 16E). Gel 8 (the most viscoelastic HAMA@HA-Cat hydrogel) promoted the expression of dorsal marker BRN3A and interneuron markers DBX1 and DBX2 compared to other hydrogel conditions. Gel 6 promoted PAX6 expression. The ventral marker expression was not affected by different hydrogel properties. These results indicate that the viscoelasticity of dynamic hydrogels promotes hSCO patterning.

Figures 17A, 17B:
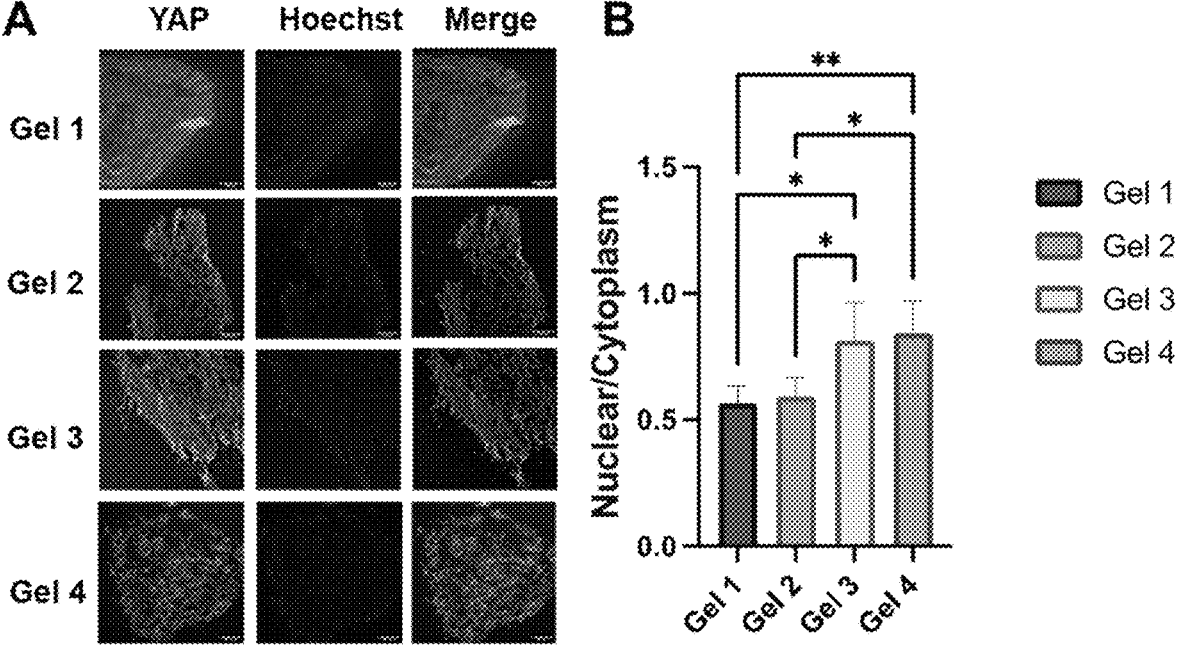
FIGS. 17A-17B depict histological sections for YAP localization to reveal the mechanism of hydrogel effects on hSCO patterning.

Mechanism of hydrogel effects on hSCO patterning: Considering the possible interplay between Hippo pathway and viscoelasticity of ECM, this study investigated the mechano-transduction mechanism by comparing the localization of YAP expression within the nuclei and cytoplasm (FIGS. 17A-17B) [46, 55, 59]. For this purpose, the hSCOs derived from different HAMA hydrogels were embedded in paraffin and sectioned into slices (6 m) for better imaging of 3D structure. The YAP and Hoechst staining were observed in the hSCOs from different hydrogel groups (FIG. 17A). In addition, the localization of YAP in the nuclei and cytoplasm was compared through image analysis by ImageJ (FIG. 17B). The hSCOs from the more elastic hydrogel groups (Gel 1 and Gel 2) had lower YAP nuclear localization when comparing to the hSCOs from viscoelastic hydrogels (Gel 3 and 4). Of note, the hydrogels with similar tan but different modulus had no difference in YAP nuclear localization between each other, such as Gel 1and 2, Gel 3 and 4. These results indicate that more viscoelastic hydrogels could lead to more nuclear YAP localization.

DISCUSSION

In this study, these findings provide a series of conclusions for 3D HAMA hydrogel microenvironments that influence the morphogenesis of hSCO and hSCO patterning under different viscoelasticity and stiffness of the static hydrogels as well as dynamic hydrogels. Using different concentrations and molecular weights of HA for crosslinking, the library of HAMA hydrogels with different mechanical property was established. For example, by using HA of different molecular weight with the same PEG-SH, the prorates can be manipulated. In addition, the ionic crosslinking mechanism and catechol chemistry were applied for hydrogel fabrication. Then, two groups of hydrogels with the similar modulus but different tan (Gel 2 and Gel 3) were selected for mimicking different ECM properties. The effects of stress relaxation were tested to reveal the influence of the viscoelasticity of HAMA hydrogels on spinal cord organoid patterning. Another two groups of hydrogels were included to show the effects of hydrogels with the similar tan but different modulus (Gel 1 vs. Gel 2, Gel 3 vs. Gel4). At the early stage of lineage-specific hSCO differentiation, the culture kinetics of the size and circularity of organoids were affected by different hydrogels, e.g., Gel 3 group showed initial small size but later became similar to other conditions. For the differentiation and patterning of ventral hSCOs, the stiffness and viscoelasticity of the hydrogels had a greater influence on dorsal and interneuron marker expression but less on ventral markers.

It was only recently that the viscoelastic, or time-dependent properties of the extracellular environment, has been shown to have significant influences on cell and tissue behaviors [23]. To date, only a few reports focused on the influence of tunable viscoelastic property of the 3D matrices on the interactions between stem cells and the microenvironment [60]. Conventionally, the reports of culturing mesenchymal stem cells with 2D or 3D matrices are abundant, while the investigations of hiPSC-derived organoid generation in 3D viscoclastic matrices are still limited [61]. The matrix viscoelasticity has just recently been recognized as a key component for regulating stem cell organoid morphogenesis for tumor and intestine tissue modeling [22, 23]. Tunable stress relaxation (viscoelasticity), stiffness, and RGD ligands were shown to have significant effects on hiPSC apicobasal polarization and lumen formation [22]. Furthermore, the viscoelastic properties of HA hydrogels has been observed to promote human neural progenitor cell maturation in 2D culture, with faster stress-relaxation increasing neurite extension and decreasing metabolic activity [62]. Here, the HAMA and HAMA@HACat hydrogels were fabricated by simple synthetic methods that provided a range of different biophysical properties. Four categories of hydrogels were selected for patterning hiPSC-derived spinal cord organoids which provide specific microenvironments for hSCO differentiation. Furthermore, this study can maintain the similar stiffness and the same polymer composition during the process of hydrogel fabrication while still allowing for the generation of hydrogels with different viscoelastic properties. Therefore, the effects of the viscoelasticity of hydrogels on the hSCO morphogenesis and differentiation can be isolated from the stiffness effects, serving as the main variable of the biophysical cues. The influence of the porosity of the hydrogels was thought to be small and the difference in different hydrogels was small.

HA was chosen due to its abundance in human central nervous system and its ability to generate unique matrices to compare with other natural polymers, such as alginate, gelatin, etc. HA and its derivatives have been currently used as 3D matrices for cell/tissue culture, especially in 3D printing and as granular hydrogels [63-65]. The synthesis of HAMA hydrogels was based on a classical and simple method that can provide a series of hydrogels. As a result of the limited extent of grafting on the HA chains, the low degree of crosslinking leads to the entanglement of free HAMA chains and results in the viscoelastic properties of the HAMA hydrogels to some extent. Biochemical and biophysical properties are both important for hiPSC-derived organoids morphogenesis and patterning. Usually, the two factors have different effects on the regulation of fate decision of hiPSCs that are intrinsically sensitive to their biophysical and biochemical environment [66-68]. In addition, the spinal cord injury repair can be realized using the synthetic scaffolds with various biochemical and biophysical cues [69]. Once embedded within HA hydrogels, hiPSCs sense the signals from the matrix during embryoid body formation, differentiation induction, expansion, and hSCO patterning, which leads to different morphogenesis results. Furthermore, the Matrigel free condition provides low matrix affinity microenvironments for hiPSC spheroid formation and inhibits hiPSC expansion or attachment. Therefore, these HA hydrogels without any cell-attachment factors can provide biophysical signaling for organoid patterning in suspension with minimal influence of biochemical signaling. Furthermore, the analysis of YAP localization provides another angle to understand mechanotransduction mechanism of HAMA hydrogels with different modulus and viscoelasticity. This study found that the nuclear translocation of YAP increases for the hydrogels with faster stress relaxation for both values of clastic moduli (Gel 3 and Gel 4). These results are consistent with previous study using 2D substrate culture [70, 71].

Biophysical cues such as stiffness, nanotopography, and mechanical strain can regulate the fate of the hiPSCs, such as maintaining the pluripotency or inducing differentiation. For example, substrate stiffness can influence neural induction and subtype specification of hiPSCs [72]. In addition, the topographic properties of the substrates can promote hiPSC differentiation into specific neural lineage [73]. In addition to stimulation by biophysical stimuli, directional growth and lineage-specific development of hiPSCs can be facilitated by biochemical factors. Therefore, the competition and synergistic effects between these two types of factors need to be investigated. Based on these findings, viscoelastic (i.e., high tanδ or shorter relaxation time) microenvironments promote dorsal or interneuron marker expression of hSCOs. Specifically, the stiffer hydrogels are preferred for hSCO differentiation than the softer hydrogels, and the viscoelastic hydrogels promote regional hSCO patterning compared to the elastic hydrogels. The growth factors that were added to the cultures were primarily for ventral organoid differentiation. The sonic hedgehog activator and RA are the two key factors for ventral patterning of spinal cord organoids. Comparing the ventral markers of different hSCOs from different hydrogels showed no significant difference, showing that the ventral markers are mainly affected by the differentiation factors, not the biophysical properties of hydrogels.

Vascularization is essential to the growth, maturity, and function of organoids, as a crucial component in organoid development. The ability to remove waste materials and supply nutrients and oxygen to the cells inside the organoids depends on proper vascularization. Several techniques are used to promote vascularization in organoids, including: co-culture with ECs [74], embedding in Matrigel [75], microfluidic systems [76, 77], decellularized tissue scaffolds [78], and in vivo maturation [79]. In this study, co-culturing hSCOs with hBVOh for organoid fusion was used. The presence of hBVOs altered the influence of different hydrogels on spinal cord organoid patterning. The effects of viscoelastic properties of the hydrogels become more dominant than the stiffness effects. The presence of hSCOs also had effects on the expression of EC, tight junction, and BSCB markers in the presence of hydrogels. For example, soft-elastic hydrogels promoted the tight junction and stiff-viscoelastic hydrogels appeared to promote the expression of glucose and efflux transporters. However, the hBVOs in this study were not mature and the main assessment was based on the gene expression. The vascularization structure was not assessed, which may need the mature hBVOs and dynamic perfusion culture environment.

This study fabricated HAMA hydrogels with different modulus and viscoelasticity to regulate hSCO patterning and co-culture with hBVOs. The four hydrogels are mainly separated into 2 groups, the elastic and viscoelastic groups. After testing hSCO differentiation and biocompatibility of the four hydrogels, the morphogenesis of hSCOs were observed. The viscoelasticity of the hydrogels influenced the size and circularity. Then, by comparing the gene and protein expression of hSCOs with different hydrogels, the results reveal that the stiffer hydrogels are preferred for hSCO differentiation and the viscoelastic hydrogels promote regional hSCO patterning compared to the elastic hydrogels. By coculturing hSCOs and hBVOs, this study was able to create a fusion of the two organoids. In the presence of hBVOs, the effects of viscoelastic properties became more dominant than the stiffness effects. Soft-elastic hydrogels promoted the tight junction and stiff-viscoelastic hydrogels appeared to promote the expression of glucose and efflux transporters. The viscoelasticity of dynamic hydrogels was also found to promote hSCO patterning. Furthermore, by analysis of the localization of YAP, this study found that the nuclei localization increased in the faster relaxation hydrogel groups.

The following patents, applications and publications as listed below and throughout this document are hereby incorporated by reference in their entirety herein.

REFERENCE LIST

[1] R. D'Mello, A. H. Dickenson, Spinal cord mechanisms of pain, British journal of anaesthesia 101 (1) (2008) 8-16.

[2] O. Revah et al., Maturation and circuit integration of transplanted human cortical organoids, Nature 610 (7931) (2022) 319-326.

[3] Z.-W. Du et al., Generation and expansion of highly pure motor neuron progenitors from human pluripotent stem cells, Nature communications 6 (1) (2015) 1-9.

[4] Y. Yan et al., 3D bioprinting of human neural tissues with functional connectivity, Cell Stem Cell 31 (2) (2024) 260-274 e7.

[5] T. Ogura et al., Three-dimensional induction of dorsal, intermediate and ventral spinal cord tissues from human pluripotent stem cells, Development 145 (16) (2018).

[6] T. Kaitsuka, F. Hakim, Response of pluripotent stem cells to environmental stress and its application for directed differentiation, Biology 10 (2) (2021) 84.

[7] T. Yamamoto et al., Improving the differentiation potential of pluripotent stem cells by optimizing culture conditions, Scientific Reports 12 (1) (2022) 14147.

[8] S. Gribaudo et al., Self-organizing models of human trunk organogenesis recapitulate spinal cord and spine co-morphogenesis, Nat Biotechnol (2023).

[9] J. H. Hor et al., Cell cycle inhibitors protect motor neurons in an organoid model of Spinal Muscular Atrophy, Cell death & disease 9 (11) (2018) 1-12.

[10] W. Xue et al., Generation of dorsoventral human spinal cord organoids via functionalizing composite scaffold for drug testing, iScience 26 (1) (2023) 105898.

[11] G. Zhou et al., Progress in the generation of spinal cord organoids over the past decade and future perspectives, Neural Regen Res 19 (5) (2024) 1013-1019.

[12] L.-Y. Jin et al., Blood-spinal cord barrier in spinal cord injury: a review, Journal of neurotrauma 38 (9) (2021) 1203-1224.

[13] L. Song et al., Functionalization of brain region-specific spheroids with isogenic microglia-like cells. Sci Rep 9:11055, 2019.

[14] L. Song et al., Assembly of human stem cell-derived cortical spheroids and vascular spheroids to model 3-D brain-like tissues, Scientific Reports 9 (1) (2019) 5977.

[15] W. L. Murphy et al., Materials as stem cell regulators, Nature materials 13 (6) (2014) 547-557.

[16] M. Simian, M. J. Bissell, Organoids: a historical perspective of thinking in three dimensions, Journal of Cell Biology 216 (1) (2017) 31-40.

[17] M. A. Lancaster, J. A. Knoblich, Organogenesis in a dish: modeling development and disease using organoid technologies, Science 345 (6194) (2014) 1247125.

[18] M. P. Lutolf, J. Hubbell, Synthetic biomaterials as instructive extracellular microenvironments for morphogenesis in tissue engineering, Nature biotechnology 23 (1) (2005) 47-55.

[19] J. G. Roth et al., Advancing models of neural development with biomaterials, Nature Reviews Neuroscience 22 (10) (2021) 593-615.

[20] O. Chaudhuri et al., Effects of extracellular matrix viscoelasticity on cellular behaviour, Nature 584 (7822) (2020) 535-546.

[21] A. Elosegui-Artola et al., Matrix viscoelasticity controls spatiotemporal tissue organization, Nat Mater 22 (2023) 117-127.

[22] D. Indana et al., Viscoelasticity and adhesion signaling in biomaterials control human pluripotent stem cell morphogenesis in 3D culture, Advanced Materials 33 (43) (2021) 2101966.

[23] A. Elosegui-Artola et al., Matrix viscoelasticity controls spatiotemporal tissue organization, Nature Materials 22 (1) (2023) 117-127.

[24] A. Elosegui-Artola, The extracellular matrix viscoelasticity as a regulator of cell and tissue dynamics, Curr Opin Cell Biol 72 (2021) 10-18.

[25] D. T. Wu et al., Viscoelastic biomaterials for tissue regeneration, Tissue Engineering Part C: Methods 28 (7) (2022) 289-300.

[26] S. Tang et al., Dynamic covalent hydrogels as biomaterials to mimic the viscoelasticity of soft tissues, Progress in Materials Science 120 (2021) 100738.

[27] J. R. E. Fraser et al., Hyaluronan: its nature, distribution, functions and turnover, Journal of internal medicine 242 (1) (1997) 27-33.

[28] L. C. Dijkgraaf et al., Normal cartilage structure, biochemistry, and metabolism: a review of the literature, Journal of oral and maxillofacial surgery 53 (8) (1995) 924-929.

[29] F. Horkay et al., Gel-like behavior in aggrecan assemblies, The Journal of chemical physics 128 (13) (2008).

[30] W. Zhu et al., Determination of kinetic changes of aggrecan-hyaluronan interactions in solution from its rheological properties, Journal of biomechanics 27 (5) (1994) 571-579.

[31] A. S. Fox et al., The basic science of articular cartilage: Structure, composition, and function Sports Health 1 (2009) 461-468.

[32] D. R. Zimmermann, M. T. Dours-Zimmermann, Extracellular matrix of the central nervous system: from neglect to challenge, Histochemistry and cell biology 130 (2008) 635-653.

[33] U. Rauch, Brain matrix: structure, turnover and necessity, Biochemical Society Transactions 35 (Pt 4) (2007) 656-660.

[34] K. T. Dicker et al., Hyaluronan: a simple polysaccharide with diverse biological functions, Acta biomaterialia 10 (4) (2014) 1558-1570.

[35] T. Chanmee et al., Hyaluronan: A modulator of the tumor microenvironment, Cancer Letters 375 (1) (2016) 20-30.

[36] Z. Z. Khaing, S. K. Seidlits, Hyaluronic acid and neural stem cells: implications for biomaterial design, Journal of Materials Chemistry B 3 (40) (2015) 7850-7866.

[37] R. Stern, Hyaluronan catabolisma new metabolic pathway, European journal of cell biology 83 (7) (2004) 317-325.

[38] R. Stern et al., Hyaluronan fragments: an information-rich system, European journal of cell biology 85 (8) (2006) 699-715.

[39] K. L. Perkins et al., Brain extracellular space, hyaluronan, and the prevention of epileptic seizures, Reviews in the Neurosciences 28 (8) (2017) 869-892.

[40] A. Lundell et al., Structural basis for interactions between tenascins and lectican C-type lectin domains: evidence for a crosslinking role for tenascins, Structure 12 (8) (2004) 1495-1506.

[41] Z. Zhu et al., Hyaluronic acid: a versatile biomaterial in tissue engineering, Plastic and Aesthetic Research 4 (2017) 219-227.

[42] S. Pedron et al., Extracellular hyaluronic acid influences the efficacy of EGFR tyrosine kinase inhibitors in a biomaterial model of glioblastoma, Advanced healthcare materials 6 (21) (2017) 1700529.

[43] M. Y. Kwon et al., Influence of hyaluronic acid modification on CD44 binding towards the design of hydrogel biomaterials, Biomaterials 222 (2019) 119451.

[44] S. Gokila et al., Development of 3D scaffolds using nanochitosan/silk-fibroin/hyaluronic acid biomaterials for tissue engineering applications, International journal of biological macromolecules 120 (2018) 876-885.

[45] Y. Cao et al., Covalently Attached Slippery Surface Coatings to Reduce Protein Adsorptions on Poly(dimethylsiloxane) Planar Surfaces and 3D Microfluidic Channels., ACS Applied Materials and Interfaces 15 (2023) 9987-9995.

[46] X. Chen et al., Surface engineering of auxetic scaffolds for neural and vascular differentiation from human pluripotent stem cells, Adv Healthc Mater 12 (6) (2023) e2202511.

[47] J.-H. Hor, S.-Y. Ng, Generating ventral spinal organoids from human induced pluripotent stem cells, Methods in Cell Biology, Elsevier2020, pp. 257-277.

[48] J.-H. Lee et al., Production of human spinal-cord organoids recapitulating neural-tube morphogenesis, Nature Biomedical Engineering 6 (4) (2022) 435-448.

[49] R. Jeske et al., Engineering human mesenchymal bodies in a novel 3-D printed microchannel bioreactor for studying extracellular vesicle biogenesis, Bioengineering (Basel) 9 (12) (2022) 795.

[50] X. Yuan et al., Engineering Extracellular Vesicles by Three-dimensional Dynamic Culture of Human Mesenchymal Stem Cells, Journal of Extracellular Vesicles 11 (6) (2022) e12235.

[51] L. Muok et al., Extracellular Vesicle Biogenesis of Three-dimensional Human Pluripotent Stem Cells in a Novel Vertical-Wheel Bioreactor, Journal of Extracellular Biology 3 (2024) e133.

[52] R. Jeske et al., Upscaling Human Mesenchymal Stem Cell Production in a Novel Vertical Wheel Bioreactor Enhances Extracellular Vesicle Secretion and Cargo Profile, Bioactive Materials 25 (2023) 732-747.

[53] T. Qian et al., Directed differentiation of human pluripotent stem cells to blood-brain barrier endothelial cells, Science advances 3 (11) (2017) e1701679.

[54] R. A. Wimmer et al., Human blood vessel organoids as a model of diabetic vasculopathy, Nature 565 (2019) 505-510.

[55] L. Song et al., Nanotopography promoted neuronal differentiation of human induced pluripotent stem cells, Colloids and Surfaces B: Biointerfaces 148 (2016) 49-58.

[56] O. Chaudhuri, Viscoelastic hydrogels for 3D cell culture, Biomaterials science 5 (8) (2017) 1480-1490.

[57] H. Y. Tan et al., Human mini-brain models, Nat Biomed Eng 5 (1) (2021) 11-25.

[58] X. Chen et al., Dynamic 3D on-chip BBB Model Design, Development, and Applications in Neurological Diseases, Cells 10 (2021) 3183.

[59] J. Bejoy et al., Wnt-Yes associated protein interactions during neural tissue patterning of human induced pluripotent stem cells, Tissue Engineering Part A 24 (7-8) (2018) 546-558.

[60] F. Gattazzo et al., Extracellular matrix: a dynamic microenvironment for stem cell niche, Biochimica et Biophysica Acta (BBA)-General Subjects 1840 (8) (2014) 2506-2519.

[61] I. Bissoli et al., Induced pluripotent stem cell-based models: Are we ready for that heart in a dish?, Frontiers in Cell and Developmental Biology 11 (2023) 1129263.

[62] J. G. Roth et al., Tunable hydrogel viscoelasticity modulates human neural maturation, Science Advances 9 (42) (2023) eadh8313.

[63] J. Hauptstein et al., Hyaluronic acid-based bioink composition enabling 3D bioprinting and improving quality of deposited cartilaginous extracellular matrix, Advanced Healthcare Materials 9 (15) (2020) 2000737.

[64] M. Asadikorayem et al., Zwitterionic Granular Hydrogel for Cartilage Tissue Engineering, Advanced Healthcare Materials (2023) 2301831.

[65] V. G. Muir et al., Sticking Together: Injectable Granular Hydrogels with Increased Functionality via Dynamic Covalent Inter-Particle Crosslinking, Small 18 (36) (2022) 2201115.

[66] S. Ding et al., Modulation of human mesenchymal and pluripotent stem cell behavior using biophysical and biochemical cues: A review, Biotechnology and bioengineering 114 (2) (2017) 260-280.

[67] P.-Y. Wang et al., Modulation of human multipotent and pluripotent stem cells using surface nanotopographies and surface-immobilised bioactive signals: A review, Acta biomaterialia 45 (2016) 31-59.

[68] R. G. Ireland, C. A. Simmons, Human pluripotent stem cell mechanobiology: manipulating the biophysical microenvironment for regenerative medicine and tissue engineering applications, Stem Cells 33 (11) (2015) 3187-3196.

[69] Y. Li et al., Review of advances in electrospinning-based strategies for spinal cord regeneration, Materials Today Chemistry 24 (2022) 100944.

[70] O. Chaudhuri et al., Hydrogels with tunable stress relaxation regulate stem cell fate and activity, Nature materials 15 (3) (2016) 326-334.

[71] B. Cheng et al., Predicting YAP/TAZ nuclear translocation in response to ECM mechanosensing, Biophysical journal 122 (1) (2023) 43-53.

[72] Y. Sun et al., Hippo/YAP-mediated rigidity-dependent motor neuron differentiation of human pluripotent stem cells, Nature materials 13 (6) (2014) 599-604.

[73] F. Pan et al., Topographic effect on human induced pluripotent stem cells differentiation towards neuronal lineage, Biomaterials 34 (33) (2013) 8131-8139.

[74] G. Pettinato et al., Generation of fully functional hepatocyte-like organoids from human induced pluripotent stem cells mixed with Endothelial Cells, Scientific reports 9 (1) (2019) 8920.

[75] A. Khanna et al., Extracellular matrix-based biomaterials for cardiovascular tissue engineering, Journal of cardiovascular development and disease 8 (11) (2021) 137.

[76] K. A. Homan et al., Flow-enhanced vascularization and maturation of kidney organoids in vitro, Nature methods 16 (3) (2019) 255-262.

[77] S. Zhang et al., Vascularized organoids on a chip: strategies for engineering organoids with functional vasculature, Lab on a Chip 21 (3) (2021) 473-488.

[78] E. Lupon et al., Engineering vascularized composite allografts using natural scaffolds: a systematic review, Tissue Engineering Part B: Reviews 28 (3) (2022) 677-693.

[79] A. A. Mansour et al., An in vivo model of functional and vascularized human brain organoids, Nature biotechnology 36 (5) (2018) 432-441.

What is claimed is:

1. A method of modeling a spinal cord, the method comprising culturing a plurality of induced pluripotent stem cells on a cell scaffold to form a spinal cord spheroid or organoid or a fragment thereof, the cell scaffold comprising methacrylated hyaluronic acid (HAMA) and dopamine-modified hyaluronic acid (HA-Cat);

wherein the method causes the spinal cord spheroid or organoid or a fragment thereof to express one or more ventral markers, dorsal markers, and/or interneuron markers.

2. The method of claim 1, wherein the induced pluripotent stem cells comprise healthy cells.

3. The method of claim 1, wherein the induced pluripotent stem cells comprise diseased or abnormal cells.

4. The method of claim 1, wherein the induced pluripotent stem cells are human.

5. The method of claim 1, wherein the cell scaffold comprises:

up to about 2 wt % HAMA; and up to about 2 wt % HA-Cat.

6. The method of claim 1, wherein:

the HAMA has a molecular weight of from about 50 kDa to about 2000 kDa; and the HA-Cat has a molecular weight of from about 50 kDa to about 2000 kDa.

7. The method of claim 1, wherein the cell scaffold further comprises a crosslinker comprising:

up to about 1 wt % 2-hydroxy-4'-(2-hydroxyethoxy)-2-methylpropiophenone (NHS); and up to about 2 wt % thiolated polyethylene glycol (PEG).

8. The method of claim 1, wherein the cell scaffold further comprises from about 5 mM to about 15 mM $Fe^{3+}$.

9. The method of claim 1, wherein the cell scaffold has a damping factor (tan δ) of from about 0.03 to about 0.3.

10. The method of claim 1, wherein the cell scaffold has a compression modulus (E) of from about 250 Pa to about 10,000 Pa.

11. The method of claim 1, wherein the cell scaffold has a stress relaxation time of from about 10 seconds to about 1000 seconds.

12. The method of claim 1, wherein:

the one or more ventral markers comprise SOX2, FOXA2, LHX3, NKX2.2, and/or OLIG2;

the one or more dorsal markers comprise PAX7, LHX3, LMX1, LHX9, and/or BRN3; and the one or more interneuron markers comprise DBX1, DBX2, and or PAX6.

13. The method of claim 1, wherein, compared to a reference spinal cord spheroid or organoid or fragment thereof not cultured on the cell scaffold, the spinal cord spheroid or organoid or fragment thereof comprises:

at least about 1.5-fold greater expression of the one or more ventral markers;

at least about 2-fold greater expression of the one or more dorsal markers; and/or at least about 2-fold greater expression of the one or more interneuron markers.

* * * * *

SEQUENCE LISTING

```
Sequence total quantity: 40
SEQ ID NO: 1              moltype = DNA  length = 21
FEATURE                  Location/Qualifiers
misc_feature             1..21
                         note = Description of sequence: Forward primer, target
                          gene: GLUT-1
source                   1..21
                         mol_type = other DNA
                         organism = synthetic construct
SEQUENCE: 1
agcaactgtg tggtccctac g                                           21

SEQ ID NO: 2              moltype = DNA  length = 21
FEATURE                  Location/Qualifiers
misc_feature             1..21
                         note = Description of sequence: Forward primer, target
                          gene: BCRP
source                   1..21
                         mol_type = other DNA
                         organism = synthetic construct
SEQUENCE: 2
caggtgtgcg tcagaatcat c                                           21

SEQ ID NO: 3              moltype = DNA  length = 21
FEATURE                  Location/Qualifiers
misc_feature             1..21
                         note = Description of sequence: Forward primer, target
                          gene: PGP
source                   1..21
                         mol_type = other DNA
                         organism = synthetic construct
SEQUENCE: 3
accactctcc cacctccctt a                                           21

SEQ ID NO: 4              moltype = DNA  length = 21
FEATURE                  Location/Qualifiers
misc_feature             1..21
                         note = Description of sequence: Forward primer, target
                          gene: Dbx1
source                   1..21
                         mol_type = other DNA
                         organism = synthetic construct
SEQUENCE: 4
agcgagacga cgtttctgaa g                                           21
```

-continued

```
SEQ ID NO: 5              moltype = DNA   length = 21
FEATURE                   Location/Qualifiers
misc_feature              1..21
                          note = Description of sequence: Forward primer, target
                           gene: Dbx2
source                    1..21
                          mol_type = other DNA
                          organism = synthetic construct
SEQUENCE: 5
ggtatggccc acccagagat a                                           21

SEQ ID NO: 6              moltype = DNA   length = 21
FEATURE                   Location/Qualifiers
misc_feature              1..21
                          note = Description of sequence: Forward primer, target
                           gene: FOXA2
source                    1..21
                          mol_type = other DNA
                          organism = synthetic construct
SEQUENCE: 6
cggatcgagg acaagtgaga g                                           21

SEQ ID NO: 7              moltype = DNA   length = 21
FEATURE                   Location/Qualifiers
misc_feature              1..21
                          note = Description of sequence: Forward primer, target
                           gene: Lmx1a
source                    1..21
                          mol_type = other DNA
                          organism = synthetic construct
SEQUENCE: 7
gggaacccag aatgagttgg t                                           21

SEQ ID NO: 8              moltype = DNA   length = 21
FEATURE                   Location/Qualifiers
misc_feature              1..21
                          note = Description of sequence: Forward primer, target
                           gene: NKX2.2
source                    1..21
                          mol_type = other DNA
                          organism = synthetic construct
SEQUENCE: 8
gcctctcctt ctgaaccttg g                                           21

SEQ ID NO: 9              moltype = DNA   length = 21
FEATURE                   Location/Qualifiers
misc_feature              1..21
                          note = Description of sequence: Forward primer, target
                           gene: BRN3
source                    1..21
                          mol_type = other DNA
                          organism = synthetic construct
SEQUENCE: 9
cggtaggact tggctgtgag a                                           21

SEQ ID NO: 10             moltype = DNA   length = 42
FEATURE                   Location/Qualifiers
misc_feature              1..42
                          note = Description of sequence: Forward primer, target
                           gene: LHX9
source                    1..42
                          mol_type = other DNA
                          organism = synthetic construct
SEQUENCE: 10
agccctgctt ctagccaatg tgctccggac catgaaatcc ta                   42

SEQ ID NO: 11             moltype = DNA   length = 21
FEATURE                   Location/Qualifiers
misc_feature              1..21
                          note = Description of sequence: Forward primer, target
                           gene: OLIG2
source                    1..21
                          mol_type = other DNA
                          organism = synthetic construct
SEQUENCE: 11
aaactcctcc acgtgcttcc t                                           21

SEQ ID NO: 12             moltype = DNA   length = 21
```

-continued

```
FEATURE                  Location/Qualifiers
misc_feature             1..21
                         note = Description of sequence: Forward primer, target
                          gene: VWF
source                   1..21
                         mol_type = other DNA
                         organism = synthetic construct
SEQUENCE: 12
cctcaactgc caccaatgac t                                                 21

SEQ ID NO: 13            moltype = DNA  length = 21
FEATURE                  Location/Qualifiers
misc_feature             1..21
                         note = Description of sequence: Forward primer, target
                          gene: ZO1
source                   1..21
                         mol_type = other DNA
                         organism = synthetic construct
SEQUENCE: 13
cgggactgtt ggtattggct a                                                 21

SEQ ID NO: 14            moltype = DNA  length = 21
FEATURE                  Location/Qualifiers
misc_feature             1..21
                         note = Description of sequence: Forward primer, target
                          gene: ISL1
source                   1..21
                         mol_type = other DNA
                         organism = synthetic construct
SEQUENCE: 14
gccagtccag agagacacga c                                                 21

SEQ ID NO: 15            moltype = DNA  length = 21
FEATURE                  Location/Qualifiers
misc_feature             1..21
                         note = Description of sequence: Forward primer, target
                          gene: OCLN
source                   1..21
                         mol_type = other DNA
                         organism = synthetic construct
SEQUENCE: 15
ccaattgctg ccacaagaac t                                                 21

SEQ ID NO: 16            moltype = DNA  length = 21
FEATURE                  Location/Qualifiers
misc_feature             1..21
                         note = Description of sequence: Forward primer, target
                          gene: CD31
source                   1..21
                         mol_type = other DNA
                         organism = synthetic construct
SEQUENCE: 16
agtgtgacaa gcgtcatggt g                                                 21

SEQ ID NO: 17            moltype = DNA  length = 21
FEATURE                  Location/Qualifiers
misc_feature             1..21
                         note = Description of sequence: Forward primer, target
                          gene: CDH5
source                   1..21
                         mol_type = other DNA
                         organism = synthetic construct
SEQUENCE: 17
tcgctgttgt cacatctcag g                                                 21

SEQ ID NO: 18            moltype = DNA  length = 21
FEATURE                  Location/Qualifiers
misc_feature             1..21
                         note = Description of sequence: Forward primer, target
                          gene: CLDN1
source                   1..21
                         mol_type = other DNA
                         organism = synthetic construct
SEQUENCE: 18
tgggtttctt gccttaacca g                                                 21

SEQ ID NO: 19            moltype = DNA  length = 21
FEATURE                  Location/Qualifiers
misc_feature             1..21
```

```
                          note = Description of sequence: Forward primer, target
                           gene: GFAP
source                    1..21
                          mol_type = other DNA
                          organism = synthetic construct
SEQUENCE: 19
gatctctgcc tcagtgctcc a                                                   21

SEQ ID NO: 20             moltype = DNA  length = 21
FEATURE                   Location/Qualifiers
misc_feature              1..21
                          note = Description of sequence: Forward primer, target
                           gene: SELP
source                    1..21
                          mol_type = other DNA
                          organism = synthetic construct
SEQUENCE: 20
tagcgatgaa ctgctccaac c                                                   21

SEQ ID NO: 21             moltype = DNA  length = 21
FEATURE                   Location/Qualifiers
misc_feature              1..21
                          note = Description of sequence: Reverse primer, target
                           gene: GLUT-1
source                    1..21
                          mol_type = other DNA
                          organism = synthetic construct
SEQUENCE: 21
aaggtccggc ctttagtctc a                                                   21

SEQ ID NO: 22             moltype = DNA  length = 22
FEATURE                   Location/Qualifiers
misc_feature              1..22
                          note = Description of sequence: Reverse primer, target
                           gene: BCRP
source                    1..22
                          mol_type = other DNA
                          organism = synthetic construct
SEQUENCE: 22
tccaggagtg gtcagattcc tt                                                  22

SEQ ID NO: 23             moltype = DNA  length = 21
FEATURE                   Location/Qualifiers
misc_feature              1..21
                          note = Description of sequence: Reverse primer, target
                           gene: PGP
source                    1..21
                          mol_type = other DNA
                          organism = synthetic construct
SEQUENCE: 23
tttagctggg ctgcgtttac a                                                   21

SEQ ID NO: 24             moltype = DNA  length = 21
FEATURE                   Location/Qualifiers
misc_feature              1..21
                          note = Description of sequence: Reverse primer, target
                           gene: Dbx1
source                    1..21
                          mol_type = other DNA
                          organism = synthetic construct
SEQUENCE: 24
tagggaaagg cgaaggtctt g                                                   21

SEQ ID NO: 25             moltype = DNA  length = 21
FEATURE                   Location/Qualifiers
misc_feature              1..21
                          note = Description of sequence: Reverse primer, target
                           gene: Dbx2
source                    1..21
                          mol_type = other DNA
                          organism = synthetic construct
SEQUENCE: 25
ctgtgacacc acggctttct t                                                   21

SEQ ID NO: 26             moltype = DNA  length = 21
FEATURE                   Location/Qualifiers
misc_feature              1..21
                          note = Description of sequence: Reverse primer, target
                           gene: FOXA2
```

```
source                    1..21
                          mol_type = other DNA
                          organism = synthetic construct
SEQUENCE: 26
ggtgggggtg ttatggattt c                                          21

SEQ ID NO: 27             moltype = DNA   length = 21
FEATURE                   Location/Qualifiers
misc_feature              1..21
                          note = Description of sequence: Reverse primer, target
                           gene: Lmx1a
source                    1..21
                          mol_type = other DNA
                          organism = synthetic construct
SEQUENCE: 27
ccaatgatgt ccccagaaat g                                          21

SEQ ID NO: 28             moltype = DNA   length = 21
FEATURE                   Location/Qualifiers
misc_feature              1..21
                          note = Description of sequence: Reverse primer, target
                           gene: NKX2.2
source                    1..21
                          mol_type = other DNA
                          organism = synthetic construct
SEQUENCE: 28
acattaacgc tgggacggtt t                                          21

SEQ ID NO: 29             moltype = DNA   length = 21
FEATURE                   Location/Qualifiers
misc_feature              1..21
                          note = Description of sequence: Reverse primer, target
                           gene: BRN3
source                    1..21
                          mol_type = other DNA
                          organism = synthetic construct
SEQUENCE: 29
tgttctgttt tcgcccaaca t                                          21

SEQ ID NO: 30             moltype = DNA   length = 43
FEATURE                   Location/Qualifiers
misc_feature              1..43
                          note = Description of sequence: Reverse primer, target
                           gene: LHX9
source                    1..43
                          mol_type = other DNA
                          organism = synthetic construct
SEQUENCE: 30
tgttgtgagg gcagagcact acaagatttg ttctccctgc aaa                  43

SEQ ID NO: 31             moltype = DNA   length = 21
FEATURE                   Location/Qualifiers
misc_feature              1..21
                          note = Description of sequence: Reverse primer, target
                           gene: OLIG2
source                    1..21
                          mol_type = other DNA
                          organism = synthetic construct
SEQUENCE: 31
tgttacacgg cagacgctac a                                          21

SEQ ID NO: 32             moltype = DNA   length = 21
FEATURE                   Location/Qualifiers
misc_feature              1..21
                          note = Description of sequence: Reverse primer, target
                           gene: VWF
source                    1..21
                          mol_type = other DNA
                          organism = synthetic construct
SEQUENCE: 32
gaactggccc acagggtaga t                                          21

SEQ ID NO: 33             moltype = DNA   length = 21
FEATURE                   Location/Qualifiers
misc_feature              1..21
                          note = Description of sequence: Reverse primer, target
                           gene: ZO1
source                    1..21
                          mol_type = other DNA
```

```
                              organism = synthetic construct
SEQUENCE: 33
cccccattta ctggctggta t                                               21

SEQ ID NO: 34              moltype = DNA   length = 21
FEATURE                   Location/Qualifiers
misc_feature              1..21
                          note = Description of sequence: Reverse primer, target
                           gene: ISL1
source                    1..21
                          mol_type = other DNA
                          organism = synthetic construct
SEQUENCE: 34
gtcactctgc aaggcgaagt c                                               21

SEQ ID NO: 35              moltype = DNA   length = 21
FEATURE                   Location/Qualifiers
misc_feature              1..21
                          note = Description of sequence: Reverse primer, target
                           gene: OCLN
source                    1..21
                          mol_type = other DNA
                          organism = synthetic construct
SEQUENCE: 35
atttctccaa ggtcccacag c                                               21

SEQ ID NO: 36              moltype = DNA   length = 21
FEATURE                   Location/Qualifiers
misc_feature              1..21
                          note = Description of sequence: Reverse primer, target
                           gene: CD31
source                    1..21
                          mol_type = other DNA
                          organism = synthetic construct
SEQUENCE: 36
aggctttggt gagacccact t                                               21

SEQ ID NO: 37              moltype = DNA   length = 21
FEATURE                   Location/Qualifiers
misc_feature              1..21
                          note = Description of sequence: Reverse primer, target
                           gene: CDH5
source                    1..21
                          mol_type = other DNA
                          organism = synthetic construct
SEQUENCE: 37
agtggaagat gcatgggtga c                                               21

SEQ ID NO: 38              moltype = DNA   length = 21
FEATURE                   Location/Qualifiers
misc_feature              1..21
                          note = Description of sequence: Reverse primer, target
                           gene: CLDN1
source                    1..21
                          mol_type = other DNA
                          organism = synthetic construct
SEQUENCE: 38
agaaagcatc gggccatact c                                               21

SEQ ID NO: 39              moltype = DNA   length = 21
FEATURE                   Location/Qualifiers
misc_feature              1..21
                          note = Description of sequence: Reverse primer, target
                           gene: GFAP
source                    1..21
                          mol_type = other DNA
                          organism = synthetic construct
SEQUENCE: 39
gatatgcagg agggtgggtt t                                               21

SEQ ID NO: 40              moltype = DNA   length = 21
FEATURE                   Location/Qualifiers
misc_feature              1..21
                          note = Description of sequence: Reverse primer, target
                           gene: SELP
source                    1..21
                          mol_type = other DNA
                          organism = synthetic construct
```

-continued

SEQUENCE: 40
ccattctctt ggcatgctgt t                                    21